(12) United States Patent
Ohwada et al.

(10) Patent No.: US 9,856,278 B2
(45) Date of Patent: Jan. 2, 2018

(54) LYSOPHOSPHATIDYLSERINE DERIVATIVE

(71) Applicant: THE UNIVERSITY OF TOKYO, Tokyo (JP)

(72) Inventors: Tomohiko Ohwada, Tokyo (JP); Sho Nakamura, Tokyo (JP); Sejin Jung, Tokyo (JP); Yuko Otani, Tokyo (JP); Misa Sayama, Tokyo (JP); Junken Aoki, Miyagi (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/322,041

(22) PCT Filed: Jul. 3, 2015

(86) PCT No.: PCT/JP2015/069345
§ 371 (c)(1),
(2) Date: Apr. 4, 2017

(87) PCT Pub. No.: WO2016/002948
PCT Pub. Date: Jan. 7, 2016

(65) Prior Publication Data
US 2017/0210767 A1      Jul. 27, 2017

(30) Foreign Application Priority Data
Jul. 4, 2014      (JP) ................................. 2014-139090

(51) Int. Cl.
*C07F 9/09*      (2006.01)
*C07F 9/12*      (2006.01)

(52) U.S. Cl.
CPC . *C07F 9/12* (2013.01); *C07F 9/09* (2013.01)

(58) Field of Classification Search
None
See application file for complete search history.

(56) References Cited

U.S. PATENT DOCUMENTS

| 2009/0304577 A1 | 12/2009 | Matossian-Rogers |
| 2010/0130737 A1 | 5/2010 | Itoh et al. |
| 2013/0230536 A1 | 9/2013 | Granger et al. |
| 2015/0337046 A1 | 11/2015 | Granger et al. |

FOREIGN PATENT DOCUMENTS

| JP | 2007-267601 A | 10/2007 | |
| JP | 2007-284402 A | 11/2007 | |
| JP | 2009-505640 A | 2/2009 | |
| JP | 2010-502183 A | 1/2010 | |
| JP | 2010-184867 A | 8/2010 | |
| WO | WO 2006/088246 A1 | 8/2006 | |
| WO | WO 2012/157746 A1 | 11/2012 | |
| WO | WO 2014/119649 * | 8/2014 | ................ C07F 9/09 |

OTHER PUBLICATIONS

Inoue et al., "TGFα shedding assay: an accurate and versatile method for detecting GPCR activation", Nature Methods, vol. 9, No. 10, Oct. 2012, pp. 1021-1029.
International Search Report for PCT/JP2015/069345 (PCT/ISA/210) dated Oct. 6, 2015.
Martin et al.,"Interactions of lysophospholipids and mast cell", Nature, vol. 279, May 17, 1979, pp. 250-252.
Smith et al., "The Exogenous Lipid Requirement for Histamine Release from Rat Peritoneal Mast Cells Stimulated by Concanavalin A", Febs Letters, vol. 105, No. 1, Sep. 1979, pp. 58-62.
Tokumura, "Physiological Significance of Lysophospholipids that Act on the Lumen Side of Mammalian Lower Digestive Tracts", Journal of Health Science, vol. 57, No. 2, 2011, pp. 115-128.

* cited by examiner

*Primary Examiner* — Alicia L Otton
(74) *Attorney, Agent, or Firm* — Birch, Stewart, Kolasch & Birch, LLP

(57) ABSTRACT

An object of the present invention is to provide a lysophosphatidylserine derivative or a salt thereof.
The present invention provides a lysophosphatidylserine derivative or a salt thereof, or a pharmaceutical composition or a lysophosphatidylserine receptor function modulator comprising said compound or a salt thereof.

14 Claims, No Drawings

LYSOPHOSPHATIDYLSERINE DERIVATIVE

TECHNICAL FIELD

The present invention relates to lysophosphatidylserine derivatives or salts thereof. More particularly, the present invention relates said compounds or salts thereof having an activity for modulating the functions of lysophosphatidylserine receptors. The invention also relates to pharmaceutical compositions or lysophosphatidylserine receptor function modulators comprising said compounds or salts thereof.

BACKGROUND ART

Lysophospholipids is the collective term for phospholipids having a single acyl group. Compared to diacylphospholipids that constitute cell membranes, lysophospholipids are less hydrophobic and have such a property that they can easily become free from the cell membranes. Acting as signal molecules between cells or membranes, some lysophospholipids have been shown to have an important role in vivo and it has heretofore been known that phospholipids in biomembranes are hydrolyzed to produce lysophospholipids when inflammatory reactions such as tissue damage take place (Patent Document 1). Lysophosphatidylserine (LysoPS) which is a kind of lysophospholipids is known to be involved in acute inflammations due to degranulation of mast cells (Non-Patent Documents 1 and 2). As LysoPS receptors, the G protein coupled receptors GPR34, P2Y10, A630033H20Rik and GPR174 have been identified (Non-Patent Document 3) and among these, GPR34, P2Y10, and GPR174 are referred to as $LPS_1$, $LPS_2$, and $LPS_3$ (Non-Patent Document 4). Among these, $LPS_1$ has been reported to be involved in signaling for inducing or enhancing the degranulation reaction of mast cells so that it can be a target for the treatment of allergic diseases and chronic inflammatory diseases (Patent Documents 1 and 2). It is also known that a certain lysophosphatidylserine derivative (lysophosphatidylthreonine) is a potent promoter of the degranulation reaction of mast cells (Patent Documents 3 and 4).

Methods for screening compounds useful as therapeutics for autoimmunity and the discovery of lysophosphatidylserine and derivatives thereof by such screening methods have been reported (Patent Document 5). Autoimmune diseases is the collective term for diseases that become symptomatic when an immune system which is normally a defense mechanism against foreign bodies responds excessively and even attacks normal cells or tissues of the self; autoimmune diseases are roughly divided into systemic autoimmune diseases that affect the whole body and organ-specific diseases that affect only certain organs. In general, autoimmune diseases often end up with chronic or refractory diseases and some of them are cited by the Ministry of Health, Labour and Welfare in the List of Diseases under Intensive Study. Much research has been made on the methods for treating autoimmune diseases and the methods reported so far include a method for treating chronic inflammation due to autoimmune disease using a cytokine specific antibody involved in inflammation (Patent Document 6) and a therapeutic method for disease that involves neutralizing a pathogenic autoantibody (Patent Document 7). However, much is left unraveled about the cause of autoimmune disease and no effective therapy has yet been established for many autoimmune diseases. To treat autoimmune disease, medications that suppress the immune system or anti-inflammatory drugs that mitigate inflammation (steroids or non-steroids) are being used as drugs of first choice.

CITATION LIST

Patent Documents

Patent Document 1: JP 2007-267601A
Patent Document 2: WO 2006/088246A
Patent Document 3: JP 2007-284402A
Patent Document 4: JP 2010-184867A
Patent Document 5: WO 2012/157746A
Patent Document 6: JP 2010-502183A
Patent Document 7: JP 2009-505640A

Non-Patent Documents

Non-Patent Document 1: Nature, vol. 279, pp. 250-252 (1979)
Non-Patent Document 2: J. C. FEBS Lett., vol. 105, pp. 58-62 (1979)
Non-Patent Document 3: Journal of Health Science, vol. 57, no. 2, pp. 115-128 (2011)
Non-Patent Document 4: Nature Methods, vol. 9, no. 10, pp. 1021-1029 (2012).

SUMMARY OF INVENTION

Technical Problem

An object of the present invention is to provide lysophosphatidylserine derivatives or salts thereof having an activity for modulating the functions of lysophosphatidylserine receptors. Another object of the present invention is to provide pharmaceutical compositions or lysophosphatidylserine receptor function modulators comprising said compounds or salts thereof.

Solution to Problem

The present inventors conducted intensive studies with a view to attaining the stated objects and found compounds or salts thereof having activity as GPR34, P2Y10 and/or GPR174 agonist and have eventually accomplished the present invention which relates to the compounds or salts thereof that have lysophosphatidylserine receptor agonistic activities.

Briefly, the present invention relates to the compounds, pharmaceutical compositions and lysophosphatidylserine receptor function modulators that are described below.

(1) A compound represented by formula (I):

[Formula 1]

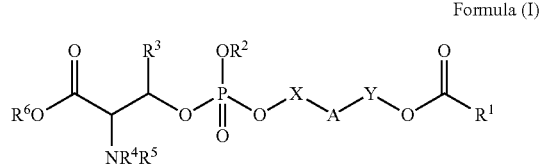

Formula (I)

wherein:
$R^1$ is represented by the following group:
$C_{1-30}$ alkyl optionally substituted by one or more $R^8$, $C_{2-30}$ alkenyl optionally substituted by one or more $R^8$, or $C_{2-30}$ alkynyl optionally substituted by one or more $R^8$, where $R^8$ is independently selected from among $C_{1-6}$ alkyl, $C_{1-6}$ alkoxy, and a halogen atom, or is a group represented by the formula:

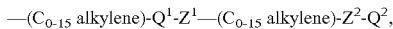
—($C_{0-15}$ alkylene)-$Q^1$-$Z^1$—($C_{0-15}$ alkylene)-$Z^2$-$Q^2$, where $Q^1$ is a $C_{3-10}$ cycloalkylene optionally substituted by one or more $R^9$, a 5- to 10-membered heterocyclylene optionally substituted by one or more $R^9$, a $C_{6-10}$ arylene optionally substituted by one or more $R^9$, or a 5- to 10-membered heteroarylene optionally substituted by one or more $R^9$, where $R^9$ is independently selected from among $C_{1-6}$ alkyl, $C_{1-6}$ alkoxy, and a halogen atom;

$Q^2$ is a hydrogen atom, a $C_{3-10}$ cycloalkyl optionally substituted by one or more $R^{10}$, a 5- to 10-membered heterocyclyl optionally substituted by one or more $R^{10}$, a $C_{6-10}$ aryl optionally substituted by one or more $R^{10}$, or a 5- to 10-membered heteroaryl optionally substituted by one or more $R^{10}$, where $R^{10}$ is independently selected from among $C_{1-6}$ alkyl, $C_{1-6}$ alkoxy, a halogen atom, and —$Z^3$—($C_{0-15}$ alkylene)-$Q^3$, $Q^3$ is a $C_{3-10}$ cycloalkyl optionally substituted by one or more $R^{11}$, a 5- to 10-membered heterocyclyl optionally substituted by one or more $R^{11}$, a $C_{6-10}$ aryl optionally substituted by one or more $R^{11}$, or a 5- to 10-membered heteroaryl optionally substituted by one or more $R^{11}$, where $R^{11}$ is independently selected from among $C_{1-6}$ alkyl, $C_{2-6}$ alkenyl, $C_{2-6}$ alkynyl, $C_{1-6}$ alkoxy, $C_{1-6}$ alkylsulfonyl, hydroxyl $C_{1-6}$ alkyl, $C_{7-14}$ aralkyl, $C_{1-6}$ alkoxy $C_{1-6}$ alkyl, $C_{3-10}$ cycloalkyl, 5- to 10-membered heterocyclyl, $C_{6-10}$ aryl, 5- to 10-membered heteroaryl, cyano, amino, nitro, trifluoromethyl, halogen atom, and hydroxy;

$Z^1$, $Z^2$ and $Z^3$ are independently selected from the group consisting of an oxygen atom, a sulfur atom, —$NR^7$—, —CO—, —$SO_2$—, difluoromethylene, and a direct bond, where $R^7$ is a hydrogen atom or $C_{1-6}$ alkyl, provided that in the case of —$Z^1$—($C_0$ alkylene)-$Z^2$—, either one of $Z^1$ and $Z^2$ is an oxygen atom and the other is a direct bond;

$R^2$ is a hydrogen atom, $C_{1-6}$ alkyl, $C_{7-14}$ aralkyl, or $C_{1-6}$ alkoxy $C_{1-6}$ alkyl;

$R^3$ is a hydrogen atom or $C_{1-6}$ alkyl;

$R^4$ and $R^5$ are independently selected from the group consisting of a hydrogen atom, $C_{1-6}$ alkyl, $C_{7-14}$ aralkyl, formyl, $C_{1-6}$ alkylcarbonyl, $C_{6-10}$ arylcarbonyl, $C_{1-6}$ alkoxycarbonyl, $C_{1-6}$ alkoxy $C_{1-6}$ alkyl, and $C_{7-14}$ aralkyloxycarbonyl;

$R^6$ is a hydrogen atom, $C_{1-6}$ alkyl, $C_{1-6}$ alkoxy $C_{1-6}$ alkyl, or $C_{7-14}$ aralkyl;

A is phenylene or ethynylene;

X and Y are independently $CH_2$ or a direct bond, or a salt thereof.

(2) The compound as recited in (1), which is represented by formula (IA):

[Formula 2]

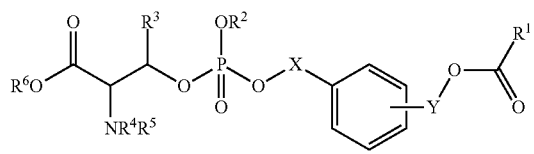

Formula (IA)

wherein $R^1$, $R^2$, $R^3$, $R^4$, $R^5$, $R^6$, X, and Y are as defined in (1), or a salt thereof.

(3) The compound as recited in (1), which is represented by formula (IB):

[Formula 3]

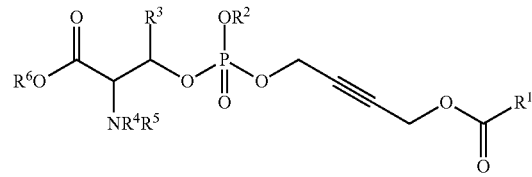

Formula (IB)

wherein $R^1$, $R^2$, $R^3$, $R^4$, $R^5$, and $R^6$ are as defined in (1), or a salt thereof.

(4) The compound as recited in any of (1) to (3), wherein $R^3$ is a hydrogen atom or methyl, or a salt thereof.

(5) The compound as recited in any of (1) to (4), wherein:

$R^2$ is a hydrogen atom;

$R^4$ and $R^5$ are each a hydrogen atom; and $R^6$ is a hydrogen atom, or a salt thereof.

(6) The compound as recited in any of (1) to (7), wherein $R^1$ is selected from among the following formulas:

[Formula 4]

 Formula (IIa)

 Formula (IIb)

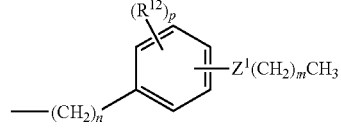

Formula (IIc)

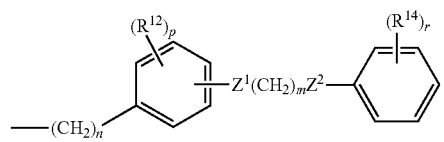

Formula (IId)

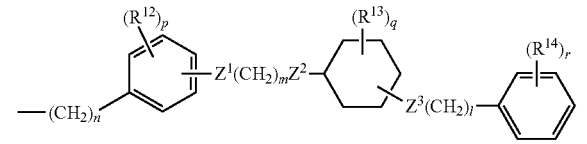

Formula (IIe)

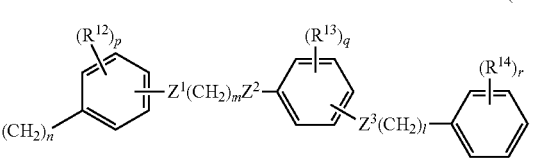

-continued

Formula (IIf)

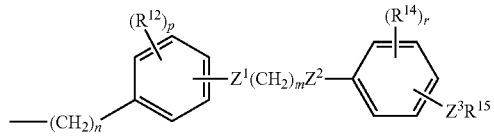

wherein:
R$^{12}$ and R$^{13}$ are independently selected from among C$_{1-6}$ alkyl, C$_{1-6}$ alkoxy, and a halogen atom,
R$^{14}$ is independently selected from among C$_{1-6}$ alkyl, C$_{2-6}$ alkenyl, C$_{2-6}$alkynyl, C$_{1-6}$ alkoxy, C$_{1-6}$ alkylsulfonyl, hydroxyl C$_{1-6}$ alkyl, C$_{7-14}$ aralkyl, C$_{1-6}$ alkoxy C$_{1-6}$ alkyl, C$_{3-10}$ cycloalkyl, 5- to 10-membered heterocyclyl, C$_{6-10}$ aryl, 5- to 10-membered heteroaryl, cyano, amino, nitro, trifluoromethyl, a halogen atom, and hydroxy,
R$^{15}$ is selected from among C$_{3-15}$ alkyl, C$_{3-10}$ cycloalkyl, and 5- to 10-membered heterocyclyl,
l and m are independently 0 to 15,
n is 0 to 15,
Z$^1$ and Z$^2$ are such that in the case where m is 0 or 1, either one of them is an oxygen atom while the other is a direct bond or both of them are direct bonds, and in the case where m is 2 to 15, Z$^1$ and Z$^2$ are independently selected from the group consisting of an oxygen atom and a direct bond,
Z$^3$ is independently selected from the group consisting of an oxygen atom, a sulfur atom, —NR$^7$—, —CO—, —SO$_2$—, difluoromethylene, and a direct bond, where R$^7$ is a hydrogen atom or C$_{1-6}$ alkyl,
p and q are independently 0 to 4,
r is 0 to 5 in the case of formulas (IIe) to (IIe), and 0 to 4 in the case of formula (IIf),
or a salt thereof.
(7) The compound as recited in (6), wherein R$^{14}$ is independently selected from among C$_{1-6}$ alkyl, C$_{1-6}$ alkoxy, C$_{6-10}$ aryl, C$_{6-10}$ aryloxy, and a halogen atom, or a salt thereof.
(8) A compound selected from:
O-(hydroxy(2-((3-(2-(undecyloxy)phenyl)propanoyl)oxy) phenoxy)phosphoryl)-L-serine;
O-(hydroxy(3-((3-(2-(undecyloxy)phenyl)propanoyl)oxy) phenoxy)phosphoryl)-L-serine;
O-(hydroxy(4-((3-(2-(undecyloxy)phenyl)propanoyl)oxy) phenoxy)phosphoryl)-L-serine;
O-(hydroxy(2-((3-(2-(undecyloxy)phenyl)propanoyl)oxy) methyl)phenoxy)phosphoryl)-L-serine;
O-(hydroxy(2-(((3-(2-((3-phenoxybenzyl)oxy)phenyl)propanoyl)oxy)methyl)phenoxy)phosphoryl)-L-serine;
O-(hydroxy(3-(((3-(2-(undecyloxy)phenyl)propanoyl)oxy) methyl)phenoxy)phosphoryl)-L-serine;
O-(hydroxy(3-(((3-(2-((3-phenoxybenzyl)oxy)phenyl)propanoyl)oxy)methyl)phenoxy)phosphoryl)-L-serine;
O-(hydroxy(4-(((3-(2-(undecyloxy)phenyl)propanoyl)oxy) methyl)phenoxy)phosphoryl)-L-serine;
O-(hydroxy((3-((3-(2-(undecyloxy)phenyl)propanoyl)oxy) benzyl)oxy)phosphoryl)-L-serine;
O-(hydroxy((3-((3-(2-((3-phenoxybenzyl)oxy)phenyl)propanoyl)oxy)benzyl)oxy)phosphoryl)-L-serine;
O-(hydroxy((4-((3-(2-(undecyloxy)phenyl)propanoyl)oxy) benzyl)oxy)phosphoryl)-L-serine;
O-(hydroxy((4-((3-(2-(undecyloxy)phenyl)propanoyl)oxy) but-2-yn-1-yl)oxy)phosphoryl)-L-serine;
O-(hydroxy(4-(((3-(2-((3-phenoxybenzyl)oxy)phenyl)propanoyl)oxy)methyl)phenoxy)phosphoryl)-L-serine; and
O-(hydroxy((3-(((3-(2-(undecyloxy)phenyl)propanoyl)oxy) methyl)benzyl)oxy)phosphoryl)-L-serine,
or a salt thereof.
(9) A pharmaceutical composition for treating autoimmune disease, comprising the compound or salt thereof as recited in any of (1) to (8).
(10). A lysophosphatidylserine receptor function modulator, comprising the compound or salt thereof as recited in any of (1) to (8) which acts on any one or more lysophosphatidylserine receptors selected from among GPR34, P2Y10, and GPR174.
(11) The lysophosphatidylserine receptor function modulator as recited in (10), which acts on any two lysophosphatidylserine receptors selected from among GPR34, P2Y10, and GPR174.
(12) The lysophosphatidylserine receptor function modulator as recited in (10), which selectively acts on P2Y10.
(13) The lysophosphatidylserine receptor function modulator as recited in any of (10) to (12), which has a lysophosphatidylserine receptor agonistic activity.
(14) A compound represented by formula (IV):

[Formula 5]

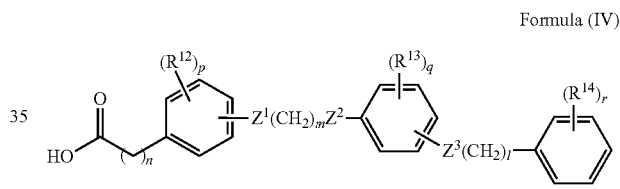

Formula (IV)

wherein:
R$^{12}$ and R$^{13}$ are independently selected from among C$_{1-6}$ alkyl, C$_{1-6}$ alkoxy, and a halogen atom;
R$^{14}$ is independently selected from among C$_{1-6}$ alkyl, C$_{2-6}$ alkenyl, C$_{2-6}$ alkynyl, C$_{1-6}$ alkoxy, C$_{1-6}$ alkylsulfonyl, hydroxyl C$_{1-6}$ alkyl, C$_{7-14}$ aralkyl, C$_{1-6}$ alkoxy C$_{1-6}$ alkyl, C$_{3-10}$ cycloalkyl, 5- to 10-membered heterocyclyl, C$_{6-10}$ aryl, 5- to 10-membered heteroaryl, cyano, amino, nitro, trifluoromethyl, a halogen atom, and hydroxy;
p and q are independently 0 to 4;
r is 0 to 5;
l and m are independently 0 to 3;
n is 0 to 5;
Z$^1$ and Z$^2$ are such that in the case where m is 0 or 1, either one of them is an oxygen atom while the other is a direct bond or both of them are direct bonds and Z$^1$ and Z$^2$ are independently selected from the group consisting of an oxygen atom and a direct bond;
Z$^3$ is selected from the group consisting of an oxygen atom, a sulfur atom, —NR$^{16}$—, —CO—, —SO$_2$—, difluoromethylene, and a direct bond, where R$^{16}$ is a hydrogen atom or C$_{1-6}$ alkyl,
or a salt thereof.

(27) A compound represented by formula (V):

[Formula 6]

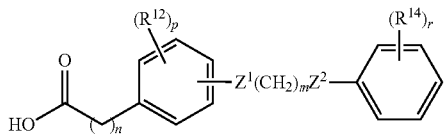

Formula (V)

wherein:
$R^{12}$ is independently selected from among $C_{1-6}$ alkyl, $C_{1-6}$ alkoxy, and a halogen atom;
$R^{14}$ is independently selected from among $C_{1-6}$ alkyl, $C_{2-6}$ alkenyl, $C_{2-6}$ alkynyl, $C_{1-6}$ alkoxy, $C_{1-6}$ alkylsulfonyl, hydroxy $C_{1-6}$ alkyl, $C_{7-14}$ aralkyl, $C_{1-6}$ alkoxy $C_{1-6}$ alkyl, $C_{3-10}$ cycloalkyl, 5- to 10-membered heterocyclyl, $C_{6-10}$ aryl, 5- to 10-membered heteroaryl, $C_{6-10}$ aryloxy, 5- to 10-membered heteroaryloxy, cyano, amino, nitro, trifluoromethyl, a halogen atom, and hydroxy;
p is 0 to 4;
r is 0 to 5;
m is 3 to 15;
n is 0 to 5;
$Z^1$ and $Z^2$ are independently selected from the group consisting of an oxygen atom and a direct bond,
or a salt thereof.

(28) A compound represented by formula (VI):

[Formula 7]

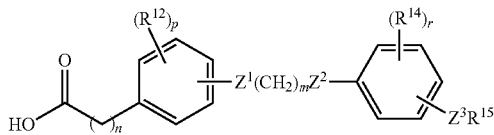

Formula (IV)

wherein:
$R^{12}$ is independently selected from among $C_{1-6}$ alkyl, $C_{1-6}$ alkoxy, and a halogen atom;
$R^{14}$ is independently selected from among $C_{1-6}$ alkyl, $C_{2-6}$ alkenyl, $C_{2-6}$ alkynyl, $C_{1-6}$ alkoxy, $C_{1-6}$ alkylsulfonyl, hydroxy $C_{1-6}$ alkyl, $C_{7-14}$ aralkyl, $C_{1-6}$ alkoxy $C_{1-6}$ alkyl, $C_{3-10}$ cycloalkyl, 5- to 10-membered heterocyclyl, $C_{6-10}$ aryl, 5- to 10-membered heteroaryl, $C_{6-10}$ aryloxy, 5- to 10-membered heteroaryloxy, cyano, amino, nitro, trifluoromethyl, a halogen atom, and hydroxy;
p and r are independently 0 to 4;
m is independently 0 to 3;
n is 0 to 5;
$Z^1$ and $Z^2$ are such that in the case where m is 0 or 1, either one of them is an oxygen atom while the other is a direct bond or both of them are direct bonds, and in the case where m is 2 or 3, $Z^1$ and $Z^2$ are independently selected from the group consisting of an oxygen atom and a direct bond;
$Z^3$ is selected from the group consisting of an oxygen atom, a sulfur atom, —$NR^{16}$—, —CO—, —$SO_2$—, difluoromethylene, and a direct bond, where $R^{16}$ is a hydrogen atom or $C_{1-6}$ alkyl;
$R^{15}$ is selected from among $C_{3-15}$ alkyl, $C_{3-10}$ cycloalkyl, and 5- to 10-membered heterocyclyl,
or a salt thereof.

Advantageous Effects of Invention

According to the present invention, lysophosphatidylserine derivatives or salts thereof are provided, and in addition, pharmaceutical compositions or lysophosphatidylserine receptor function modulators that comprise those compounds or salts thereof are also provided.

DESCRIPTION OF EMBODIMENTS

Hereinafter, the present invention is described more specifically.

Compounds or Salts Thereof

The compounds of the present invention or salts thereof include the compounds of formulas (I), (IA), (IB), and (Ia) to (Id) set forth above or salts thereof, more specifically the compounds described in the Examples given later.

As one embodiment of the present invention, compounds represented by the following formula (I) or salts thereof are given:

[Formula 8]

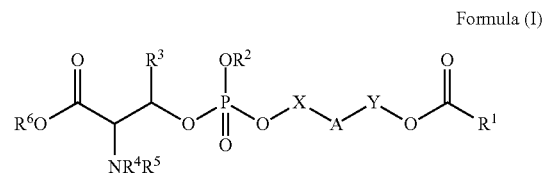

Formula (I)

wherein $R^1$ to $R^6$, A, X and Y are as defined above.
For example, $R^1$ may be selected from among the following formulas:

[Formula 9]

Formula (IIa)

Formula (IIb)

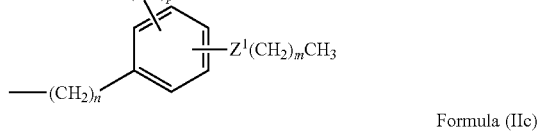

Formula (IIc)

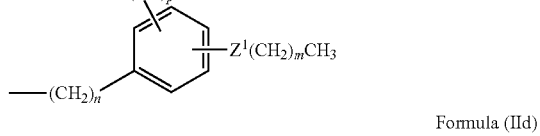

Formula (IId)

-continued

Formula (IIe)

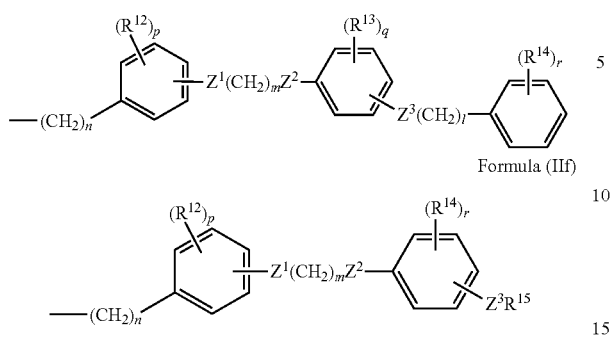

Formula (IIf)

wherein $R^{12}$, $R^{13}$, $R^{14}$, p, q, r, l, m, n, $Z^1$, $Z^2$, and $Z^3$ are as defined above and may include (8Z)-8-heptadecenyl, 2-(2-undecyloxyphenyl)ethyl, 2-[2-(3-phenoxybenzyloxy)phenyl]ethyl, etc.;

provided that in the case of formula (IIa), for example, n and m, taken independently, are preferably 6 to 8, more preferably 7;

in the case of formula (IIb), n is preferably 1 to 3, more preferably 2, and m is preferably 8 to 12, more preferably 10;

in the case of formula (IIc), n is preferably 1 to 3, more preferably 2, and m is preferably 3 to 15, more preferably 3 to 10, more preferably 3 to 8, even more preferably 4 to 6;

in the case of formula (IIe), n is preferably 1 to 3, more preferably 2, m is preferably 0 to 3, more preferably 1, l is preferably 0 to 3, more preferably 0, and $Z^3(CH_2)_l$ is preferably selected from the group consisting of an oxygen atom, —NH—, —$CH_2$—, —$OCH_2$—, and a direct bond;

in the case of formula (IIf), n is preferably 1 to 3, more preferably 2, m is preferably 0 to 3, more preferably 1, l is preferably 0 to 3, more preferably 0, and $R^{15}$ is preferably $C_{3-10}$ alkyl, more preferably $C_{3-8}$ alkyl, even more preferably $C_{4-6}$ alkyl;

where $Z^1$ and $Z^2$ are such that in the case where m is 0 or 1, either one of them is an oxygen atom while the other is a direct bond or both of them are direct bonds, and in the case where m is 2 or 3, $Z^1$ and $Z^2$ are independently selected from the group consisting of an oxygen atom and a direct bond;

the groups that substitute the rings included in formulas (IIa) to (If) may provide any of ortho, meta, and para forms.

As a more preferred embodiment of the present invention, compounds represented by the following formula (IA) or salts thereof may be given:

[Formula 10]

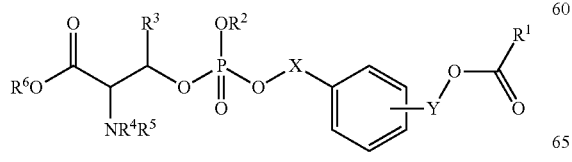

Formula (IA)

The compounds of formula IA include the following ortho, meta, and para substituted forms.

[Formula 11]

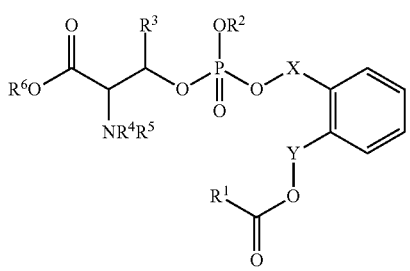

Ortho form

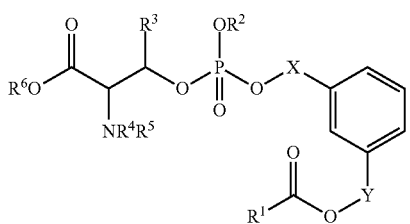

Meta form

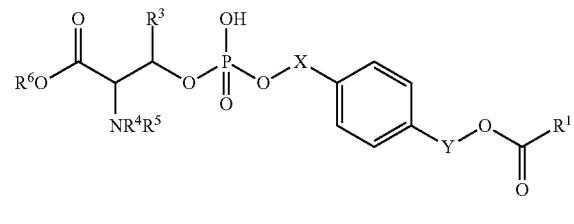

Para form wherein $R^1$ to $R^6$, X and Y are as defined above.

As a more preferred embodiment of the present invention, compounds represented by the following formulas (Ia), (Ib), (Ic) and (Id) or salts thereof may be given:

[Formula 12]

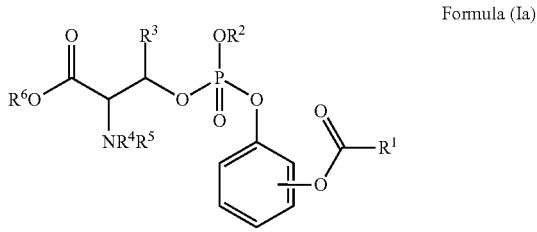

Formula (Ia)

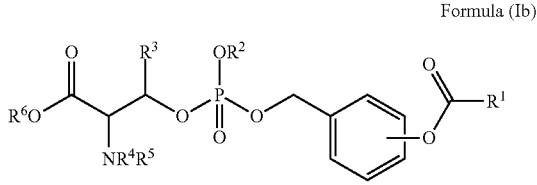

Formula (Ib)

Formula (Ic)

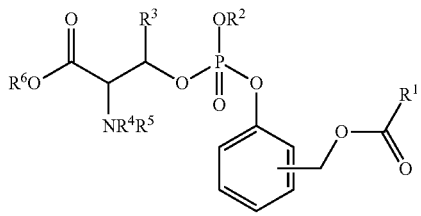

Formula (Id)

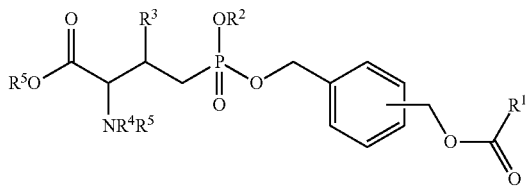

wherein $R^1$ to $R^6$ are as defined above. The compounds of formulas (Ia) to (Id) each include ortho, meta, and para substituted forms.

As another embodiment of the present invention, compounds represented by the following formula (IB) or salts thereof may be given:

[Formula 13]

Formula (IB)

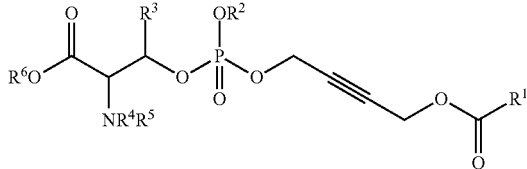

wherein $R^1$ to $R^6$ are as defined above.

As the most preferred embodiment of the present invention, the compounds shown in the following Tables 1-1 and 1-2 or salts thereof are given:

TABLE 1-1

| Compound No. | Structural formula | Compound name |
|---|---|---|
| 1 | | O-(hydroxy(2-((3-(2-(undecyloxy)phenyl)propanoyl)oxy)phenoxy)phosphoryl)-L-serine |
| 2 | | O-(hydroxy(3-((3-(2-(undecyloxy)phenyl)propanoyl)oxy)phenoxy)phosphoryl)-L-serine |
| 3 | | O-(hydroxy(4-((3-(2-(undecyloxy)phenyl)propanoyl)oxy)phenoxy)phosphoryl)-L-serine |
| 4 | | O-(hydroxy(2-(((3-(2-(undecyloxy)phenyl)propanoyl)oxy)methyl)phenoxy)phosphoryl)-L-serine |

TABLE 1-1-continued

| Compound No. | Structural formula | Compound name |
|---|---|---|
| 5 | | O-(hydroxy(2-(((3-(2-((3-phenoxybenzyl)oxy)phenyl)propanoyl)oxy)methyl)phenoxy)phosphoryl)-L-serine |
| 6 | | O-(hydroxy(3-(((3-(2-(undecyloxy)phenyl)propanoyl)oxy)methyl)phenoxy)phosphoryl)-L-serine |
| 7 | | O-(hydroxy(3-(((3-(2-((3-phenoxybenzyl)oxy)phenyl)propanoyl)oxy)methyl)phenoxy)phosphoryl)-L-serine |

TABLE 1-2

| Compound No. | Structural formula | Compound name |
|---|---|---|
| 8 | | O-(hydroxy(4-(((3-(2-(undecyloxy)phenyl)propanoyl)oxy)methyl)phenoxy)phosphoryl)-L-serine |
| 9 | | O-(hydroxy((3-((3-(2-(undecyloxy)phenyl)propanoyl)oxy)benzyl)oxy)phosphoryl)-L-serine |

TABLE 1-2-continued

| Compound No. | Structural formula | Compound name |
|---|---|---|
| 10 | | O-(hydroxy((3-((3-(2-((3-phenoxybenzyl)oxy)phenyl)propanoyl)oxy)benzyl)oxy)phosphoryl)-L-serine |
| 11 | | O-(hydroxy((4-(3-(2-(undecyloxy)phenyl)propanoyl)oxy)benzyl)oxy)phosphoryl)-L-serine |
| 12 | | O-(hydroxy((4-((3-(2-(undecyloxy)phenyl)propanoyl)oxy)but-2-yn-1-yl)oxy)phosphoryl)-L-serine |
| 16 | | O-(hydroxy(4-(((3-(2-((3-phenoxybenzyl)oxy)phenyl)propanoyl)oxy)methyl)phenoxy)phosphoryl)-L-serine |
| 17 | | O-(hydroxy((3-(((3-(2-(undecyloxy)phenyl)propanoyl)oxy)methyl)benzyl)oxy)phosphoryl)-L-serine |

As other embodiments of the present invention, the intermediate compounds shown in the following Tables 2-1 to 2-4 or salts thereof may be given:

TABLE 2-1

| Compound No. | Structural formula | Compound name |
|---|---|---|
| 30 | 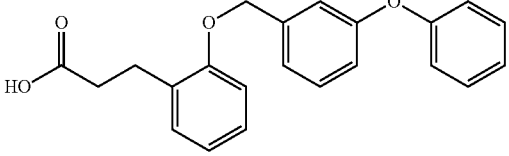 | 3-(2-((3-phenoxybenzyl)oxy)phenyl)propanoic acid |
| 31 | 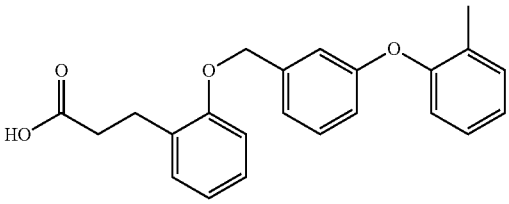 | 3-(2-((3-(o-tolyloxy)benzyl)oxy)phenyl)propanoic acid |
| 32 | 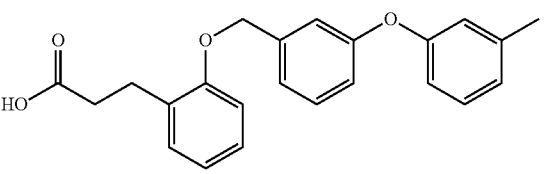 | 3-(2-((3-(m-tolyloxy)benzyl)oxy)phenyl)propanoic acid |
| 33 | 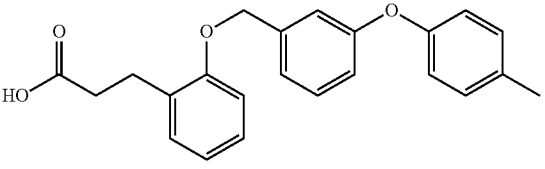 | 3-(2-((3-(p-tolyloxy)benzyl)oxy)phenyl)propanoic acid |
| 34 | 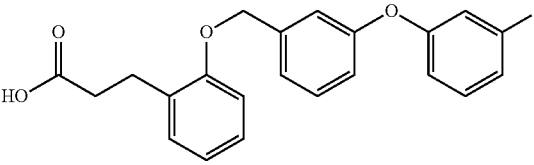 | 3-(2-((3-(3-chlorophenoxy)benzyl)oxy)phenyl)propanoic acid |
| 35 | 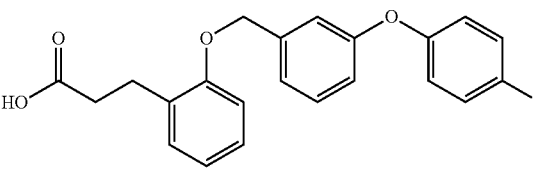 | 3-(2-((3-(4-chlorophenoxy)benzyl)oxy)phenyl)propanoic acid |
| 36 | 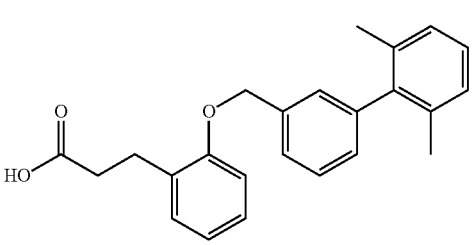 | 3-(2-((2'-6'-dimethyl-[1,1'-biphenyl]-3-yl)methoxy)phenyl)propanoic acid |

TABLE 2-1-continued

| Compound No. | Structural formula | Compound name |
|---|---|---|
| 37 | | 3-(3-((2',6'-dimethyl-[1,1'-biphenyl]-3-yl)methoxy)phenyl)propanoic acid |
| 38 | | 3-(2-((3-(3,4-dichlorophenoxy)benzyl)oxy)phenyl)propanoic acid |

TABLE 2-2

| Compound No. | Structural formula | Compound name |
|---|---|---|
| 39 | | 3-(2-((3-(2-fluorophenoxy)benzyl)oxy)phenyl)propanoic acid |
| 40 | | 3-(2-((3-(4-bromophenoxy)benzyl)oxy)phenyl)propanoic acid |
| 41 | | 3-(2-((3-(4-iodophenoxy)benzyl)oxy)phenyl)propanoic acid |
| 42 | | 3-(2-((3-(4-(tert-butyl)phenoxy)benzyl)oxy)phenyl)propanoic acid |
| 43 | | 3-(2-((3-([1,1'-biphenyl]-4-yloxy)benzyl)oxy)phenyl)propanoic acid |

TABLE 2-2-continued

| Compound No. | Structural formula | Compound name |
|---|---|---|
| 44 | | 3-(2-((3-(4-methoxyphenoxy)benzyl)oxy)phenyl)propanoic acid |
| 45 | | 3-(2-((3-benzylbenzyl)oxy)phenyl)propanoic acid |
| 46 | | 3-(2-((3-(benzyloxy)benzyl)oxy)phenyl)propanoic acid |

TABLE 2-3

| Compound No. | Structural formula | Compound name |
|---|---|---|
| 47 | | 3-(2-([1,1'-biphenyl]-3-ylmethoxy)phenyl)propanoic acid |
| 48 | | 3-(3-([1,1'-biphenyl]-3-ylmethoxy)phenyl)propanoic acid |
| 49 | | 3-(2-((3-(phenylamino)benzyl)oxy)phenyl)propanoic acid |
| 50 | | 3-(3-((3-phenoxyphenoxy)methyl)phenyl)propanoic acid |

TABLE 2-4

| Compound No. | Structural formula | Compound name |
|---|---|---|
| 51 | | 3-(2-(4-phenoxybutoxy)phenyl)propanoic acid |
| 52 | | 3-(2-((6-phenoxyhexyl)oxy)phenyl)propanoic acid |
| 53 | | 3-(3-(4-phenoxybutoxy)phenyl)propanoic acid |
| 54 | | 3-(3-((6-phenoxyhexyl)oxy)phenyl)propanoic acid |
| 59 | | 3-(2-((3-(hexyloxy)benzyl)oxy)phenyl)propanoic acid |
| 60 | | 3-(3-((3-(hexyloxy)benzyl)oxy)phenyl)propanoic acid |

As used herein, the term "$C_{1-6}$ alkyl" means a straight-chain, branched-chain, cyclic or partially cyclic alkyl group having 1 to 6 carbon atoms and may include methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl, as well as cyclopropyl, cyclobutyl, cyclopentyl, cyclohexyl, and cyclopropylmethyl, with $C_{1-4}$ alkyl and $C_{1-3}$ alkyl, for example, being also included.

As used herein, the term "$C_{1-30}$ alkyl" means a straight-chain, branched-chain, cyclic or partially cyclic alkyl group having 1 to 30 carbon atoms and may, aside from the $C_{1-6}$ alkyl groups already given as exemplary $C_{1-6}$ alkyls, include straight-chain, branched-chain, cyclic or partially cyclic alkyl groups that are represented by $C_7H_{15}$, $C_8H_{17}$, $C_9H_{19}$, $C_{10}H_{21}$, $C_{11}H_{23}$, $C_{12}H_{25}$, $C_{13}H_{27}$, $C_{14}H_{29}$, $C_{15}H_{31}$, $C_{16}H_{33}$, $C_{17}H_{35}$, $C_{18}H_{37}$, $C_{19}H_{39}$, $C_{20}H_{41}$, $C_{21}H_{43}$, $C_{22}H_{45}$, $C_{23}H_{47}$, $C_{24}H_{49}$, $C_{25}H_{51}$, $C_{26}H_{53}$, $C_{27}H_{55}$, $C_{28}H_{57}$, $C_{29}H_{59}$, and $C_{30}H_{61}$.

As used herein, the term "$C_{0-15}$ alkylene" means a divalent group formed from a straight- or branched-chain $C_{0-15}$ alkane to have two linkage sites. This group may include a group represented by the formula —$(CH_2)_q$— (wherein q is 0 to 15), and ($C_0$ alkylene) means a direct bond.

As used herein, the term "$C_{1-6}$ alkylcarbonyl" means an alkylcarbonyl group having the already defined $C_{1-6}$ alkyl group as the alkyl moiety and may include $C_{1-4}$ alkylcarbonyl as exemplified by methylcarbonyl (acetyl), ethylcarbonyl, and tert-butylcarbonyl.

As used herein, the term "$C_{1-6}$ alkylsulfonyl" means a group consisting of a sulfonyl group to which the already defined $C_{1-6}$ alkyl group is attached as the alkyl moiety and may include methylsulfonyl, ethylsulfonyl, propylsulfonyl, isopropylsulfonyl, tert-butylsulfonyl, isobutylsulfonyl, sec-butylsulfonyl, etc.

The term "hydroxy $C_{1-6}$ alkyl" means a group in which one or more hydroxy groups have replaced the hydrogen atom(s) attached to the carbon atom(s) in the $C_{1-6}$ alkyl group already defined as the alkyl moiety and may include hydroxymethyl, 1-hydroxyethyl, 2-hydroxyethyl, 1-hydroxypropyl, 2-hydroxylpropyl, 1,2-hydroxyethyl, etc.

As used herein, the term "$C_{1-6}$ alkoxy" means an alkyloxy group that has the already defined alkyl group of 1 to 6 carbon atoms as the alkyl moiety and may include methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, cyclopentyloxy, cyclohexyloxy, cyclopropylmethyloxy, etc., with $C_{1-4}$ alkoxy and $C_{1-3}$ alkoxy, for example, being also included. The term "$C_{1-4}$ alkoxy" as used herein also includes $C_{1-3}$ alkoxy, for example.

As used herein, the term "$C_{1-6}$ alkoxycarbonyl" means an alkoxycarbonyl group having the already defined $C_{1-6}$ alkoxy group as the alkoxy moiety and may include $C_{1-3}$ alkoxycarbonyl as exemplified by methoxycarbonyl, ethoxycarbonyl, and tert-butoxycarbonyl.

As used herein, the term "$C_{1-6}$ alkoxy $C_{1-6}$ alkyl" may include methoxymethyl, ethoxymethyl, 2-methoxyethyl, 1-methoxyethyl, etc.

As used herein, the term "$C_{2-30}$ alkenyl" encompasses straight- or branched-chain alkenyl groups of carbon numbers 2 to 30 with one double bond therein (as exemplified by 8-heptadecenyl). The term further encompasses straight- or branched-chain alkenyl groups with two double bonds therein (as exemplified by 9,12-odctadecadienyl), straight- or branched-chain alkenyl groups with three double bonds therein (as exemplified by 9,12,15-octadecatrienyl), straight- or branched-chain alkenyl groups with four double bonds therein (as exemplified by 5,8,11,14-eicosatetraenyl), and straight- or branched-chain alkenyl groups with five or more double bonds therein. The term "$C_{2-30}$ alkenyl" as used herein also encompasses $C_{2-6}$ alkenyl, for example.

As used herein, the term "$C_{2-30}$ alkynyl" means straight- or branched-chain alkenyl groups of carbon numbers 2 to 30, encompassing straight- or branched-chain alkynyl groups with one triple bond therein and straight- or branched-chain alkynyl groups with two or more triple bonds therein. The term "$C_{2-30}$ alkynyl" as used herein may also encompass $C_{2-6}$ alkynyl, for example.

As used herein, the term "$C_{3-10}$ cycloalkyl" means cyclic alkyl groups having 3 to 10 carbon atoms and may encompass cyclopropyl, cyclobutyl, cyclopentyl, cyclohexyl, etc. Note that the $C_{3-10}$ cycloalkyl is included in the scope of the meaning of the $C_{1-30}$ alkyl defined above.

As used herein, the term "$C_{3-10}$ cycloalkylene" means a divalent group consisting of a saturated carbon ring of carbon numbers 3 to 10 that has two linkage sites.

As used herein, the term "5- to 10-membered heterocyclyl" means a saturated or partially saturated aliphatic heterocyclic group that contains one or more hetero atoms selected from among an oxygen atom, a nitrogen atom, and a sulfur atom and which has 5 to 10 ring atoms. Specific examples include oxetanyl, tetrahydropyranyl, tetrahydropyranyl, pyrrolidinyl, piperidinyl, piperazinyl, morpholinyl, tetrahydrothiopyranyl, etc.

As used herein, the term "5- to 10-membered heterocyclene" means a divalent group consisting of a 5- to 10-membered hetero ring having two linkage sites.

As used herein, the term "$C_{6-10}$ aryl" may be an aromatic carbocyclic group having 6 to 10 carbon atoms and may include phenyl, naphthyl, etc.

As used herein, the term "$C_{6-10}$ aryloxy" may include phenoxy, naphthyloxy, etc.

As used herein, the term "$C_{6-10}$ arylcarbonyl" may include benzoyl and so on.

As used herein, the term "$C_{6-10}$ arylene" means a divalent group consisting of a $C_{6-10}$ aromatic carbocycle having two linkage sites and in the case of a phenylene group, for example, the term encompasses 1,2-substituted (ortho-substituted), 1,3-substituted (meta-substituted), and 1,4-substituted (para-substituted) groups.

As used herein, the term "$C_{7-14}$ aralkyl" means an arylalkyl group having 7 to 14 carbon atoms with an aryl group therein and may include benzyl, 1-phenethyl, 2-phenethyl, 1-naphthylmethyl, 2-naphthylmethyl, etc. The carbon number of the alkyl moiety may be 1 to 4.

As used herein, the term "$C_{7-14}$ aralkyloxycarbonyl" may encompass benzyloxycarbonyl, 1-phenethyloxycarbonyl, 2-phenethyloxycarbonyl, 1-naphthylmethyloxycarbonyl, 2-naphthylmethyloxycarbonyl, etc.

As used herein, the term "5- to 10-membered heteroaryl" means an aromatic monoheterocyclic group with 5 to 10 ring atoms containing a hetero atom selected from among an oxygen atom, a nitrogen atom, and a sulfur atom. Specific examples include pyrrolyl, imidazolyl, pyrazolyl, triazolyl, pyridyl, pyrimidyl, pyridazinyl, furyl, thienyl, oxazolyl, oxadiazolyl, thiazolyl, thiadiazolyl, etc.

As used herein, the term "5- to 10-membered heteroaryloxy" may encompass pyrrolyloxy, imidazolyloxy, pyrazolyloxy, triazolyloxy, pyridyloxy, pyrimidyloxy, pyridazinyloxy, furyloxy, thienyloxy, oxazolyloxy, oxadiazolyloxy, thiazolyloxy, thiadiazolyloxy, etc.

As used herein, the term "5- to 10-membered heteroarylene" means a divalent group consisting of a 5- to 10-membered aromatic heterocycle having two linkage sites and may, in the case of a 6-membered heteroarylene group, encompass a group in which linkage occurs on adjacent ring atoms, a group in which the ring atom the second next to the ring atom having one linkage site has another linkage site, and a group in which the ring atom the third next to the ring atom having one linkage site has another linkage site. Specific examples of the heterocycle that constitutes such groups include pyrrole, imidazole, pyrazole, triazole, pyridine, pyrimidine, pyridazinine, furan, thiophene, oxazole, oxadiazole, thiazole, thidiazole, etc.

As used herein, the term "halogen atom" may encompass a chlorine atom, a fluorine atom, an iodine atom, etc.

Hereinafter, in the case where one or more bonds between carbon atoms are a double bond, the configuration may be cis or trans.

The present invention which relates to the compounds represented by formulas (I), (IA), (IB) and (Ia) to (Id) set forth above encompasses a variety of stereoisomers including tautomers, geometrical isomers, optical isomers, etc. and mixtures thereof.

Salts of the compounds of the present invention are not particularly limited as long as they are salts and those salts which can be used as pharmaceuticals are preferred. Salts the compounds of the present invention form with bases include salts with inorganic bases such as sodium, potassium, magnesium, calcium and aluminum, and salts with organic bases such as methylamine, ethylamine, and ethanolamine. The salts of interest may be acid addition salts which specifically include addition salts with: mineral acids such as hydrochloric acid, hydrobromic acid, hydroiodic acid, sulfuric acid, nitric acid, and phosphoric acid; and organic acids such as formic acid, acetic acid, trifluoroacetic acid, propionic acid, oxalic acid, malonic acid, succinic acid, fumaric acid, maleic acid, lactic acid, malic acid, tartaric acid, citric acid, methanesulfonic acid, and ethanesulfonic acid.

What is more, the compounds of the present invention also encompass hydrates, various solvates, crystal polymorph, and so on.

The atoms contained in the compounds of the present invention (e.g. hydrogen, carbon, oxygen, nitrogen, sulfur, and phosphorus atoms) may be the atoms of isomers other than those which are respectively the most abundant in nature, and such isomeric atoms may be radioconductive atoms. Briefly, according to one aspect of the present invention, the compounds of formulas (I), (IA), (IB) and (Ia) to (Id) already defined herein and which are labeled with isotopic atoms, or salts thereof are provided. Here, labeling with isotopic atoms may be labeling with radioisotopes (e.g. $^3$H, $^{14}$C, $^{32}$P) and, from the aspect of easy preparation of compounds, labeling with $^3$H is preferred. The $^3$H labeled compounds of the present invention can be synthesized by, for example, employing $^3$H labeled fatty acids or derivatives thereof.

In one mode of the present invention, the compounds of formulas (I), (IA) and (IB) as well as (Ia) to (Id) are administered as prodrugs and converted to active compounds in vivo. For example, $R^2$ and $R^6$ in formulas (I), (IA), (IB) and (Ia) to (Id) may be groups that form carboxylate esters or phosphate esters. Specific examples of such groups are cited in Journal of Medicinal Chemistry, 2008, 51(8), 2337 and include: $C_{1-6}$ alkyls (e.g. tert-butyl), $C_{1-6}$ alkoxy $C_{1-6}$ alkyls (e.g. methoxymethyl), $C_{1-6}$ alkylcarbonyloxy $C_{1-6}$ alkyls (e.g. pivaloyloxymethyl), $C_{1-6}$ alkoxycarbonyloxy $C_{1-6}$ alkyls (e.g. isopropoxycarbonyloxymethyl), optionally substituted phenyl (e.g. $C_{1-3}$ alkoxyphenyl), optionally substituted benzyl (e.g. benzyl optionally substituted by 1 to 3 groups selected from among $C_{1-6}$ alkoxy, hydroxy, $C_{1-6}$ alkylcarbonyloxy, nitro, and a halogen atom), phthalidyl (e.g. isobenzofuranon-3-yl optionally substituted by 1 to 4 groups selected from $C_{1-6}$ alkoxy), dioxolenonylmethyl (e.g. dioxolenon-4-ylmethyl the dioxolenone ring of which is optionally substituted at position 5 by a group selected from $C_{1-6}$ alkoxy or phenyl), or furylmethyl (e.g. 2-furylmethyl the furan ring of which is optionally substituted by nitro at position 5).

Synthesis of Compounds or Salts Thereof

Since lysophosphatidylserine receptors are module-type compounds each consisting of hydrophilic sites (amino acid site and phosphate diester site), a hydrophobic site (acyl side chain site), and a linkage site for linking the hydrophilic sites to the hydrophobic site, the compounds of the present invention and salts thereof can be synthesized by systematically converting the respective modular structures in accordance with the general synthesis processes set out below. The compounds of formulas (I), (IA), (IB), and (Ia) to (Id) can, for example, be synthesized by the steps shown in the following schemes.

[Formula 14]

SCHEME 1: General Synthesis Process for Acetylene Compound (Formula IB)

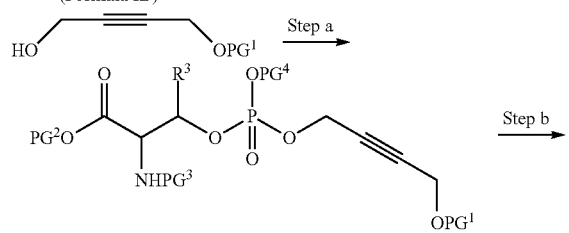

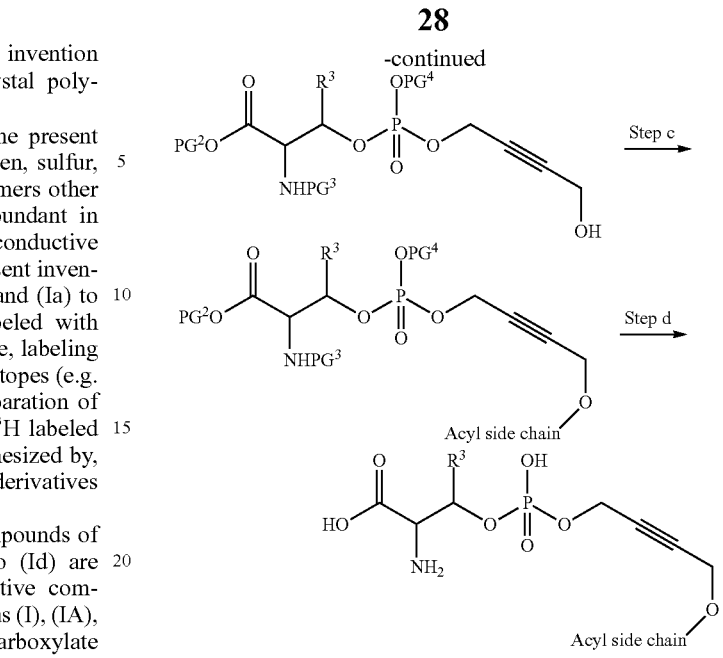

[wherein $R^3$ is as already defined herein; —O— acyl side chain corresponds to —O—CO—$R^1$ in formula (IB) already defined herein; $PG^1$, $PG^2$, $PG^3$ and $PG^4$ each represent a protective group, as exemplified by such cases that $PG^1$, $PG^2$ and $PG^4$ are tert-butyldimethylsilyl (TBS) or tert-butyl whereas $PG^3$ is tert-butoxycarbonyl (Boc)].

The compounds encompassed by formula (IB) can, for example, be prepared by the following procedure: in step a, one primary alcohol at the linkage site (1,4-butynediol) and phosphoramidite are condensed and oxidized, followed by deprotection of the alcohol in step b, condensation with the acyl side chain site in step c, and subsequent deprotection of phosphoric acid, carboxylic acid and amine in step d.

Condensation reaction in step a may, for example, use an active derivative of phosphoric acid as well as a suitable condensing agent. The reaction can also be performed in a suitable solvent such as methylene chloride, tetrahydrofuran, N,N'-dimethylformamide, toluene, diethyl ether or 1,4-dioxane in the presence of a suitable reaction promoter (e.g. 1H-tetrazole). The oxidation step may be performed in a suitable solvent using a suitable oxidizing agent (e.g. tert-butylhydroperoxide, metachloroperbenzoic acid, iodine-pyridine-water). The condensation and oxidation steps may be performed on the product obtained by post-treatment after the condensation reaction; alternatively, they may be implemented as one-pot reaction without post-treatment.

The deprotection in step b may be performed by subjecting the reaction mixture to appropriate deprotection conditions, such as by using trifluoroacetic acid (TFA).

The acylation of alcohol in step c may involve preparation using an acid chloride; in this case, the reaction may be carried out in a suitable solvent in the presence of a suitable base (e.g. 4-dimethylaminopyridine) or in the absence of any base. Acylation can also be performed using a carboxylic acid and a suitable condensing agent (e.g. 1-ethyl-3-(3-dimethylaminopropyl)carbodiimide hydrochloride (EDC), 1,3-diisopropylcarbodiimide (DIC), etc.)

In the deprotection in step d, the reaction mixture may be subjected to the same deprotection conditions as in step b and/or further conversion of substituents may be performed to thereby obtain the desired compounds encompassed by formula (IB).

Although not being particularly limited, these steps may be performed at reaction temperatures of, for example, 0 to 70° C., preferably 15 to 30° C., and for reaction periods of, for example, 10 minutes to 2 days, preferably 1 to 2 hours.

[Formula 15]

SCHEME 2-1: General Synthesis Process 1 for Benzene Ring Compound (Formula Ia)

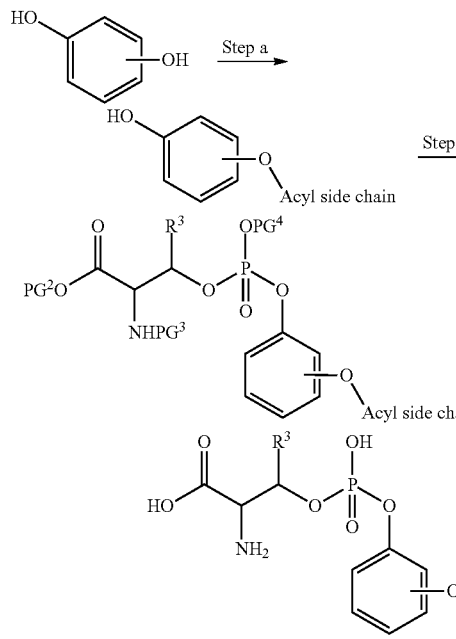

[wherein $R^3$ is as already defined herein; —O— acyl side chain corresponds to —O—CO—$R^1$ in formula (Ia) already defined herein; $PG^2$, $PG^3$ and $PG^4$ respectively mean protective groups, as defined in above Scheme 1].

The compounds encompassed by formula (Ia) can, for example, be prepared by the following procedure: in step a, one of the two hydroxy groups as substituents on the benzene ring is condensed with the acyl side chain site and in step b, further condensation is performed between the remaining hydroxy group as a substituent on the benzene ring and phosphoramidite, followed by oxidation; further in addition, deprotection such as of phosphoric acid, carboxylic acid and amine is performed in step c. The respective reactions in steps a to c can be performed under the same conditions as in the condensation, oxidation and deprotection reactions in Scheme 1.

[Formula 16]

SCHEME 2-2: General Synthesis Process 2 for Benzene Ring Compounds (Formulas Ib, Ic)

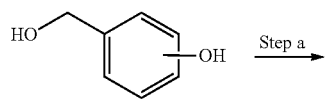

-continued

[wherein $R^3$ is as already defined herein; —O-acyl side chain corresponds to —O—CO—$R^1$ in formulas (Ib) and (Ic) already defined herein; $PG^2$, $PG^3$ and $PG^4$ respectively mean protective groups, as defined in above Scheme 1].

The compounds encompassed by formulas (Ib) and (Ic) can, for example, be prepared by the following procedure: in step a, one of the two hydroxy or hydroxymethyl groups as substituents on the benzene ring is condensed with the acyl side chain site and in steps b and b', further condensation is performed between the remaining hydroxy group and phosphoramidite, followed by oxidation; further in addition, deprotection such as of phosphoric acid, carboxylic acid and amine is performed in steps c and c'. The respective reactions in step a, steps b and b', as well as steps c and c' can be performed under the same conditions as in the condensation, oxidation and deprotection reactions in Scheme 1.

[Formula 17]

SCHEME 2-3: General Synthesis Process 3 for Benzene Ring Compound (Formula Ib)

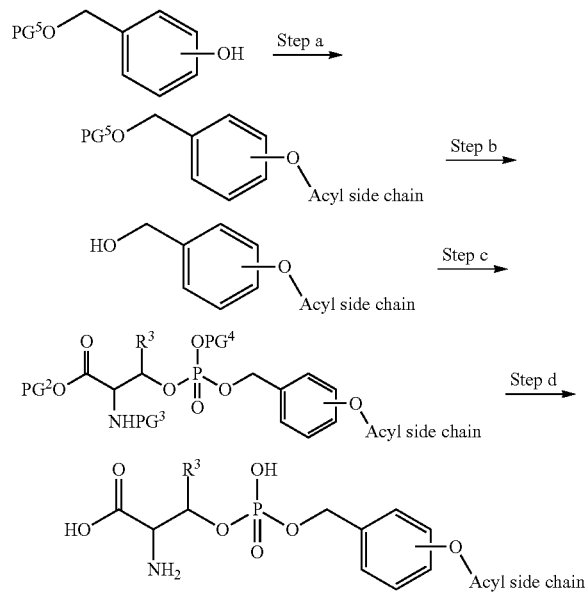

[wherein $R^3$ is as already defined herein; —O-acyl side chain corresponds to —O—CO—$R^1$ in formula (Ib) already defined herein; $PG^2$, $PG^3$ and $PG^4$ are as defined in above Scheme 1; $PG^5$ means a protective group such as TBS or tert-butyl].

The compounds encompassed by formula (Ib) can, for example, be prepared by the following procedure: in step a, the hydroxy group as a substituent on the benzene ring is condensed with the acyl side chain site; in step b, the alcohol is deprotected; in step c, further condensation is performed between the alcohol of the hydroxymethyl group as a substituent on the benzene ring and phosphoramidite, followed by oxidation; in step d, deprotection such as of phosphoric acid, carboxylic acid and amine is performed. The respective reactions in step a to d can be performed under the same conditions as in the condensation, oxidation and deprotection reactions in Scheme 1.

[Formula 18]

SCHEME 2-4: General Synthesis Process 4 for Benzene Ring Compound (Formula Ic)

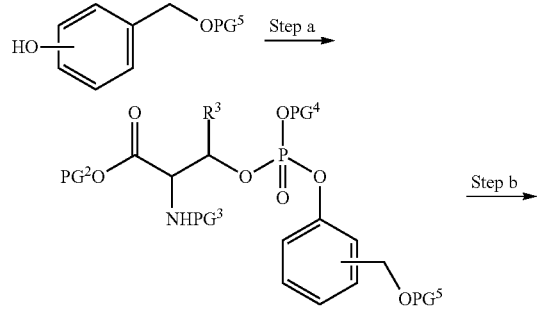

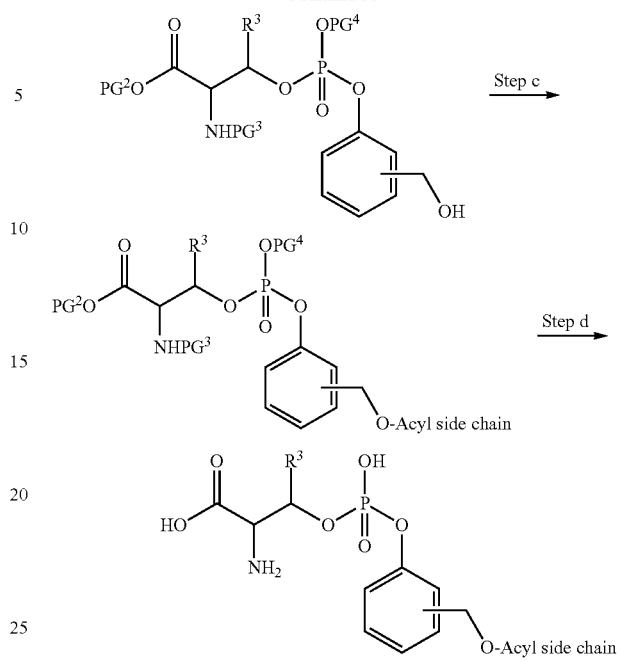

[wherein $R^3$ is as already defined herein; —O-acyl side chain corresponds to —O—CO—$R^1$ formula (Ic) already defined herein; $PG^2$, $PG^3$, $PG^4$ and $PG^5$ are as defined in above Scheme 1 or 2-3].

The compounds encompassed by formula (Ic) can, for example, be prepared by the following procedure: in step a, the hydroxy group as a substituent on the benzene ring is condensed with phosphoramidite; in step b, the alcohol is deprotected; in step c, the alcohol of the hydroxymethyl group as a substituent on the benzene ring is condensed with the acyl side chain site; in step d, deprotection such as of phosphoric acid, carboxylic acid and amine is performed. The respective reactions in step a to d can be performed under the same conditions as in the condensation, oxidation and deprotection reactions in Scheme 1.

[Formula 19]

SCHEME 2-5: General Synthesis Process 3 for Benzene Ring Compound (Formula Id)

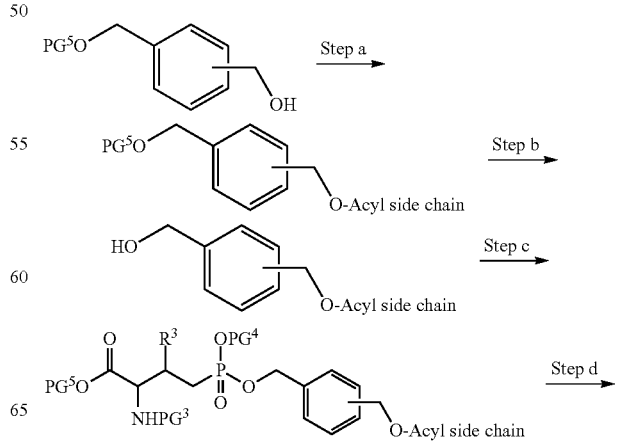

-continued

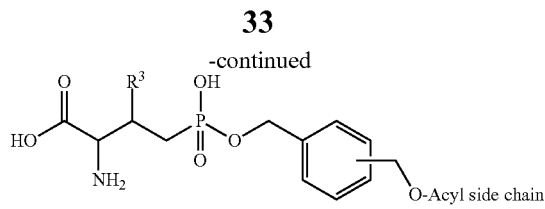
O-Acyl side chain

-continued

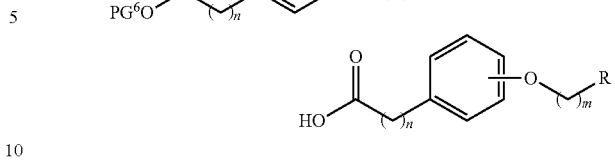

[wherein n and m are as already defined herein; PG$^6$ means a protective group, for example, PG$^6$ is TBS or C$_{1-6}$ alkyl (methyl, ethyl, tert-butyl)].

The side chain site having a benzene ring which is to be used in the synthesis of formulas (I), (IA), (IB) and (Ia) to (Id) can, for example, be prepared by carboxylic acid protection for a phenol having a carboxylic acid group in step a, alkylating the phenol in step b, and deprotecting the carboxylic acid in step c.

The phosphoric acid protection in step a can be carried out by subjecting the reaction mixture to suitable deprotecting conditions. The alkylation reaction in step b can, for example, be performed under suitable conditions using an alkyl halide as a reactant. The deprotection in step c can be performed by subjecting the reaction mixture to suitable deprotecting conditions.

[Formula 20]

SCHEME 3: General Synthesis Process for Amino Acid Site

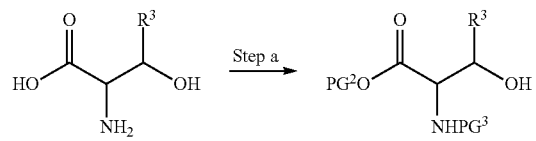

[wherein R$^3$, PG$^2$ and PG$^3$ are as already defined herein].

Amino acid sites to be used in the synthesis of formulas (I), (IA), (IB) and (Ia) to (Id) can, for example, be prepared by protecting a carboxylic acid (as an alcohol form of amino acid) and amine with the suitable substituents PG$^2$ and PG$^3$.

The carboxylic acid and amine protecting reactions in step a can be performed by subjecting the reaction mixture to suitable protecting conditions.

[Formula 21]

SCHEME 4: General Synthesis Process for Phosphoramidite

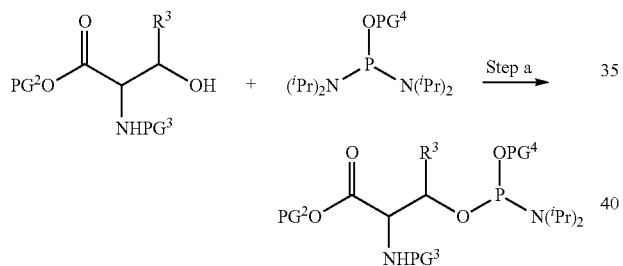

[wherein R$^3$, PG$^2$, PG$^3$ and PG$^4$ are as already defined herein].

Phosphoramidite to be used in the synthesis of formulas (I), (IA), (IB) and (Ia) to (Id) can be prepared by, for example, reacting the alcohol (amino acid site) synthesized in Scheme 3 with bis(diisopropylamino)-tert-butylphosphine. The condensation substep of step a can be performed under the same conditions as in the condensation substep of step a in Scheme 1.

[Formula 22]

SCHEME 5: General Synthesis Process (1) for Side Chain Site Having a Benzene Ring

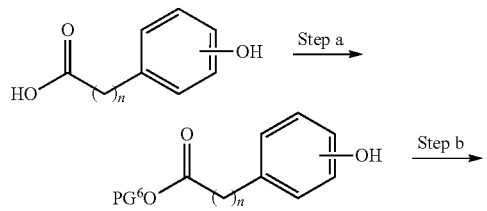

[Formula 23]

SCHEME 6: General Synthesis Process (2) for Side Chain Site Having Benzene Rings

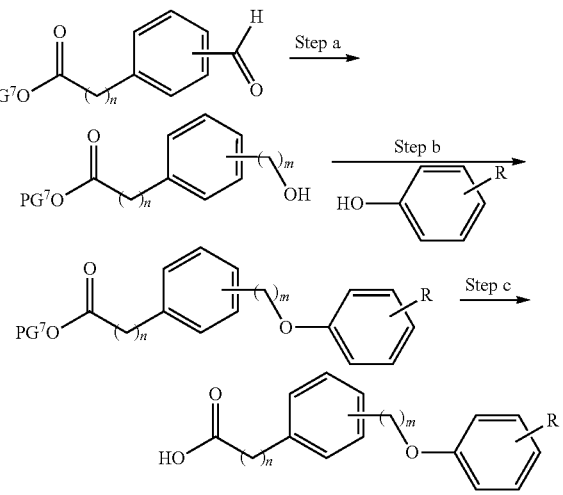

[wherein n and m are as already defined herein; PG$^7$ means a protective group, for example, PG$^7$ is TBS or C$_{1-6}$ alkyl (methyl, ethyl, tert-butyl)].

The side chain site having benzene rings which is to be used in the synthesis of formulas (I), (IA), (IB) and (Ia) to (Id) can, for example, be prepared by reducing the aldehyde as a substituent on the benzene ring to an alcohol in step a, effecting coupling to the phenol in step b, and deprotecting the carboxylic acid in step c.

The reduction of the aldehyde in step a can, for example, be performed by subjecting the reaction mixture to suitable protecting conditions using sodium borohydride as a reducing agent. The reaction for coupling with the phenol in step b can, for example, be performed under suitable conditions using DEAD as a reactant. The deprotection in step c can be performed by subjecting the reaction mixture to suitable deprotecting conditions.

Pharmaceutical Compositions

The pharmaceutical compositions of the present invention can be formulated in a variety of dosage forms which include, but are not limited to: tablets, capsules, powders, granules, pills, liquids, emulsions, suspensions, solutions, spirits, syrups, extracts, and elixirs for oral administration; and as preparations for parenteral administration, injections such as subcutaneous injections, intravenous injections, intramuscular injections, and intraperitoneal injections; transdermic preparations or patches, ointments or lotions; sublingual preparations and oro-mucosal patches for administration into the oral cavity; as well as aerosols for transnasal administration. These preparations can be produced by known methods commonly employed in pharmaceutical formulation procedures. Compounds of formulas (I), (IA), (IB) and (Ia) to (Id) are preferably administered as parenteral preparations.

The pharmaceutical compositions under consideration can contain the variety of ingredients in common use and may contain, for example, one or more pharmaceutically acceptable excipients, disintegrants, diluents, lubricants, odorizers, colorants, sweeteners, flavoring agents, suspending agents, wetting agents, emulsifiers, dispersants, auxiliary agents, antiseptics, buffers, binders, stabilizers, coating agents, etc. In addition, the pharmaceutical compositions of the present invention may be of prolonged- or extended-release dosage form.

The dosage of the therapeutics, prophylactics or pharmaceutical compositions of the present invention can be selected appropriately depending upon such factors as the administration route, the physique of the patient, his/her age, physical condition, the severity of the disease, and the elapsed time after its onset, and the pharmaceutical compositions of the present invention may contain therapeutically effective amounts and/or prophylactically effective amounts of the compounds of above formulas (I), (IA), (IB) and (Ia) to (Id). In the present invention, the compounds of above formulas (I), (IA), (IB) and (Ia) to (Id) are generally used at doses of 1 to 10000 mg/day/adult. The pharmaceutical compositions of the present invention may be administered bolus or administered more than once; they may also be used in combination with other medications such as immunosuppressants (cyclosporine, tacrolimus, sirolimus, methotrexate, azathioprine, etc.), steroidal anti-inflammatory drugs (hydrocortisone, prednisolone, dexamethasone, etc.), non-steroidal anti-inflammatory drugs (loxoprofen sodium, indometacin, diclofenac sodium, etc.), or antibody drugs (infliximab, adalimumab, tocilizumab, certolizumab pegol, etanercept, etc.)

The therapeutics or prophylactics of the present invention may, depending on the need, contain conventionally known components such as colorants, preservatives, scents, flavors, coating agents, antioxidants, vitamins, amino acids, peptides, proteins, and minerals (iron, zinc, magnesium, iodine, etc.) The therapeutics or prophylactics of the present invention may be prepared in forms suitable for pharmaceutical compositions, functional foods, health foods, drinks, supplements, etc., such as, for example, a variety of solid preparations such as granules (including dry syrups), capsules (soft capsules, hard capsules), tablets (including chewable tablets), powders (dusts), and pills, or liquid preparations such as liquids for oral administration (including liquids, suspensions and syrups). The therapeutics or prophylactics of the present invention may be directly used as pharmaceutical compositions, functional foods, health foods, supplements, and so on.

Additives for formulation purposes may include, for example, excipients, lubricants, binders, disintegrants, fluidization agents, dispersants, wetting agents, antiseptics, viscous agents, pH modifiers, colorants, corrigents, surfactants, and solvent promoters. In the case of providing the form of liquids, thickeners such as pectin, xanthan gum, and guar gum may be incorporated. It is also possible to prepare coated tablets using coating agents, or to prepare a paste of gels. What is more, even in the case of preparing other forms, conventional methods may be adopted.

Pharmaceutical compositions as one mode of the present invention, being based on the chemical structures of the compounds represented by formulas (I), (IA), (IB) and (Ia) to (Id), possess a variety of actions on any one or more of the lysophosphatidylserine receptors selected from among GPR34, P2Y10, and GPR174, which include, for example: lysophosphatidylserine receptor function modulating activities; lysophosphatidylserine receptor agonistic activities; action for suppressing the degranulation of mast cells; action for suppressing histamine release, action for suppressing leukotriene production; action for suppressing prostaglandin production; action for suppressing IL-13 production; action for suppressing tryptase secretion; and action for suppressing antigen-antibody reaction. In addition, the pharmaceutical compositions of the present invention can be used as therapeutics or prophylactics for diseases such as autoimmune diseases. Autoimmune diseases may be any of systemic diseases and organ-specific diseases and include, for example, malignant rheumatoid arthritis, systemic lupus erythematosus, multiple sclerosis, myasthenia gravis, Graves' disease, anti-phospholipid antibody syndrome, Sjögren's syndrome, primary biliary cirrhosis, polymyositis, and autoimmune hepatitis.

Lysophosphatidylserine Receptor Function Modulators

According to one aspect of the present invention, there are provided function modulators comprising the above compounds or salts thereof, or agents for modulating the function of one or more receptors selected from among GPR34, P2Y10, and GPR174. Such lysophosphatidylserine function modulators may selectively modulate the functions of any two receptors selected from among GPR34, P2Y10, and GPR174 or may selectively modulate the function of P2Y10.

The term "lysophosphatidylserine receptor function modulators" as used herein refers to agents that act on lysophosphatidylserine receptors such as GPR34, P2Y10 and GPR174 and which, therefore, are used in order to enhance or suppress the expression of the receptor of interest or to enhance or suppress the in vivo function that is characteristic of that particular receptor.

Here, the lysophosphatidylserine receptors are module-type compounds each consisting of hydrophilic sites (amino acid site and phosphate diester site), a hydrophobic site (acyl side chain site), and a linkage site for linking the hydrophilic sites to the hydrophobic site, so by systematically converting the respective modular structures in accordance with the general synthesis processes for the above compounds and checking to see if each modular structure is necessary for the expression of biological activity, it becomes possible to unravel the required structures for lysophosphatidylserine to express its biological activity or the structural requirements for creating receptor-selective agonists. Thus, for example, the lysophosphatidylserine receptor function modulators according to the present invention can also be used as a chemical tool for unraveling unknown physiological functions of the lysophosphatidylserine receptors by allowing them to contain compounds having agonistic activity against one or more receptors, or compounds having agonistic activity selective for two receptors (dual agonistic activity) or agonistic activity selective for a single receptor. In addition, the lysophosphatidylserine receptor function modulators according to the present invention can also be used as active ingredients of the above-described pharmaceutical compositions.

<GPR34 Function Modulator>

Since GPR34 features high expression in mononuclear cells, mostly in macrophages, they are assumed to be involved in the control of migration, proliferation, and activation of macrophages and granulocytes. What is more, it was found in a pulmonary infection experiment with a pathogenic bacterium (Cryptococcus neoformans) that GPR34 knockout mice had higher pathogenic bacterium counts than native mice and were impaired in their ability to eliminate the pathogenic bacterium. Thus, it has been suggested that GPR34 is involved in a wide range of immune responses as mediated by mononuclear cells and the lysophosphatidylserine receptor function modulator that selectively modulates the function of GPR34 can be used to unravel the physiological functions associated with mononuclear cells.

There is also a report confirming that the production of cytokines such as tumor necrosis factor-α (TNF-α) and interferon-γ (IFN-γ) was overenhanced in GPR34 knockout mice, suggesting that GPR34 has a function for suppressing the production of cytokines. In other words, the lysophosphatidylserine receptor function modulator that selectively modulates the function of GPR34 can be used as a chemical tool for unraveling the suppressed production of in vivo cytokines.

The GPR34 function modulator is also useful as pharmaceuticals such as prophylactis and therapeutics for the diseases associated with the function of GPR34.

<P2Y10 Function Modulator>

It has been shown that P2Y10 is mostly expressed in lymphatic organs such as thymus and spleen and that notably, the expression is greatly increased in activated lymphocytes. It has also been reported that P2Y10 inhibits the formation of cell aggregates from activated T lymphocytes by controlling the LFA1 function, suggesting a possible physiological function of P2Y10 that is involved in suppressing cell adhesion by inhibiting the LFA-1/ICAM-1 interaction of activated lymphocytes. In other words, the lysophosphatidylserine receptor function modulator that selectively modulates the function of P2Y10 can be used as a chemical tool for unraveling the physiological functions associated with suppressed cell adhesion of activated lymphocytes.

The P2Y10 function modulator is also useful as pharmaceuticals such as prophylactis and therapeutics for the diseases associated with the function of P2Y10.

<GPR174 Function Modulator>

GPR174, similar to P2Y10, is mostly expressed in lymphatic organs such as thymus and spleen and notably, the expression is greatly increased in activated lymphocytes; hence, there is a possibility that GPR174 is also responsible for some important function to be exhibited at an activation stage of the immune system. For example, it has been shown that while the P2Y10 selective agonist did not suppress the IL-2 production by activated lymphocytes, the GPR174 selective agonist inhibited the IL-2 production. It has also been reported that the single nucleotide polymorphisms of GPR174 are associated with Graves' disease and hyperthyroidism which are characterized by autoimmune antibody targeting antigens that are specifically expressed in thyroid tissue. In other words, the lysophosphatidylserine receptor function modulator that selectively modulates the function of GPR174 can be used as a chemical tool for unraveling the physiological functions associated with the suppressed IL-2 production by activated lymphocytes.

The GPR174 function modulator is also useful as prophylactis and therapeutics for the diseases associated with the function of GPR174, for example, diseases associated with the immune system, notably Graves' disease and hyperthyroidism.

Methods for Evaluating the Compounds or Salts Thereof

The agonistic activity of test compounds against the lysophosphatidylserine receptors can be evaluated using GPR34, P2Y10 or GPR174. In other words, the methods for evaluating or screening the above-described compounds or salts thereof as test compounds are not particularly limited as long as they use GPR34, P2Y10 or GPR174 but they can, for example, be performed using cells that express the gene encoding GPR34, P2Y10 or GPR174, transgenic non-human mammals that overexpress the gene encoding GPR34, P2Y10 or GPR174, or transgenic non-human mammals that express the gene encoding human GPR34, human P2Y10 or human GPR174. Here, the cells that can be used for evaluation or screening purposes are not particularly limited and include known cultured cells in common use, for example, HEK293 cell. In addition, examples of non-human mammals include mouse, rat, rabbit, dog, cat, monkey, etc. Further in addition, screening may be performed using animal tissues or cells. In this case, the test compounds may be administered by allowing them to act on the subject as by incorporating them as in a solution or culture medium in which the tissues or cells are retained.

The compounds or salts thereof can be evaluated or screened using cultured cells that express the gene encoding GPR34, P2Y10 or GPR174, and the use of cultured cells is preferred from the screening efficiency viewpoint. In addition, since GPR34, P2Y10 or GPR174 is a G protein conjugated receptor, assay can be performed using calcium response, cAMP production, reporter gene, etc. as an indicator. It is also possible to perform an assay by further expressing in said cultured cells the gene which encodes a labeled human epithelial growth factor receptor (EGFR) ligand and then determining the amount of the labeled compound to be cleaved. Specific examples of the labeled EGFR ligand include a fusion protein of EGFR ligand and alkali phosphatase (AP). In addition, EGFR ligands to be labeled include a transforming growth factor α (TGFα). To implement an assay process using the labeled EGFR ligand, reference may be made, for example, to Tokumaru et al., J Cell Biol 151, 209-220 (2000); Inoue et al., Nature Methods 9, 1021-1019 (2012).

The GPR34, P2Y10 or GPR174 to be used in the above evaluation or screening procedure is not particularly limited as long as it is a polypeptide having the activity of these receptors and, as an example, GPR34, P2Y10 or GPR174 derived from mammals such as human, mouse and rat may be used. As specific examples, polypeptides having GPR34, P2Y10 or GPR174 activity as disclosed in Patent Documents 2 and 5 may be employed.

EXAMPLES

Hereinafter, the present invention is described in further detail by showing Examples but it should be understood that the present invention is by no means to those Examples.

Reagents and Data Measurement

Reagents purchased from Sigma-Aldrich Chemical Co., Tokyo Chemical Industry Co., Ltd., Wako Pure Chemical Industries, Ltd. and Kanto Chemical Co., Ltd. were used without further purification. For $^1$H- and $^{13}$C-NMR measurements, BRUKER AVANCE400 spectrometer (400 MHz) was used; chemical shifts were cited in ppm with respect to deuterated chloroform (7.26 ppm ($^1$H-NMR) or 77.00 ppm ($^{13}$C-NMR)). As for $^{31}$P-NMR chemical shifts, they were cited in ppm with respect to phosphoric acid in water (85% w/w, 0.00 ppm). Mass analysis was measured in positive- and negative-ion modes with BRUKER micro-TOF-05 spectrometer (ESI-TOF) or SHIMADZU AXIMA-TOF (MALDI-TOF). The silica gel for use in column chromatography was purchased from Kanto Chemical Co., Ltd. Elemental analysis was conducted using Yanaco MT-6 CHN CORDER spectrometer.

Example 1

Synthesis of O-(hydroxy(2-((3-(2-(undecyloxy)phenyl)propanoyl)oxy)phenoxy)phosphoryl)-L-serine

[Formula 24]

Compound 1

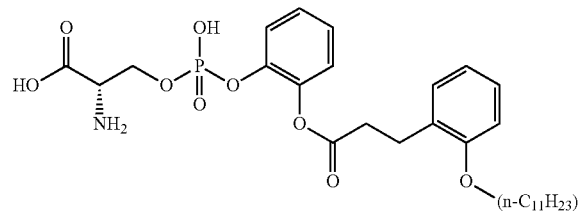

Synthesis of Intermediate 1-1

[Formula 25]

Intermediate 1-1

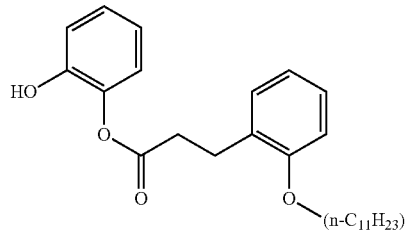

To a solution in dichloromethane (5 mL) of catechol (183.9 mg, 1.670 mmol) and compound 14 (256.3 mg, 0.800 mmol) synthesized according Scheme 9 set out below, EDCl/HCl (317.4 mg, 1.656 mmol) and DMAP (22.5 mg, 0.184 mmol)) were added, followed by stirring at room temperature for 17 hours. The resulting solution was diluted with water (20 mL) and the aqueous layer was separated, followed by three extractions with dichloromethane (20 mL×3). The organic layers were combined, dried with sodium sulfate, and the solvent was distilled off. The residue was purified by column chromatography (hexane:ethyl acetate=10:1) to give the titled compound 1-1 (268.1 mg, 0.650 mmol, 81%, colorless oil).

$^1$H-NMR (CDCl$_3$): δ=7.230 (2H, m), 7.101 (1H, m), 6.963 (1H, dd, J=8.0 Hz, 1.6 Hz), 6.901 (3H, m), 5.178 (1H, s), 4.008 (2H, t, J=6.6 Hz), 3.108 (2H, t, J=7.4 Hz), 2.964 (2H, t, J=7.2 Hz), 1.822 (2H, m), 1.486 (2H, m), 1.401-1.220 (14H, m), 0.890 (311, t, J=6.8 Hz).

$^{13}$C-NMR (CDCl$_3$): δ=171.65, 156.93, 146.97, 138.38, 129.98, 128.18, 128.03, 126.86, 122.34, 120.74, 120.51, 117.60, 111.49, 68.06, 34.31, 31.89, 29.60, 29.58, 29.36, 29.32, 29.28, 26.42, 26.15, 22.66, 14.10.

HRMS (ESI-TOF, [M-H]$^-$): C$_{26}$H$_{35}$O$_4^-$ calc'd: 411.2541; found: 411.2559.

Synthesis of Intermediate 1-2

[Formula 26]

Intermediate 1-2

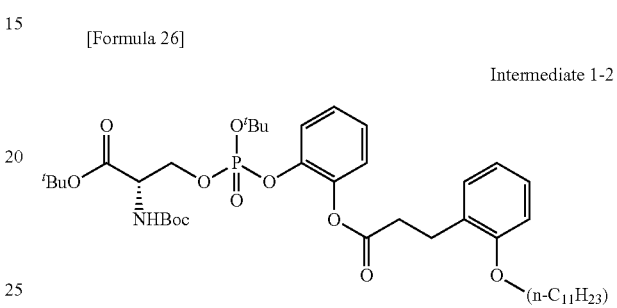

To remove the contained water, phosphoramidite 13 (187.7 mg, 0.404 mmol) synthesized according to Scheme 8 set out below was dissolved in dichloromethane and toluene and, thereafter, the solvents were distilled off under vacuum. To the resulting residue, intermediate 1-1 (206.2 mg, 0.500 mmol) was added and after adding dichloromethane and toluene, the solvents were distilled off under vacuum. In an argon atmosphere, the residue was dissolved in dichloromethane (2 mL) and a solution of 1H-tetrazole (44.3 mg, 0.632 mmol) in tetrahydrofuran (THF) (2 mL) was added at room temperature. A white powder precipitated in a few seconds. The liquid reaction mixture was stirred at room temperature for 6.5 hours and a saturated aqueous NaHCO$_3$ solution (10 ml) was added to quench the reaction, followed by three extractions with dichloromethane (20 ml×3). The organic layers were combined, dried with sodium sulfate, and the solvent was distilled off. The residue was purified by column chromatography (hexane:ethyl acetate:triethylamine=35:4:1) and the solvents were distilled off. The resulting residue was dissolved in dichloromethane (4 ml) in an argon atmosphere. Then, tert-butylhydroperoxide (TBHP's decane solution (5.0-6.0 M, 131.0 μL, 0.655 mmol)) was added at room temperature and after stirring at room temperature for 9.5 hours, the solvents were distilled off. The residue was purified by column chromatography (hexane:ethyl acetate=4:1-3:1) to give the titled compound 1-2 (143.2 mg, 0.181 mmol, 45%, colorless oil).

$^1$H-NMR (CDCl$_3$): δ=7.433 (1H, m), 7.239-7.098 (4H, m), 7.023 (1H, m), 6.870 (2H, m), 5.459 (1H, m), 4.449-4.237 (3H, m), 3.985 (2H, t, J=6.6 Hz), 3.072 (2H, m), 2.912 (2H, m), 1.819 (2H, quintet, J=7.0 Hz), 1.494 (11H, d, J=5.2 Hz), 1.418 (18H, m), 1.381-1.260 (14H, m), 0.876 (3H, t, J=7.0 Hz).

$^{13}$C-NMR (CDCl$_3$): δ=170.83, 170.81, 168.05, 168.01, 156.89, 155.12, 155.09, 142.46, 142.39, 141.31, 141.25, 141.24, 130.05, 128.39, 127.58, 126.47, 126.42, 125.05, 123.70, 120.97, 120.14, 110.96, 85.25, 85.18, 82.59, 82.56, 79.74, 79.72, 68.10, 68.05, 68.00, 67.71, 54.34, 54.25, 54.16, 33.80, 33.78, 31.79, 29.64, 29.60, 29.52, 29.50, 29.31, 29.24, 29.22, 28.17, 27.77, 26.06, 22.55, 13.99.

$^{31}$P-NMR (CDCl$_3$): δ=−11.39, −11.71.

HRMS (ESI-TOF, [M+Na]$^+$): C$_{42}$H$_{66}$NNaO$_{11}$P$^+$ calc'd: 814.4266; found: 814.4247.

Synthesis of Compound 1

[Formula 27]

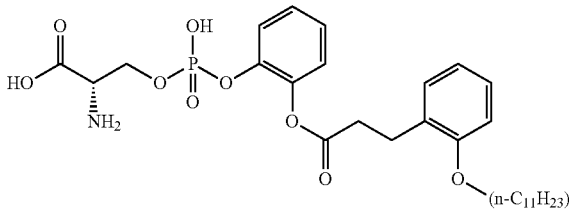

Compound 1

Protected intermediate 1-2 (138.3 mg, 0.175 mmol) was dissolved in 1,3-dimethoxybenzene (0.5 ml) and, thereafter, TFA (2 mL) was added. The mixture was stirred at 0° C. for an hour, then at room temperature for an additional 4 hours, followed by dilution with chloromethane (20 mL), and the solvents were distilled off. The residue was purified by column chromatography (chloroform:methanol:acetic acid=9:1:0-8:1:1-7:1:2, chloroform:methanol:acetic acid=9:1:0-10:1:1-9:1:1-8:1:1-7:1:2) to give an acetic acid salt of the titled compound (66.5 mg, 0.115 mmol, 66%, white powder). The resulting acetic acid salt was dissolved in TFA and the solvent was distilled off to give the titled compound as a TFA salt (white powder).

$^1$H-NMR (CDCl$_3$/TFA-d): δ=7.266-7.134 (5H, m), 6.907 (3H, m), 4.577 (2H, d, J=4.4 Hz), 4.376 (1H, brs), 4.027 (2H, t, J=6.8 Hz), 3.072 (2H, t, J=7.0 Hz), 2.975 (2H, t, J=7.0 Hz), 1.812 (2H, quintet, J=7.0 Hz), 1.463 (2H, m), 1.397-1.272 (14H, m), 0.885 (3H, t, J=6.6 Hz).

$^{31}$P-NMR (CDCl$_3$/TFA-d): δ=−6.86.

HRMS (ESI-TOF, [M-H]$^-$): C$_{29}$H$_{41}$NO$_9$P$^-$ calc'd: 578.2524; found: 578.2513.

Mp: 107.0° C.-110.0° C., colorless solid cube.

Elemental analysis: C$_{29}$H$_{42}$NO$_9$P.0.5CF$_3$COOH calc'd: C, 56.60; H, 6.73; N, 2.20; found: C, 56.80; H, 6.73; N, 2.13.

Example 2

Synthesis of O-(hydroxy(3-((3-(2-(undecyloxy)phenyl)propanoyl)oxy)phenoxy)phosphoryl)-L-serine

[Formula 28]

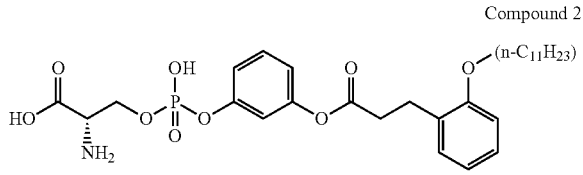

Compound 2

Synthesis was performed by the same method as in Example 1 except that catechol was replaced by resorcinol; in the final step, purification was conducted by column chromatography (chloroform:methanol:acetic acid=9:1:0-8:1:1-7:1:2-6:1:3) to give an acetic acid salt of the titled compound (83.3 mg, 0.144 mmol, 99%, white powder). In addition, from the resulting acetic acid salt, a TFA salt of the titled compound was obtained (white powder).

$^1$H-NMR (CDCl$_3$/TFA-d): δ=7.317 (1H, t, J=8.2 Hz), 7.234 (1H, dt, J=7.7 Hz, 1.2 Hz), 7.154 (1H, m), 7.035 (1H, d, J=7.6 Hz), 6.910 (2H, m), 6.850 (1H, s), 6.772 (1H, d, J=8.0 Hz), 4.615 (2H, brs), 4.385 (1H, brs), 4.031 (2H, t, J=6.8 Hz), 3.069 (2H, t, J=7.2 Hz), 2.962 (2H, t, J=7.2 Hz), 1.824 (2H, quintet, J=7.0 Hz), 1.478 (2H, m), 1.380-1.269 (14H, m), 0.876 (2H, t, J=6.8 Hz).

$^{31}$P-NMR (CDCl$_3$/TFA-d): δ=−6.98.

HRMS (ESI-TOF, C$_{29}$H$_{41}$NO$_9$P$^-$ calc'd: 578.2524; found: 578.2513.

Mp: 123.0° C.-126.5° C., colorless solid plate.

Elemental analysis: C$_{29}$H$_{42}$NO$_9$P.0.5CF$_3$COOH calc'd: C, 56.60; H, 6.73; N, 2.20; found: C, 56.94; H, 6.81; N, 2.17.

Example 3

Synthesis of O-(hydroxy(4-((3-(2-(undecyloxy)phenyl)propanoyl)oxy)phenoxy)phosphoryl)-L-serine

[Formula 29]

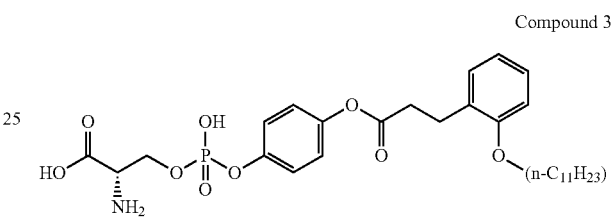

Compound 3

Synthesis was performed by the same method as in Example 1 except that catechol was replaced by hydroquinone; in the final step, purification was conducted by column chromatography (chloroform:methanol:acetic acid=9:1:0-10:1:1-9:2:1) to give an acetic acid salt of the titled compound (44.5 mg, 0.077 mmol, 78%, white powder). In addition, from the resulting acetic acid salt, a TFA salt of the titled compound was obtained (white powder).

$^1$H-NMR (CDCl$_3$/TFA-d): δ=7.253 (1H, dt, J=7.8 Hz, 1.1 Hz), 7.151 (3H, m), 6.923 (4H, t, J=7.4 Hz), 4.607 (2H, brs), 4.380 (1H, brs), 4.048 (2H, t, J=6.6 Hz), 3.093 (2H, t, J=7.2 Hz), 2.991 (2H, t, J=7.0 Hz), 1.848 (2H, quintet, J=7.0 Hz), 1.497 (2H, m), 1.406-1.290 (14H, m), 0.895 (3H, t, J=6.8 Hz).

$^{31}$P-NMR (CDCl$_3$/TFA-d): δ=−6.82.

HRMS (ESI-TOF, [M-H]$^-$): C$_{29}$H$_{41}$NO$_9$P$^-$ calc'd: 578.2524; found: 578.2564.

Mp: 140.5° C.-142.0° C., colorless solid cube.

Elemental analysis: C$_{29}$H$_{42}$NO$_9$P.0.3CF$_3$COOH calc'd: C, 57.92; H, 6.95; N, 2.28; found: C, 57.68; H, 6.98; N, 2.27.

Example 4

Synthesis of O-(hydroxy(2-(((3-(2-(undecyloxy)phenyl)propanoyl)oxy)methyl)phenoxy)phosphoryl)-L-serine

[Formula 30]

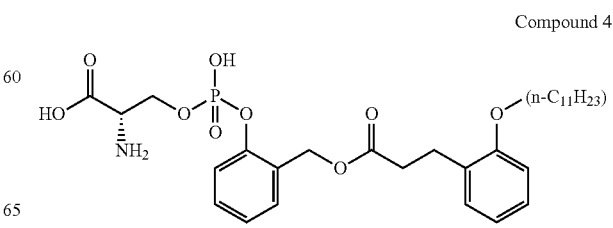

Compound 4

Synthesis of Intermediate 4-1

[Formula 31]

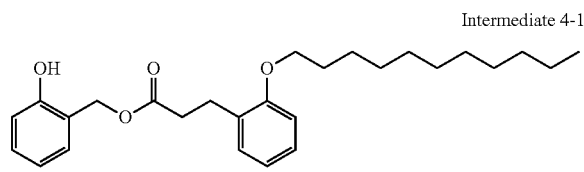

Intermediate 4-1

To a solution of 2-(hydroxymethyl)phenol (100.0 mg, 0.8055 mmol) and compound 14 (258.2 mg, 0.8055 mmol) in dichloromethane (2 mL), a solution of DIC (204.2 mg, 1.6111 mmol) and DMAP (19.7 mg, 0.1611 mmol) in dichloromethane (2 mL) was added, followed by stirring at room temperature for 2 hours. The resulting solution was diluted with water (10 mL) and dichloromethane (10 mL) and the aqueous layer was separated, followed by three extractions with dichloromethane (8 mL×3). The organic layers were combined, dried with magnesium sulfate, and the solvent was distilled off. The residue was purified by column chromatography (hexane:ethyl acetate=20:1-10:1-4:1) to give the titled compound (130.7 mg, 0.3064 mmol, 38.03%, colorless oil).

$^1$H NMR (CDCl$_3$): δ (ppm): δ=7.357-7.283 (m, 2H), 7.217 (dt, 1H, J=8.0 Hz, 7.6 Hz, 1.6 Hz), 7.127 (dd, 1H, J=7.6 Hz, 1.6 Hz), 7.011 (dd, 1H, J=8.0 Hz, 1.2 Hz), 6.963 (dt, 1H, J=7.6 Hz, 7.2 Hz, 1.2 Hz), 6.897-6.842 (m, 2H), 4.001 (t, 2H, J=6.4 Hz), 3.025-2.987 (m, 2H), 2.758-2.720 (m, 2H) 1.882-1.812 (m, 2H), 1.557-1.485 (m, 2H), 1.387-1.355 (m, 14H), 0.966 (t, 3H, J=6.8)

$^{13}$C NMR (CDCl$_3$): δ (ppm): δ=176.04, 156.94, 155.64, 132.15, 131.08, 129.99, 128.38, 127.72, 121.86, 120.52, 120.26, 117.84, 111.05, 67.79, 63.22, 34.20, 32.00, 29.70, 29.67, 29.43, 29.36, 26.23, 22.77, 14.20

HRMS (ESI-TOF [M+Na]$^+$): C$_{27}$H$_{38}$NaO$_4$$^+$ calc'd 449.2662; found 449.2635.

Elemental analysis: calc'd C, 76.02%; H, 8.98%; N, 0.00%; found C, 75.74%; H, 8.82%; N, 0.00%.

Synthesis of Intermediate 4-2

[Formula 32]

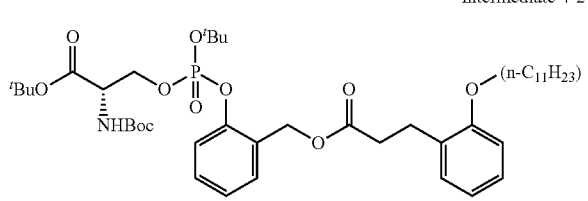

Intermediate 4-2

To remove the contained water, phosphoramidite 13 (177.4 mg, 0.3022 mmol) was dissolved in dichloromethane (2 mL) and toluene (0.2 mL) and, thereafter, the solvents were distilled off under vacuum. To the resulting residue, intermediate 4-1 (128.9 mg, 0.3022 mmol) was added and following the addition of dichloromethane (2 mL) and toluene (0.2 mL), the solvents were distilled off under vacuum. In an argon atmosphere, the residue was dissolved in dichloromethane (1 mL) and a solution of 1H-tetrazole (63.5 mg, 0.9065 mmol) in THF (1 mL) was added at room temperature. A white powder precipitated in a few seconds. The liquid reaction mixture, after being stirred at room temperature for 12 hours, was diluted with dichloromethane (8 ml) and a saturated aqueous NaHCO$_3$ solution (10 ml) was added to quench the reaction, followed by three extractions with dichloromethane (8 ml×3). The organic layers were combined, dried with magnesium sulfate, and the solvent was distilled off. The residue was purified by column chromatography (hexane:ethyl acetate=4:1-2:1) to give a trivalent phosphate diester intermediate (200.2 mg, 0.2534 mmol, 83.9%). The resulting intermediate was dissolved in dichloromethane (2 ml) in an argon atmosphere. Then, tert-butylhydroperoxide (TBHP's decane solution (5.0-6.0 M, 0.1013 mL, 0.5066 mmol)) was added at room temperature, followed by stirring at room temperature for 1.5 hours. The solvents in the resulting solution were distilled off and the residue was purified by column chromatography (hexane:ethyl acetate=4:1-2:1) to give the titled compound (132.7 mg, 0.1671 mmol, 66.0% (2 steps: 55.3%), colorless oil).

$^1$H NMR (CDCl$_3$): δ (ppm): δ=7.306-7.169 (m, 3H), 7.102-7.027 (m, 3H), 6.767-6.726 (m, 2H), 5.458-5.320 (m, 1H), 5.144-5.135 (m, 2H), 4.408-4.201 (m, 3H), 3.886-3.853 (m, 2H), 2.916-2.877 (m, 2H), 2.633-2.594 (m, 2H), 1.744-1.674 (m, 2H), 1.433-1.416 (m, 9H), 1.371-1.345 (m, 19H), 1.255-1.155 (m, 15H), 0.799 (t, 3H, J=6.8 Hz)

$^{13}$C NMR (CDCl$_3$): δ (ppm): δ=172.99, 172.98, 168.16, 168.13, 156.95, 155.18, 148.69, 148.63, 129.96, 129.54, 129.50, 129.22, 128.79, 127.52, 127.43, 127.36, 124.93, 120.19, 119.88, 110.98, 85.28, 85.21, 82.77, 79.90, 77.41, 77.09, 76.77, 68.20, 68.14, 67.73, 60.90, 54.45, 54.39, 54.31, 34.12, 31.90, 29.79, 29.75, 29.61, 29.58, 29.36, 29.34, 29.32, 28.29, 27.92, 27.88, 26.16, 26.13, 22.67, 14.12

$^{31}$P NMR (CDCl$_3$): δ (ppm): δ=−11.03, −11.34

HRMS (ESI-TOF [M+Na]$^+$): C$_{43}$H$_{68}$NNaO$_{11}$P$^+$ calc'd 828.4422; found 828.4421.

Elemental analysis: calc'd C, 63.58%; H, 8.38%; N, 1.72% (C$_{43}$H$_{68}$NO$_{11}$P+CH$_2$Cl$_2$×0.1); found C, 63.80%; H, 8.40%; N, 1.64%.

m.p. 145-156° C.

Synthesis of Compound 4

[Formula 33]

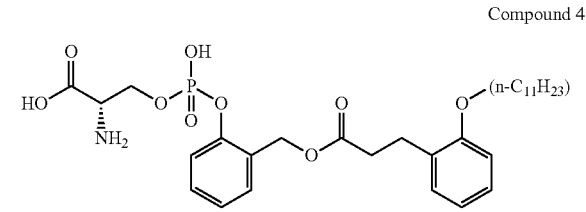

Compound 4

Protected intermediate 4-2 (127.0 mg, 0.1576 mmol) was dissolved in TFA (2 mL) and after stirring the mixture at room temperature for 1.5 hours, the solvent was distilled off.

The residue was purified by column chromatography (chloroform:methanol:acetic acid=6:1:2-6:1:3) to give the titled compound (93.3 mg, 0.1572 mmol, 99.7%, white powder).

$^1$H NMR (CDCl$_3$): δ (ppm): δ=7.309-7.254 (m, 2H), 7.226-7.120 (m, 3H), 7.024-7.005 (m, 1H), 6.892-6.824 (m, 2H), 5.227 (s, 2H), 4.690 (m, 2H), 4.494 (m, 1H), 3.991 (t, 2H, J=6.8 Hz), 2.972-2.935 (m, 2H), 2.796-2.759 (m, 2H), 1.820-1.749 (m, 2H), 1.456-1.402 (m, 2H), 1.322-1.253 (m, 14H), 0.880 (t, 3H, J=6.8 Hz)

$^{31}$P NMR (CDCl$_3$): δ (ppm): δ=−6.99

HRMS (ESI-TOF [M-H]$^−$): C$_{30}$H$_{43}$NO$_9$P$^−$ calc'd 592.2681; found 592.2664.

Elemental analysis: calc'd C, 53.76%; H, 6.27%; N, 1.95% (C$_{30}$H$_{44}$NO$_9$P+CF$_3$CO$_2$H×1.1); found C, 53.84%; H, 6.29%; N, 1.99%.

Example 5

Synthesis of O-(hydroxy(2-((3-(2-((3-phenoxybenzyl)oxy)phenyl)propanoyl)oxy)methyl)phenoxy)phosphoryl)-L-serine

[Formula 34]

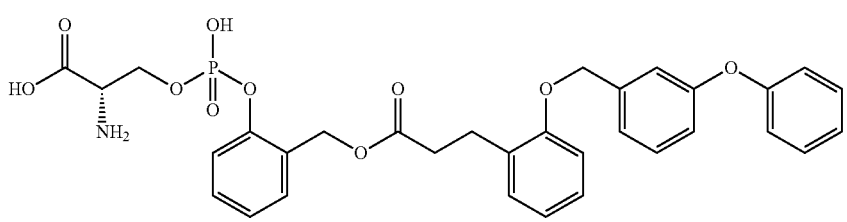

Compound 5

Synthesis of Intermediate 5-1

[Formula 35]

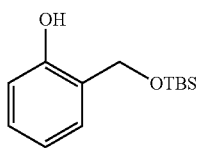

Intermediate 5-1

To a solution obtained by dissolving salicylic acid (103.3 mg, 0.8321 mmol) and imidazole (62.3 mg, 0.9153 mmol) in anhydrous dichloromethane (3 mL), a solution of TBSCl (138.0 mg, 0.9153 mmol) in dichloromethane (5 mL) was added at 0° C., followed by stirring at room temperature for 18 hours. To the resulting solution, water (10 mL) was added to quench the reaction and the aqueous layer was separated, followed by two extractions with dichloromethane (10 mL×2). The organic layers were combined, dried with sodium sulfate, and the solvent was distilled off. The residue was purified by column chromatography (hexane:ethyl acetate=2:1-1:1) to give the titled compound (96.6 mg, 0.4052 mmol, 48.7%, colorless oil).

$^1$H NMR (CDCl$_3$): δ (ppm): δ=8.053 (s, 1H), 7.220-7.179 (m, 1H), 6.987-6.968 (m, 1H), 6.913-6.893 (m, 1H), 6.859-6.822 (m, 1H), 4.930 (s, 2H), 0.966 (s, 9H), 0.169 (s, 6H)

$^{13}$C NMR (CDCl$_3$): δ (ppm): δ=156.61, 128.93, 126.69, 124.19, 119.62, 116.64, 65.85. 25.75, 18.15, −5.51

HRMS (ESI-TOF [M-H]$^−$): C$_{13}$H$_{21}$O$_2$Si$^−$ calc'd 237.1316; found 237.1320.

Elemental analysis: calc'd C, 65.50%; H, 9.30%; N, 0.00%; found C, 65.30%; H, 9.32%; N, 0.00%.

Synthesis of Intermediate 5-2

[Formula 36]

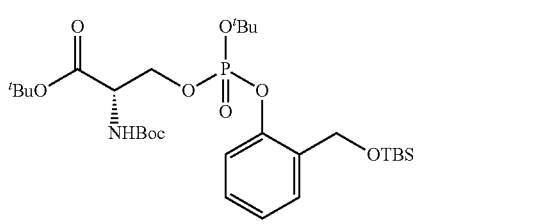

Intermediate 5-2

To remove the contained water, phosphoramidite 13 (195.6 mg, 0.4335 mmol) was dissolved in dichloromethane and toluene and, thereafter, the solvents were distilled off under vacuum. To the resulting residue, intermediate 5-1 (79.5 mg, 0.3335 mmol) was added and after adding dichloromethane and toluene, the solvents were distilled off under vacuum. In an argon atmosphere, the residue was dissolved in dichloromethane (1 mL) and a solution of 1H-tetrazole (58.4 mg, 0.8337 mmol) in THF (1 mL) was added at room temperature. A white powder precipitated in a few seconds. The liquid reaction mixture, after being stirred at room temperature for 16 hours, was diluted with dichloromethane (8 ml) and a saturated aqueous NaHCO$_3$ solution (8 ml) was added to quench the reaction, followed by two extractions with dichloromethane (10 ml×2). The organic layers were combined, dried with magnesium sulfate, and the solvent was distilled off. The residue was purified by column chromatography (hexane:ethyl acetate=4:1-2:1) to give a trivalent phosphoric acid ester intermediate (193.98 mg, 0.3220 mmol, 96.6%). The resulting intermediate was dissolved in dichloromethane (2 ml) in an argon atmosphere. Then, tert-butylhydroperoxide (TBHP's decane solution (5.0-6.0 M, 0.1594 mL, 0.6441 mmol)) was added at room temperature, followed by stirring at room temperature for 1.5 hours. The solvents in the resulting solution were removed and the residue was purified by column chromatography (hexane:ethyl acetate=4:1-1:1) to give the titled compound (174.1 mg, 0.2818 mmol, 87.5% (2 steps: 84.5%), colorless oil).

$^1$H NMR (CDCl$_3$): δ (ppm): δ=7.431-7.399 (m, 1H), 7.127-7.030 (m, 3H), 5.352-5.223 (m, 1H), 4.739-4.664 (m, 2H), 4.357-4.097 (m, 3H), 1.392-1.314 (m, 27H), 0.840 (s, 9H), −0.003 (s, 6H)

$^{13}$C NMR (CDCl$_3$): δ (ppm): δ=168.12, 155.15, 147.35, 147.28, 132.55, 132.48, 127.62, 127.51, 127.43, 124.88, 119.15, 84.94, 82.75, 82.73, 79.90, 67.94, 59.88, 54.38, 29.78, 29.73, 28.27, 27.91, 17.87, 25.92, 18.35, −5.36

$^{31}$P NMR (CDCl$_3$): δ (ppm): δ=−10.93, −11.28

HRMS (ESI-TOF [M+Na]$^+$): C$_{29}$H$_{52}$NNaO$_9$PSi$^+$ calc'd 640.3041; found 640.3053.

Elemental analysis: calc'd C, 56.38%; H, 8.48%; N, 2.27% (C$_{29}$H$_{52}$NO$_9$PSi); found C, 56.14%; H, 8.24%; N, 2.27%.

Synthesis of Intermediate 5-3

[Formula 37]

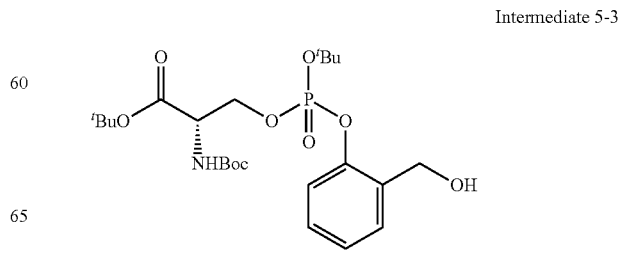

Intermediate 5-3

To a solution of intermediate 5-2 in a mixture of THF (1 mL) and pyridine (326.1 μL), HF·pyridine (132.4 μL) was added dropwise, followed by stirring for 6 hours. The resulting solution was diluted with water (10 mL) and dichloromethane (10 mL) and the aqueous layer was separated, followed by extraction with dichloromethane (10 mL×2). The organic layers were combined, dried with magnesium sulfate, and the solvents were distilled off. The residue was purified by column chromatography (hexane:ethyl acetate=2:1—ethyl acetate) to give the titled compound (53.0 mg, 0.1053 mmol, 54.8%, white solids).

$^1$H NMR (CDCl$_3$): δ (ppm): δ=7.396-7.364 (m, 1H), 7.241-7.174 (m, 1H), 7.149-7.096 (m, 2H), 5.402-5.260 (m, 1H), 4.612-4.526 (m, 2H), 4.419-4.254 (m, 3H), 3.404 (bs, 1H), 1.454-1.353 (m, 27H)

$^{13}$C NMR (CDCl$_3$): δ (ppm): δ=168.19, 155.16, 148.42, 148.35, 133.10, 133.05, 130.99, 130.94, 129.04, 125.85, 121.15, 121.08, 85.78, 85.70, 83.01, 82.98, 80.07, 68.33, 60.10, 60.08, 60.10, 60.08, 54.41, 54.33, 29.78, 29.73, 28.29, 28.26, 27.94, 27.86

$^{31}$P NMR (CDCl$_3$): δ (ppm): δ=-10.01, -10.21

HRMS (ESI-TOF [M+Na]$^+$): C$_{23}$H$_{38}$NNaO$_9$P$^+$ calc'd 526.2176; found 526.2188.

Synthesis of Intermediate 5-4

[Formula 38]

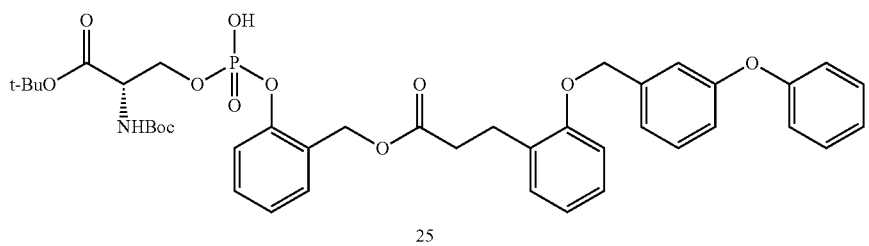

Intermediate 5-4

To a solution in dichloromethane (0.6 mL) of intermediate 5-3 (53.0 mg, 0.1053 mmol) and compound 15 (40.3 mg, 0.1158 mmol) synthesized according Scheme 9 set out below, DIC (17.3 mg, 0.1368 mmol) and DMAP (3.9 mg, 0.0316 mmol) were added and after stirring at room temperature for 15 hours, the solvent was distilled off. The residue was purified by column chromatography (hexane:ethyl acetate=4:1-2:1) to give the titled compound 5-4 (28.6 mg, 0.0343 mmol, 32.6%, colorless oil).

$^1$H NMR (CDCl$_3$): δ (ppm): δ=7.377-7.244 (m, 6H), 7.178-7.074 (m, 5H), 7.050 (m, 1H), 7.016-6.986 (m, 2H), 6.950-6.925 (m, 1H), 6.887-6.843 (m, 2H), 5.512-5.378 (m, 1H), 5.203-5.195 (m, 2H), 5.056 (s, 2H), 4.473-4.293 (m, 3H), 3.021-2.983 (m, 2H), 2.700-2.658 (m, 2H), 1.497-1.482 (m, 9H), 1.443-1.418 (m, 18H).

$^{13}$C NMR (CDCl$_3$): δ (ppm): δ=172.84, 168.13, 157.67, 156.90, 156.40, 155.20, 148.72, 148.65, 139.31, 130.18, 129.92, 129.78, 129.60, 129.55, 129.23, 129.10, 127.57, 127.40, 127.33, 124.94, 123.46, 121.53, 120.88, 119.88, 119.16, 117.91, 117.07, 111.64, 85.31, 85.24, 82.79, 79.93, 69.38, 68.17, 60.93; 54.42, 34.10, 29.79, 29.75, 28.29, 27.93, 27.89, 26.08, 14.19

$^{31}$P NMR (CDCl$_3$): δ (ppm): δ=-11.05, -11.36

HRMS (ESI-TOF [M+Na]$^+$): C$_{45}$H$_{56}$NNaO$_{12}$P$^+$ calc'd 856.3432; found 856.3419.

Elemental analysis: calc'd C, 64.32%; H, 6.68%; N, 1.66% (C$_{45}$H$_{56}$NO$_{12}$P+CH$_2$Cl$_2$×0.1); found C, 64.27%; H, 6.77%; N, 1.51%.

Synthesis of Compound 5

[Formula 39]

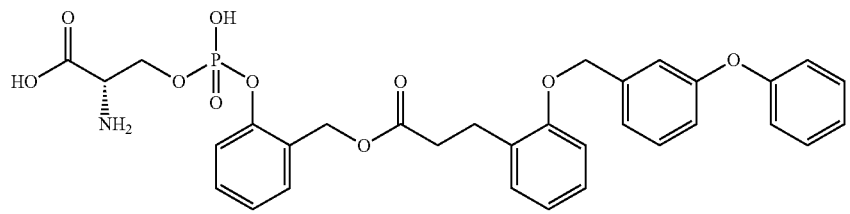 [SMILES: N[C@@H](COP(=O)(O)Oc1ccccc1COC(=O)CCc1ccccc1OCc1cccc(Oc2ccccc2)c1)C(=O)O]

Compound 5

Synthesis was performed by the same method as in Example 4 except that compound 14 was replaced by compound 15; in the final step, purification was performed by column chromatography (chloroform:methanol:water=65:25:4) to give the titled compound (15.1 mg, 0.0243 mmol, 76.4%, white powder).

$^1$H NMR (CDCl$_3$): δ (ppm): δ=7.346-7.296 (m, 4H), 7.212-7.106 (m, 6H), 7.073 (m, 1H), 7.045-6.934 (m, 4H), 6.916-6.849 (m, 2H), 5.203 (m, 2H), 5.076 (m, 2H), 4.700 (m, 2H), 4.508 (m, 1H), 2.964 (m, 2H), 2.761 (m, 2H)

$^{31}$P NMR (CDCl$_3$): δ (ppm): δ=−8.37

HRMS (ESI-TOF [M-H]$^-$): C$_{32}$H$_{31}$NO$_{10}$P$^-$ calc'd 620.1691; found 620.1663.

[Formula 41]

Elemental analysis: calc'd C, 45.88%; H, 3.48%; N, 1.37% (C$_{32}$H$_{32}$NO$_{10}$P+CF$_3$CO$_2$H×3.5); found C, 45.81%; H, 3.65%; N, 1.37%.

m.p. 162-174° C.

Example 6

Synthesis of O-(hydroxy(3-(((3-(2-(undecyloxy)phenyl)propanoyl)oxy)methyl)phenoxy)phosphoryl)-L-serine

[Formula 40]

Compound 6

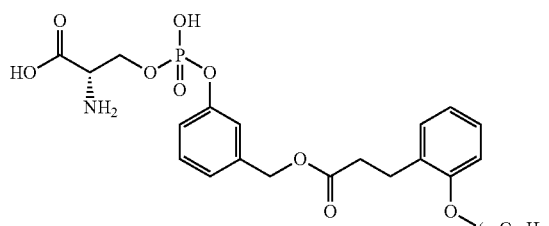

Synthesis was performed by the same method as in Example 4 except that 2-(tert-butyldimethylsilyloxymethyl)phenol was replaced by 3-(tert-butyldimethylsilyloxymethyl)phenol; in the final step, purification was performed by column chromatography (chloroform:methanol:water=65:25:4) to give the titled compound (16.2 mg, 0.0273 mmol, 93.5%, white powder).

$^1$H NMR (CDCl$_3$): δ (ppm): δ=7.323-7.284 (m, 1H), 7.201-7.158 (m, 1H), 7.129-7.110 (m, 1H), 7.051-7.026 (m, 2H), 7.004-6.983 (m, 1H), 6.870-6.807 (m, 2H), 5.085 (s, 2H), 4.643 (m, 2H), 4.431 (m, 1H), 3.994-3.961 (m, 2H), 2.948-2.911 (m, 2H), 2.755-2.718 (m, 2H), 1.812-1.742 (m, 2H), 1.467-1.398 (m, 2H), 1.353-1.249 (m, 14H), 0.889-0.854 (m, 3H)

$^{31}$P NMR (CDCl$_3$): δ (ppm): δ=−7.26

HRMS (ESI-TOF [M-H]$^-$): C$_{30}$H$_{43}$NO$_9$P$^-$ calc'd 592.2681; found 592.2680.

Elemental analysis: calc'd C, 51.83%; H, 5.96%; N, 1.83% (C$_{30}$H$_{44}$NO$_9$P+CF$_3$CO$_2$H×1.5); found C, 52.04%; H, 6.09%; N, 1.95%.

Example 7

Synthesis of O-(hydroxy(3-(((3-(2-((3-phenoxybenzyl)oxy)phenyl)propanoyl)oxy)methyl)phenoxy)phosphoryl)-L-serine Compound 7

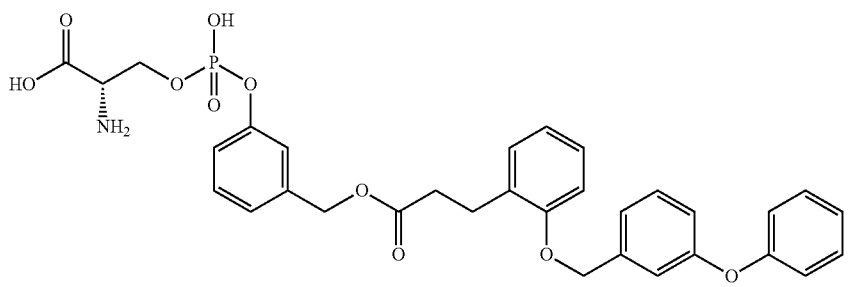 [SMILES: N[C@@H](COP(=O)(O)Oc1cccc(COC(=O)CCc2ccccc2OCc2cccc(Oc3ccccc3)c2)c1)C(=O)O]

Synthesis was performed by the same method as in Example 6 except that compound 14 was replaced by compound 15; in the final step, purification was performed by column chromatography (chloroform:methanol:water=65:25:4) to give the titled compound (18.3 mg, 0.0295 mmol, 53.2%, white powder). In addition, from the resulting acetic acid salt, a TFA salt of the titled compound was obtained.

$^1$H NMR (CDCl$_3$): δ (ppm): δ=7.353-7.274 (m, 4H), 7.203-6.945 (m, 11H), 6.900-6.845 (m 2H), 5.066-5.058 (m, 4H), 4.685 (m, 2H), 4.460 (m, 1H), 2.975-2.938 (m, 2H), 2.744-2.707 (m, 2H)

$^{31}$P NMR (CDCl$_3$): δ (ppm): δ=−6.96

HRMS (ESI-TOF [M-H]$^-$): C$_{32}$H$_{31}$NO$_{10}$P$^-$ calc'd 620.1691; found 620.1709.

m.p. 175-185° C.

Example 8

Synthesis of O-(hydroxy(4-(((3-(2-(undecyloxy)phenyl)propanoyl)oxy)methyl)phenoxy)phosphoryl)-L-serine

[Formula 42]

Compound 8

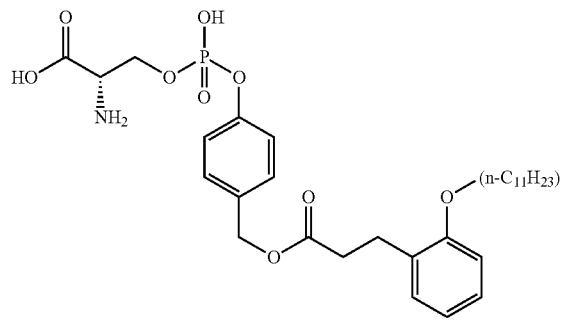

Synthesis was performed by the same method as in Example 4 except that 2-(tert-butyldimethylsilyloxymethyl)phenol was replaced by 4-(tert-butyldimethylsilyloxymethyl)phenol; in the final step, purification was performed by column chromatography (chloroform:methanol:water=65:25:4) to give a TFA salt of the titled compound (36.6 mg, 0.0607 mmol, 113.0%, white powder).

$^1$H NMR (CDCl$_3$): δ (ppm): δ=7.263-7.254 (m, 2H), 7.210-7.171 (m, 1H), 7.044-7.026 (m, 3H), 6.886-6.831 (m, 2H), 5.110 (s, 2H), 4.721 (m, 2H), 4.531 (m, 1H), 3.991 (t, 2H, J=6.4 Hz), 2.955 (t, 2H, J=7.6 Hz), 2.762 (t, 2H, J=7.6 Hz), 1.822-1.752 (m, 2H), 1.459-1.405 (m, 2H), 1.332-1.267 (m, 14H), 0.871 (t, 3H, J=6.8 Hz)

$^{31}$P NMR (CDCl$_3$): δ (ppm): δ=−6.77

HRMS (ESI-TOF [M-H]$^-$): C$_{30}$H$_{43}$NO$_9$P$^-$ calc'd 592.2681; found 592.2680.

Elemental analysis: calc'd C, 48.63%; H, 5.76%; N, 1.67% (C$_{30}$H$_{44}$NO$_9$P+TFA×2+H$_2$O×1); found C, 48.55%; H, 5.86%; N, 1.88%.

m.p. 184-193° C.

Example 9

Synthesis of O-(hydroxy((3-((3-(2-(undecyloxy)phenyl)propanoyl)oxy)benzyl)oxy)phosphoryl)-L-serine

[Formula 43]

Compound 9

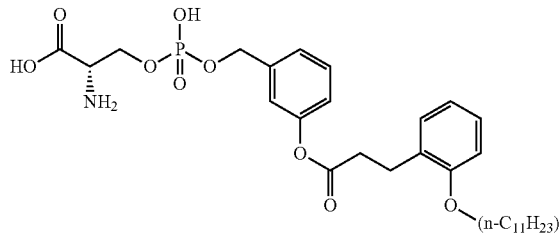

Synthesis of Intermediate 9-1

[Formula 44]

Intermediate 9-1

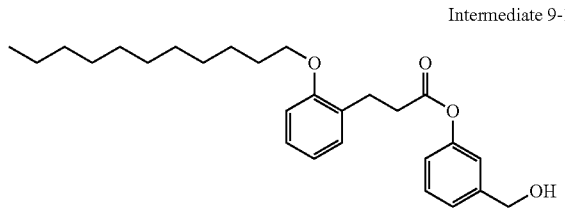

To a solution of 3-hydroxybenzyl alcohol (100.0 mg, 0.8055 mmol) and compound 14 (258.2 mg, 1.0472 mmol) in dichloromethane (2 mL), EDCl/HCl (200.7 mg, 1.0472 mmol) and DMAP (19.7 mg, 0.1611 mmol)) were added, followed by stirring at room temperature for 1.5 hours. The resulting solution was diluted with water (10 mL) and the aqueous layer was separated, followed by three extractions with dichloromethane (6 mL×3). The organic layers were combined, dried with sodium sulfate, and the solvent was distilled off. The residue was purified by column chromatography (hexane:ethyl acetate=6:1-4:1) to give the titled compound (127.0 mg, 0.2977 mmol, 37.0%, colorless oil).

$^1$H NMR (CDCl$_3$): δ (ppm): δ=7.361-7.322 (m, 1H), 7.252-7.180 (m, 3H), 7.042-7.032 (m, 1H), 6.960-6.870 (m, 3H), 4.633 (s, 2H), 4.015 (t, 2H, J=6.4 Hz), 3.097 (t, 2H, J=7.6 Hz), 2.906 (t, 2H, J=7.6 Hz), 2.385 (bs, 1H), 1.887-1.817 (m, 2H), 1.696-1.489 (m, 2H), 1.455-1.262 (m, 14H), 0.917 (t, 3H, J=6.8 Hz)

$^{13}$C NMR (CDCl$_3$): δ (ppm): δ=172.12, 157.09, 150.93, 142.79, 130.19, 129.44, 128.48, 127.80, 124.06, 120.62, 120.28, 120.03, 111.12, 67.83, 64.57, 34.32, 31.96, 29.68, 29.45, 29.39, 26.43, 26.25, 22.73, 14.17

HRMS (ESI-TOF [M+Na]$^+$): C$_{27}$H$_{38}$NaO$_4^+$ calc'd 449.2662; found 449.2661.

Elemental analysis: calc'd C, 76.02%; H, 8.98%; N, 0.00% (C$_{27}$H$_{38}$O); found C, 75.80%; H, 8.69%; N, 0.00%.

Synthesis of Intermediate 9-2

[Formula 45]

Intermediate 9-2

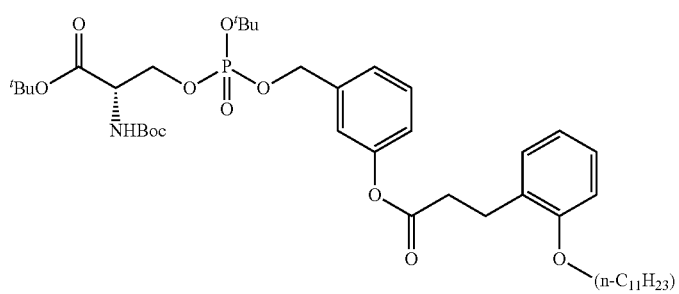

To remove the contained water, phosphoramidite 13 (164.3 mg, 0.3639 mmol) was dissolved in dichloromethane and toluene and, thereafter, the solvents were distilled off under vacuum. To the resulting residue, intermediate 9-1 (119.4 mg, 0.2799 mmol) was added and following the addition of dichloromethane and toluene, the solvents were distilled off under vacuum. In an argon atmosphere, the residue was dissolved in dichloromethane (1 mL) and a solution of 1H-tetrazole (58.8 mg, 0.8397 mmol) in THF (1 mL) was added at room temperature. A white powder precipitated in a few seconds. The liquid reaction mixture, after being stirred at room temperature for 24 hours, was diluted with dichloromethane (10 ml) and a saturated aqueous $NaHCO_3$ solution (10 ml) was added to quench the reaction, followed by three extractions with dichloromethane (8 ml×3). The organic layers were combined, dried with magnesium sulfate, and the solvent was distilled off. The residue was purified by column chromatography (hexane:ethyl acetate=4:1-2:1) to give a trivalent phosphoric acid ester intermediate (143.1 mg, 0.1811 mmol, 64.7%). The resulting intermediate was dissolved in dichloromethane (1.5 ml) in an argon atmosphere. Then, tert-butylhydroperoxide (TBHP's decane solution (5.0-6.0 M, 0.0724 mL, 0.3620 mmol)) was added at room temperature and stirring was also conducted at room temperature for 2 hours. The solvents in the resulting solution were distilled off and the residue was purified by column chromatography (hexane:ethyl acetate=2:1, hexane:acetone=4:1) to give the titled compound (100.2 mg, 0.1243 mmol, 68.7% (2 steps: 44.4%), colorless oil).

$^1$H NMR (CDCl$_3$): δ (ppm): δ=7.362-7.317 (m, 1H), 7.228-7.172 (m, 3H), 7.042-7.038 (m, 1H), 6.987-6.964 (m, 1H), 6.893-6.837 (m, 2H), 5.500-5.444 (m, 1H), 5.043-4.944 (2H), 4.363-4.314 (m, 2H), 4.241-4.180 (m, 1H), 4.031-3.931 (m, 2H), 3.054 (t, J=7.6 Hz, 2H), 2.888-2.850 (m, 2H), 1.848-1.778 (m, 2H), 1.520-1.398 (m, 29H), 1.385-1.250 (m, 14H), 0.917-0.817 (m, 3H)

$^{13}$C NMR (CDCl$_3$): δ (ppm): δ=171.72, 168.34, 157.04, 155.25, 150.89, 137.69, 137.65, 137.61, 137.57, 130.15, 129.46, 128.42, 127.76, 124.80, 121.62, 120.88, 120.23, 111.07, 84.04, 83.97, 82.67, 82.66, 79.89, 68.26, 68.23, 68.21, 68.18, 67.77, 67.56, 67.49, 67.43, 54.46, 54.38, 34.24, 31.90, 29.81, 29.76, 29.61, 29.38, 29.33, 28.31, 27.94, 26.35, 26.18, 22.67, 14.11

$^{31}$P NMR (CDCl$_3$): δ (ppm): δ=−5.63, −5.82

HRMS (ESI-TOF [M+Na]$^+$): C$_{43}$H$_{68}$NNaO$_{11}$P$^+$ calc'd 828.4422; found 828.4403.

Elemental analysis: calc'd C, 63.58%; H, 8.38%; N, 1.72% (C$_{43}$H$_{68}$NO$_{11}$P+CH$_2$Cl$_2$×0.1); found C, 63.61%; H, 8.31%; N, 1.70%.

Synthesis of Compound 9

[Formula 46]

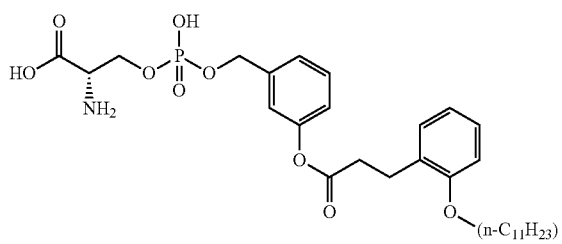

Compound 9

Protected intermediate 9-2 (90.1 mg, 0.1141 mmol) was dissolved in TFA (2 mL) and after stirring the mixture at room temperature for 2 hours, the solvent was distilled off. The residue was purified by column chromatography (chloroform:methanol:water=65:25:4) to give the titled compound (60.1 mg, 0.0861 mmol, 75.4%, white powder).

$^1$H NMR (CDCl$_3$): δ (ppm): δ=7.401-7.362 (m, 1H), 7.258-7.214 (m, 2H), 7.149 (dd, 1H, J=7.6 Hz, 1.6 Hz), 6.977 (m, 1H), 6.925-6.874 (m, 3H), 4.986-4.960 (m, 2H), 4.263 (m, 2H), 4.228 (m, 1H), 4.022 (t, 2H, J=6.8 Hz), 3.085-3.049 (m, 2H), 2.984-2.949 (m, 2H), 1.854-1.783 (m, 2H), 1.507-1.434 (m, 2H), 1.372-1.255 (m, 14H), 0.888-0.953 (m, 3H)

$^{31}$P NMR (CDCl$_3$): δ (ppm): δ=−2.40

HRMS (ESI-TOF [M-H]$^-$): C$_{30}$H$_{143}$NO$_9$P$^-$ calc'd 592.2681; found 592.2709.

Elemental analysis: calc'd C, 53.79%; H, 6.28%; N, 1.95% (C$_{30}$H$_{44}$NO$_9$P+CF$_3$CO$_2$H×1.1); found C, 53.97%; H, 7.47%; N, 2.08%.

Example 10

Synthesis of O-(hydroxy((3-((3-(2-((3-phenoxybenzyl)oxy)phenyl)propanoyl)oxy)benzyl)oxy)phosphoryl)-L-serine

[Formula 47]

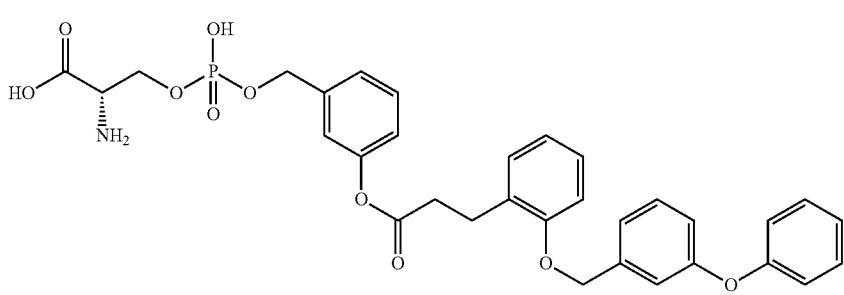

Compound 10

Synthesis of Intermediate 10-1

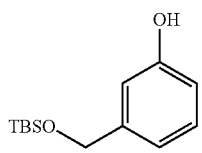

Intermediate 10-1

A solution prepared by dissolving 3-hydroxybenzyl alcohol (100.0 mg, 0.8055 mmol) and imidazole (60.3 mg, 0.8861 mmol) in anhydrous dichloromethane (2 mL), a solution of TBSCl (133.6 mg, 0.8861 mmol) in THF (3 mL) was added at 0° C., followed by stirring at room temperature for 2.5 hours. To the resulting solution, water (10 mL) was added to quench the reaction and the aqueous layer was separated, followed by two extractions with dichloromethane (10 mL×2). The organic layers were combined, dried with sodium sulfate, and the solvent was distilled off. The residue was purified by column chromatography (hexane: ethyl acetate=2:1-1:1-1:2) to give the titled compound (136.8 mg, 0.5738 mmol, 71.3%, colorless oil).

$^1$H NMR (CDCl$_3$): δ (ppm): δ=7.067-7.028 (m, 1H), 6.753-6.711 (m, 2H), 6.589-6.564 (m, 1H), 5.836 (bs, 1H), 4.584 (s, 2H), 0.835 (s, 9H), 0.000 (s, 6H)$^{13}$C NMR (CDCl$_3$): δ (ppm): δ=155.67, 143.06, 129.50, 118.41, 114.08, 113.22, 64.92, 26.02, 18.50, −5.19

HRMS (ESI-TOF [M-H]$^-$): C$_{13}$H$_{21}$O$_2$Si$^-$ calc'd 237.1316; found 237.1343.

Elemental analysis: calc'd C, 65.05%; H, 9.26%; N, 0.00% (C$_{13}$H$_{22}$O$_2$Si+H$_2$O×0.1); found C, 64.96%; H, 9.03%; N, 0.00%.

Synthesis of Intermediate 10-2

[Formula 49]

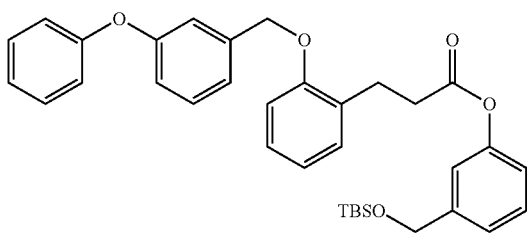

Intermediate 10-2

To a solution of intermediate 10-1 (61.9 mg, 0.2596 mmol) and compound 15 (90.5 mg, 0.2596 mmol) in dichloromethane (1 mL), EDCl/HCl (64.7 mg, 0.3375 mmol) and DMAP (9.5 mg, 0.0779 mmol)) were added, followed by stirring at room temperature for 70 minutes. The resulting solution was diluted with water (5 mL) and the aqueous layer was separated, followed by three extractions with dichloromethane (5 mL×3). The organic layers were combined, dried with sodium sulfate, and the solvent was distilled off. The residue was purified by column chromatography (hexane:ethyl acetate=10:1-8:1) to give the titled compound (111.7 mg, 0.2059 mmol, 79.3%, colorless oil).

$^1$H NMR (CDCl$_3$): δ (ppm): δ=7.245-7.053 (m, 8H), 7.018-6.976 (m, 2H), 6.931-6.900 (m, 2H), 6.880-6.832 (m, 2H), 6.816-6.755 (m, 3H), 4.967 (s, 2H), 4.614 (s, 2H), 2.994 (t, 2H, J=7.6 Hz), 2.755 (t, 2H, J=7.6 Hz), 0.847 (s, 9H), 0.000 (s, 6H)

$^{13}$C NMR (CDCl$_3$): δ (ppm): δ=171.81, 157.82, 156.82, 156.54, 150.86, 143.29, 139.34, 130.43, 130.15, 130.02, 129.88, 129.16, 128.86, 127.85, 123.58, 123.24, 121.63, 120.98, 120.09, 119.30, 119.19, 118.00, 117.14, 111.72, 69.43, 64.51, 34.34, 26.40, 26.04, 18.48, −5.18

HRMS (ESI-TOF [M+Na]$^+$): C$_{35}$H$_{40}$NaO$_5$Si$^+$ calc'd 591.2537; found 591.2538.

Elemental analysis: calc'd C, 73.91%; H, 7.09%; N, 0.00%; found C, 73.71%; H, 6.81%; N, 0.00%.

Synthesis of Intermediate 10-3

[Formula 50]

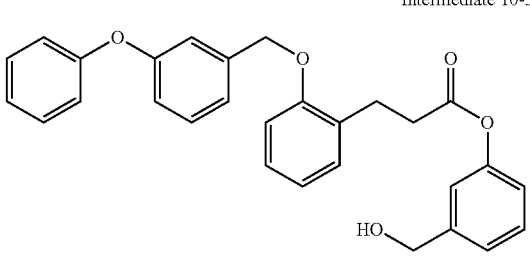

Intermediate 10-3

To a solution of intermediate 10-2 in a mixture of THF (1 mL) and pyridine (283.2 μL), HF·pyridine (115.0 μL) was added dropwise, followed by stirring for 2 hours.

The resulting solution was diluted with water (7 mL) and dichloromethane (7 mL) and the aqueous layer was separated, followed by extraction with dichloromethane (7 mL×2). The organic layers were combined, dried with magnesium sulfate, and the solvent was distilled off. The residue was purified by column chromatography (hexane: ethyl acetate=2:1) to give the titled compound (79.8 mg, 0.1756 mmol, 90.6%, white solids).

$^1$H NMR (CDCl$_3$): δ (ppm): δ=7.253-7.183 (m, 4H), 7.145-7.056 (m, 4H), 7.028-6.986 (m, 2H), 6.930-6.786 (m, 7H), 4.979 (s, 2H), 4.512 (s, 2H), 2.992 (t, 2H, J=7.6 Hz), 2.760 (t, 2H, J=7.6 Hz), 1.902 (bs, 1H).

$^{13}$C NMR (CDCl$_3$): δ (ppm): δ=171.93, 157.77, 156.90, 156.51, 150.92, 142.74, 139.30, 130.43, 130.00, 129.86, 129.48, 128.74, 127.87, 124.07, 123.56, 121.62, 120.96, 120.69, 120.02, 119.26, 117.97, 117.15, 111.71, 69.41, 64.65, 34.28, 26.39.

HRMS (ESI-TOF [M+Na]$^+$): C$_{29}$H$_{26}$NaO$_5$$^+$ calc'd 477.1672; found 477.1678.

Elemental analysis: calc'd C, 74.35%; H, 6.08%; N, 0.00% (C$_{29}$H$_{26}$O$_5$+ethyl acetate 0.6); found C, 74.05%; H, 5.73%; N, 0.00%.

Synthesis of Intermediate 10-4

[Formula 51]

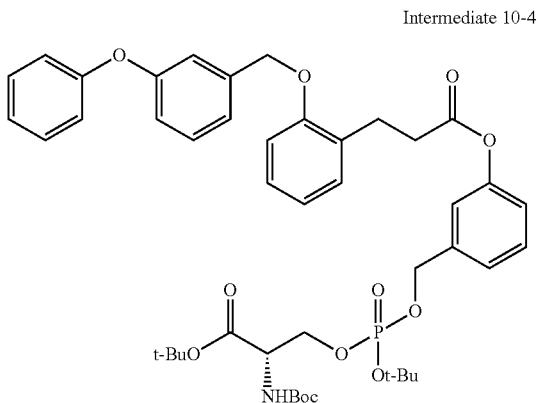

Intermediate 10-4

To remove the contained water, phosphoramidite 13 (99.2 mg, 0.2197 mmol) was dissolved in dichloromethane and toluene and, thereafter, the solvents were distilled off under vacuum. To the resulting residue, intermediate 10-3 (76.8 mg, 0.1690 mmol) was added and following the addition of dichloromethane and toluene, the solvents were distilled off under vacuum. In an argon atmosphere, the residue was dissolved in dichloromethane (0.8 mL) and a solution of 1H-tetrazole (29.6 mg, 0.4224 mmol) in THF (0.8 mL) was added at room temperature. A white powder precipitated in a few seconds. The liquid reaction mixture, after being stirred at room temperature for 22 hours, was diluted with dichloromethane (8 ml) and a saturated aqueous NaHCO₃ solution (8 ml) was added to quench the reaction, followed by two extractions with dichloromethane (8 ml×2). The organic layers were combined, dried with magnesium sulfate, and the solvent was distilled off. The residue was purified by column chromatography (hexane:ethyl acetate=4:1) to give a trivalent phosphoric acid ester intermediate (123.9 mg, 0.1515 mmol, 89.6%). The resulting intermediate was dissolved in dichloromethane (1.2 ml) in an argon atmosphere. Then, tert-butylhydroperoxide (TBHP's decane solution (5.0-6.0 M, 0.075 mL, 0.3030 mmol)) was added at room temperature and stirring was also performed at room temperature for 80 minutes. The solvents in the resulting solution were distilled off and the residue was purified by column chromatography (hexane:ethyl acetate=4:1-1:1) to give the titled compound (119.8 mg, 0.1437 mmol, 94.8% (2 steps: 85%), colorless oil).

¹H NMR (CDCl₃): δ (ppm): δ=7.353-7.298 (m, 4H), 7.242-7.166 (m, 4H), 7.122-7.080 (m, 2H), 7.026-6.993 (m, 3H), 6.964-6.884 (m, 4H), 5.523-5.469 (m, 1H), 5.084 (s, 2H), 5.041-4.943 (m, 2H), 4.372-4.284 (m, 2H), 4.258-4.191 (m, 1H), 3.086 (t, 2H, J=7.6 Hz), 2,860 (t, 2H J=7.6 Hz), 1.476-1.433 (m, 27H)

¹³C NMR (CDCl₃): δ (ppm): δ=171.60, 168.36, 157.74, 156.86, 156.46, 155.27, 150.86, 139.26, 130.39, 129.96, 129.82, 129.50, 128.67, 127.85, 124.84, 123.52, 121.64, 121.57, 120.92, 120.87, 119.21, 117.94, 117.08, 111.68, 4.09, 84.02, 82.69, 82.67, 79.91, 69.37, 68.21, 67.53, 54.48, 34.20, 29.81, 29.78, 28.33, 27.96, 26.32.

³¹P NMR (CDCl₃): δ (ppm): S=−5.63, −5.82

HRMS (ESI-TOF [M+Na]⁺): C₄₅H₅₀NNaO₁₂P⁺ calc'd 856.3432; found 856.3405.

Elemental analysis: calc'd C, 63.83%; H, 6.64%; N, 1.65% (C₄₅H₅₀NO₁₂P+0.2CH₂Cl₂); found C, 63.73%; H, 6.69%; N, 1.63%.

Synthesis of Compound 10

[Formula 52]

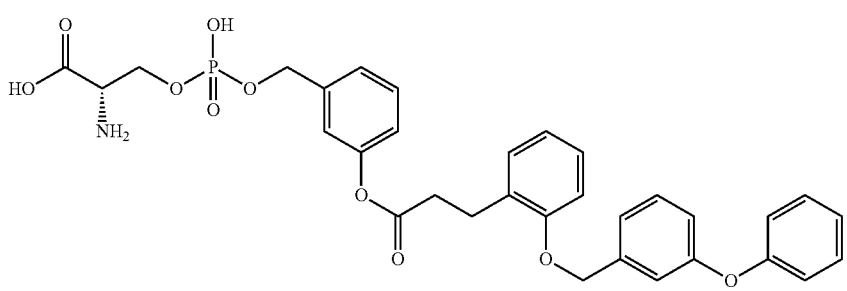 [SMILES: N[C@@H](COP(=O)(O)OCc1cccc(OC(=O)CCc2ccccc2OCc2cccc(Oc3ccccc3)c2)c1)C(=O)O]

Compound 10

Protected intermediate 10-4 (113.9 mg, 0.1366 mmol) was dissolved in TFA (2 mL) and after stirring the mixture at room temperature for 4 hours, the solvent was distilled off. The residue was purified by column chromatography (chloroform:methanol:water=65:25:4) to give the titled compound (74.7 mg, 0.1202 mmol, 88.1%, white powder).

¹H NMR (CDCl₃): δ (ppm): δ=7.389-7.317 (m, 4H), 7.266-7.228 (m, 2H), 7.193-7.120 (m, 4H), 7.014-6.944 (m, 6H), 6.875-6.855 (m, 1H), 5.130 (s, 2H), 4.990-4.971 (m, 2H), 4.304-4.266 (m, 3H), 3.123-3.087 (m, 2H), 2.982-2.946 (m, 2H)

³¹P NMR (CDCl₃): δ (ppm): δ=−2.27

HRMS (ESI-TOF [M-H]⁻): C₃₂H₃₁NO₁₀P⁻ calc'd 620.1691; found 620.1697.

Elemental analysis: calc'd C, 43.39%; H, 3.22%; N, 1.23% (C₃₂H₃₂NO₁₀P+4.5 CF₃CO₂H); found C, 43.18%; H, 3.40%; N, 1.31%.

m.p. 197-208° C.

Example 11

Synthesis of O-(hydroxy((4-((3-(2-(undecyloxy)phenyl)propanoyl)oxy)benzyl)oxy)phosphoryl)-L-serine

[Formula 53]

Compound 11

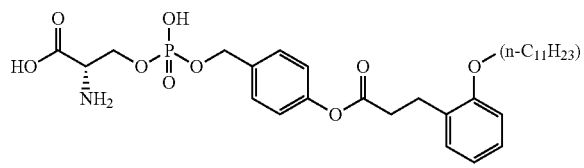

Synthesis was performed by the same method as in Example 9 except that 3-(tert-butyldimethylsilyloxymethyl) phenol was replaced by 4-(tert-butyldimethylsilyloxymethyl)phenol; in the final step, purification was conducted by column chromatography (chloroform:methanol:water=65:25:4) to give the titled compound (23 mg, 0.0387 mmol, 44.23%, white powder).

$^1$H NMR (CDCl$_3$): δ (ppm): δ=7.448 (m, 2H), 7.240 (m, 1H), 7.178-7, 164 (m, 1H), 7.009-6.872 (m, 4H), 5.053-5.032 (m, 2H), 4.462-4.246 (m, 3H), 4.043 (m, 2H), 3.097-3.082 (m, 2H), 3.022-2.988 (m, 2H), 1.831 (m, 2H), 1.482 (m, 2H), 1.261 (m, 14H), 0.871 (m, 3H)

$^{31}$P NMR (CDCl$_3$): δ (ppm): δ=−1.75.

HRMS (ESI-TOF [M-H]$^−$): C$_{30}$H$_{43}$NO$_9$P$^−$ calc'd 592.2681; found 592.2692.

Example 12

Synthesis of O-(hydroxy((4-((3-(2-(undecyloxy)phenyl)propanoyl)oxy)but-2-yn-1-yl)oxy)phosphoryl)-L-serine

[Formula 54]

Compound 12

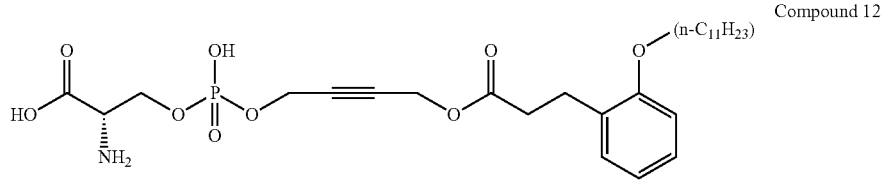

Synthesis of Intermediate 12-1

[Formula 55]

Intermediate 12-1

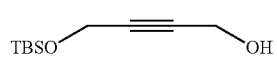

A solution prepared by dissolving 1,4-butynediol (85.1 mg, 0.989 mmol) and imidazole (88.2 mg, 1.296 mmol) in anhydrous DMF (3 mL), TBSCl (149.5 mg, 0.992 mmol) was added at 0° C., followed by stirring at room temperature for 11 hours. To the resulting solution, water (30 mL) was added to quench the reaction and the aqueous layer was separated, followed by three extractions with ethyl acetate (20 mL×3). The organic layers were combined, dried with sodium sulfate, and the solvent was distilled off. The residue was purified by column chromatography (hexane:ethyl acetate=4:1) to give the titled compound (88.0 mg, 0.439 mmol, 44%, colorless oil).

$^1$H-NMR (CDCl$_3$): δ=4.347 (2H, t, J=1.8 Hz), 4.291 (2H, t, J=1.6 Hz), 1.735 (1H, brs), 0.906 (9H, s), 0.116 (6H, s).

$^{13}$C-NMR (CDCl$_3$): δ=84.42, 82.98, 51.71, 51.16, 25.80, 18.30, −5.20.

HRMS (ESI-TOF, [M+Na]$^+$): C$_{10}$H$_{20}$NaO$_2$Si$^+$ calc'd: 223.1125; found: 223.1125.

Synthesis of Intermediate 12-2

[Formula 56]

Intermediate 12-2

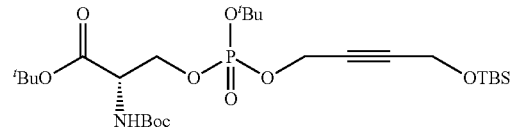

To remove the contained water, phosphoramidite 13 (218.3 mg, 0.470 mmol) was dissolved in dichloromethane and toluene and, thereafter, the solvents were distilled off under vacuum. To the resulting residue, intermediate 12-1 (94.6 mg, 0.472 mmol) was added and following the addition of dichloromethane and toluene, the solvents were distilled off under vacuum. In an argon atmosphere, the residue was dissolved in dichloromethane (2.4 mL) and a solution of 1H-tetrazole (67.6 mg, 0.965 mmol) in THF (2.4 mL) was added at 0° C. A white powder precipitated in a few seconds. The liquid reaction mixture was stirred at 0° C. for 4 hours and after adding tert-butylhydroperoxide (TBHP's decane solution (5.0-6.0 M, 197 µL, 0.985 mmol)) at room temperature, stirring was further conducted at 0° C. for 4 hours. The resulting solution was diluted with water (20 mL), followed by three extractions with dichloromethane (20 mL×3). The organic layers were combined, washed with saline, dried with sodium sulfate, and the solvent was distilled off. The residue was purified by column chromatography (hexane:ethyl acetate=5:1-4:1) to give the titled compound (167.0 mg, 0.288 mmol, 61%, colorless oil).

$^1$H-NMR (CDCl$_3$): δ=5.468 (1H, t, J=7.2 Hz), 4.651 (2H, m), 4.388-4.351 (4H, m), 4.242 (1H, m), 1.506-1.452 (27H, m), 0.904 (9H, s), 0.114 (6H, s).

$^{13}$C-NMR (CDCl$_3$): δ=168.30, 155.25, 86.32, 84.42, 84.35, 82.73, 82.72, 79.95, 78.82, 78.78, 78.73, 78.69, 67.62, 67.56, 67.50, 55.26, 55.22, 55.19, 54.45, 54.41, 54.38, 54.33, 51.60, 29.79, 29.78, 29.75, 29.73, 28.30, 27.94, 25.77, 18.25, −5.22.

$^{31}$P-NMR (CDCl$_3$): δ=−5.84, −5.99.

HRMS (ESI-TOF, [M+Na]$^+$): C$_{26}$H$_{50}$NNaO$_9$PSi$^+$ calc'd: 602.2885; found: 602.2859.

Synthesis of Intermediate 12-3

[Formula 57]

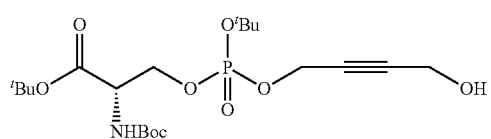
Intermediate 12-3

To a solution of intermediate 12-2 in methanol (7 mL), Amberlyst (registered trademark) was added at 0° C., followed by stirring at room temperature for 5 hours. The resulting solution was filtered over a Celite (registered trademark) pad and the solvent in the resulting filtrate was distilled off. The residue was purified by column chromatography (hexane:ethyl acetate=2:1-1:1-1:2) to give the titled compound (70.6 mg, 0.152 mmol, 53%, colorless oil).

$^1$H-NMR (CDCl$_3$): δ=5.552 (1H, t, J=9.4 Hz), 4.741-4.576 (2H, m), 4.415-4.203 (5H, m), 3.034 (1H, brs), 1.486 (27H, m).

$^{13}$C-NMR (CDCl$_3$): δ=168.54, 168.46, 155.30, 155.25, 86.72, 86.70, 84.56, 84.48, 82.95, 80.18, 80.14, 79.30, 79.28, 79.23, 79.21, 79.15, 79.12, 67.46, 67.40, 67.35, 67.30, 55.25, 55.20, 54.42, 54.33, 54.25, 50.53, 29.73, 29.69, 28.24, 27.88.

$^{31}$P-NMR (CDCl$_3$): δ=−5.77, −5.84.

HRMS (ESI-TOF, [M+Na]$^+$): C$_{20}$H$_{36}$NNaO$_9$P$^+$ calc'd: 488.2020; found: 488.2019.

Synthesis of Intermediate 12-4

[Formula 58]

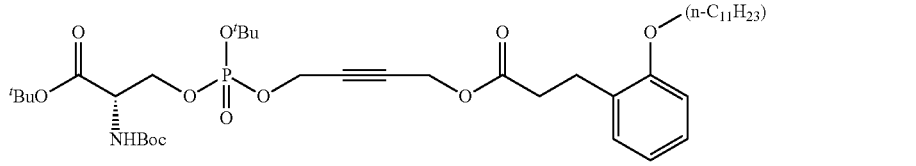
Intermediate 12-4

To a solution of intermediate 12-3 (34.6 mg, 0.074 mmol), compound 14 (35.3 mg, 0.110 mmol) and EDCl/HCl (28.2 mg, 0.0.147 mmol) in dichloromethane (0.5 mL), 4-dimethylaminopyridine (DMAP) (7.7 mg, 0.063 mmol) was added, followed by stirring at room temperature for 15 hours. To the liquid reaction mixture, methanol (0.2 mL) and 1-ethyl-3-(3-dimethylaminopropyl)carbodiimide (EDCI) (21.2 mg, 0.111 mmol) were added, followed by stirring at room temperature for 20 hours. To the resulting solution, water (8 mL) was added to quench the reaction and the aqueous layer was separated, followed by three extractions with ethyl acetate (10 mL×3). The organic layers were combined, dried with sodium sulfate, and the solvent was distilled off. The solvents in the liquid reaction mixture were distilled off and the residue was purified by column chromatography (hexane:ethyl acetate=3:1) to give the titled compound (30.7 mg, 0.040 mmol, 54%, colorless oil).

$^1$H-NMR (CDCl$_3$): δ=7.159 (2H, m), 6.845 (2H, m), 5.464 (1H, t, J=7.4 Hz), 4.722 (2H, m), 4.653 (2H, m), 4.362 (2H, m), 4.250 (1H, m), 3.956 (2H, t, J=6.4 Hz), 2.947 (2H, t, J=7.6 Hz), 2.659 (2H, m), 1.792 (2H, quintet, 7.0 Hz), 1.488 (29H, m), 1.328 (14H, m), 0.882 (3H, t, J=6.8 Hz).

$^{13}$C-NMR (CDCl$_3$): δ=172.46, 168.27, 156.95, 155.23, 129.97, 128.58, 127.60, 120.17, 111.02, 84.53, 84.49, 84.46, 82.74, 82.72, 81.84, 80.73, 80.68, 80.64, 80.60, 79.96, 67.77, 67.64, 67.59, 67.53, 55.00, 54.98, 54.95, 54.46, 54.44, 54.41, 54.38, 54.37, 54.34, 51.81, 33.81, 31.88, 29.79, 29.77, 29.74, 29.73, 29.59, 29.56, 29.34, 29.30, 28.29, 27.94, 26.11, 26.03, 22.65, 14.07.

$^{31}$P-NMR (CDCl$_3$): δ=−5.82, −5.95.

HRMS (ESI-TOF, [M+Na]$^+$): C$_{40}$H$_{66}$NNaO$_{11}$P$^+$ calc'd: 790.4266; found: 790.4278.

Synthesis of Compound 12

[Formula 59]

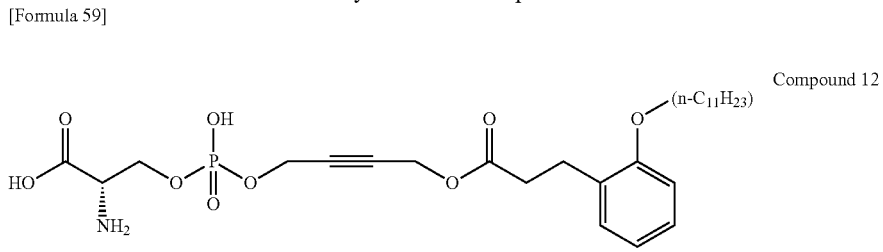
Compound 12

To a solution of protected intermediate 12-4 (30.3 mg, 0.039 mmol) in dichloromethane (0.1 mL) was dissolved in trifluoroacetic acid (TFA) (0.5 mL) at 0° C. and after stirring the mixture at room temperature for an hour, the solvents were distilled off. The residue was purified by column chromatography (chloroform:methanol:acetic acid=9:1:0-8:1:1-7:1:2) to give an acetic acid salt of the titled compound (19.0 mg, 0.034 mmol, 87%, white powder). The resulting acetic acid salt was dissolved in TFA and the solvent was distilled off, whereupon the titled compound was obtained as a TFA salt (white powder).

$^1$H-NMR (CDCl$_3$/TFA-d): δ=7.204 (1H, t, J=7.4 Hz), 7.093 (1H, d, J=6.8 Hz), 6.883 (2H, m), 4.724-4.479 (7H, m), 4.004 (2H, t, J=6.6 Hz), 2.957 (2H, t, J=7.0 Hz), 2.763 (2H, t, J=7.2 Hz), 1.795 (2H, quintet, J=6.8 Hz), 1.440 (2H, m), 1.365-1.275 (16H, m), 0.880 (3H, t, J=6.8 Hz).

$^{31}$P-NMR (CDCl$_3$/TFA-d): δ=−1.59.

HRMS (ESI-TOF, [M-H]$^-$): C$_{27}$H$_{41}$NO$_9$P$^-$ calc'd: 554.2524; found: 554.2543.

Mp: 134.0° C.-136.5° C., colorless solid cube.

Elemental analysis: C$_{27}$H$_{42}$NO$_9$P.0.4CF$_3$COOH calc'd: C, 55.54; H, 7.11; N, 2.33; found: C, 55.77; H, 7.19; N, 2.32.

Example 16

Synthesis of O-(hydroxy(4-(((3-(2-((3-phenoxybenzyl)oxy)phenyl)propanoyl)oxy)methyl)phenoxy)phosphoryl)-L-serine

[Formula 60]

Compound 16

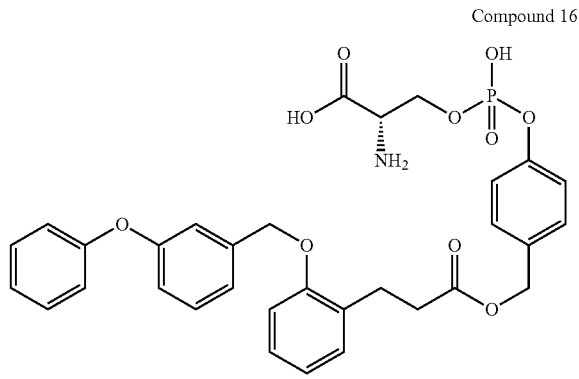

Synthesis of Intermediate 16-1

[Formula 61]

Intermediate 16-1

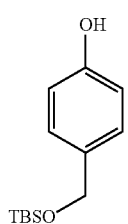

To a liquid reaction mixture prepared by adding imidazole (258.8 mg, 3.8014 mmol) to a solution of 4-hydroxybenzyl alcohol (214.5 mg, 1.7279 mmol) in THF (4 mL), a solution of TBSCl (286.5 mg, 1.9007 mmol) in THF (2 mL) was added at 0° C. in an argon atmosphere. The liquid reaction mixture was stirred at 0° C. for 10 minutes, then stirred at room temperature for 2 hours. To the resulting solution, water (7 mL) was added to quench the reaction and the aqueous layer was separated, followed by the extractions with dichloromethane (7 mL×3). The organic layers were combined, dried with magnesium sulfate, and the solvent was distilled off. The residue was purified by column chromatography (hexane:ethyl acetate=4:1-0:1) to give the titled compound (357.0 mg, 1.4975 mmol, 86.7%, colorless oil).

$^1$H NMR (CDCl$_3$): δ (ppm): δ=7.191-7.169 (m, 2H), 6.794-6.759 (m, 2H), 6.363 (brs, 1H), 4.682 (s, 2H), 0.952 (s, 9H), 0.118 (s, 6H)

$^{13}$C NMR (CDCl$_3$): δ (ppm): δ=154.95, 133.03, 127.98, 115.25, 65.02, 26.02, 18.49, −5.12

HRMS (ESI-TOF [M+Na]$^+$): C$_{13}$H$_{22}$NaO$_2$Si$^+$ calc'd 261.1281; found 261.1282.

Elemental analysis: calc'd C, 65.50%; H, 9.30%; N, 0.00% (C$_{13}$H$_{22}$O$_2$Si); found C, 65.39%; H, 9.25%; N, 0.00%.

Synthesis of Intermediate 16-2

[Formula 62]

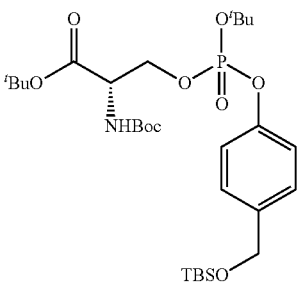

To remove the contained water, phosphoramidite 13 (130.3 mg, 0.2885 mmol) was dissolved in dichloromethane and toluene and, thereafter, the solvents were distilled off under vacuum. To the resulting residue, intermediate 16-1 (52.9 mg, 0.2219 mmol) was added and following the addition of dichloromethane (1 mL) and toluene (0.1 mL), the solvents were distilled off under vacuum. In an argon atmosphere, the residue was dissolved in dichloromethane (0.5 mL) and a solution of 1H-tetrazole (38.9 mg, 0.5547 mmol) in THF (0.6 mL) was added at room temperature. After stirring the liquid reaction mixture at room temperature for 20 hours, water (7 ml) was added to quench the reaction, followed by two extractions with dichloromethane (6 ml×2). The organic layers were combined, dried with magnesium sulfate, and the solvent was distilled off. The residue was purified by column chromatography (hexane:ethyl acetate=4:1) to give a trivalent phosphoric acid ester intermediate (141.8 mg, 0.2356 mmol, 106.2%, colorless oil). The resulting intermediate was dissolved in dichloromethane (1.5 ml) in an argon atmosphere. Then, tert-butylhydroperoxide (TBHP's decane solution (5.0-6.0 M, 0.0943 mL)) was added at room temperature and stirring was also conducted at room temperature for 70 minutes. The solvents in the resulting solution were distilled off and the residue was purified by column chromatography (hexane:ethyl acetate=4:1-2:1) to give the titled compound (114.2 mg, 0.1849 mmol, 78.5% (2 steps: 83.3%), colorless oil), $^1$H NMR (CDCl$_3$): δ (ppm): δ=7.253-7.224 (m, 2H), 7.135-7.097 (m, 2H), 5.452-5.372 (m, 1H), 4.668 (s, 2H), 4.452-4.269 (m, 3H), 1.487-2.469 (m, 9H), 1.422-1.408 (m, 18H), 0.902 (s, 9H), 0.058 (s, 6H).

$^{13}$C NMR (CDCl$_3$): δ (ppm): δ=168.18, 155.16, 149.71, 149.63, 138.00, 137.99, 127.20, 119.74, 119.72, 119.70, 119, 67, 84.90, 84.86, 84.82, 84.78, 82.74, 82.73, 79.89, 68.01, 67.95, 67.91, 64.32, 54.43, 54.39, 54.35, 54.30, 29.78, 29.77, 29.74, 29.73, 28.29, 27.90, 27.89, 25.90, 18.35, −5.29

$^{31}$P NMR (CDCl$_3$): δ (ppm): δ=−11.04, −11.35

HRMS (ESI-TOF [M+Na]$^+$): C$_{29}$H$_{52}$NNaO$_9$PSi$^+$ calc'd 640.3041; found 640.3016.

Elemental analysis: calc'd C, 56.38%; H, 8.48%; N, 2.27% (C$_{29}$H$_{52}$NO$_9$Psi); found C, 56.14%; H, 8.29%; N, 2.22%.

Synthesis of Intermediate 16-3

[Formula 63]

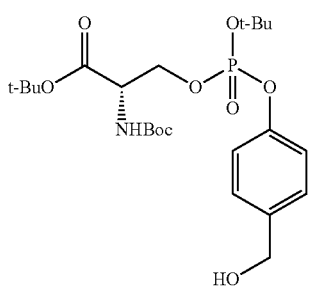

Intermediate 16-3

To a solution of intermediate 5-2 in a mixture of THF (1 mL) and pyridine (326.1 μL), HF•pyridine (132.4 μL) was added dropwise, followed by stirring for 6 hours. The resulting solution was diluted with water (10 mL) and dichloromethane (10 mL) and the aqueous layer was separated, followed by extraction with dichloromethane (10 mL×2). The organic layers were combined, dried with magnesium sulfate, and the solvent was distilled off. The residue was purified by column chromatography (hexane: ethyl acetate=2:1-ethyl acetate) to give the titled compound (53.0 mg, 0.1053 mmol, 54.8%, white solids).

$^1$H NMR (CDCl$_3$): δ (ppm): δ=7.293-7.266 (m, 2H), 7.141-7.103 (m, 2H), 5.462-5.388 (m, 1H), 4.603 (s, 2H), 4.447-4.266 (m, 3H), 2.641 (brs, 1H), 1.488-1.471 (m, 9H), 1.426-1.380 (m, 18H)

$^{13}$C NMR (CDCl$_3$): δ (ppm): δ=168.18, 155.20, 1150.06, 129.99, 137.86, 128.20, 119.99, 119.94, 85.15, 85.09, 85.02, 82.84, 82.82, 80.00, 68.12, 68.07, 68.02, 64.35, 54.38, 54.34, 54.29, 30.89, 29.79, 29.78, 29.75, 29.73, 28.29, 27.91, 27.89 $^{31}$P NMR (CDCl$_3$): δ (ppm): δ=−11.18, −11.45

HRMS (ESI-TOF [M+Na]$^+$): C$_{23}$H$_{38}$NNaO$_9$P$^+$ calc'd 526.2176; found 526.2189.

Elemental analysis: calc'd C, 54.86%; H, 7.61%; N, 2.78% (C$_{23}$H$_{38}$NO$_9$P); found C, 54.91%; H, 7.42%; N, 2.84%.

Synthesis of Intermediate 16-4

[Formula 64]

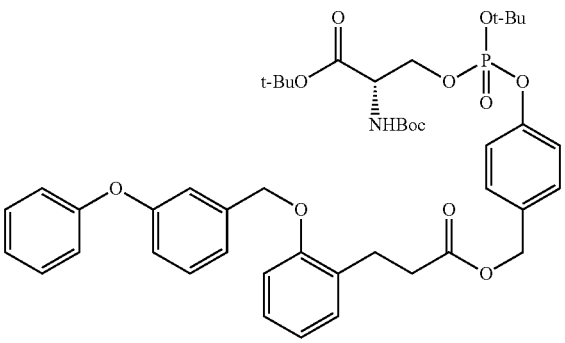 [SMILES: N[C@@H](COP(=O)(O)Oc1ccc(COC(=O)CCc2ccccc2OCc2cccc(Oc3ccccc3)c2)cc1)C(=O)O]

Intermediate 16-4

To a solution of intermediate 16-3 (49.0 mg, 0.0973 mmol) and compound 15 (37.3 mg, 0.1070 mmol) in dichloromethane (1 mL), EDCI (30.0 mg, 0.1460 mmol) and DMAP (2.4 mg, 0.0195 mmol) were added and after stirring at room temperature for 1.5 hours in an argon atmosphere, the solvent was distilled off. To the resulting solution, water (10 mL) was added to quench the reaction and the aqueous layer was subjected to two extractions with dichloromethane (10 ml×2). The organic layers were combined, dried with magnesium sulfate, and the solvent was distilled off. The residue was purified by column chromatography (hexane: ethyl acetate=1:1) to give the titled compound (57.7 mg, 0.0692 mmol, 71.1%, colorless oil).

$^1$H NMR (CDCl$_3$): δ (ppm): δ=7.270-7.213 (m, 3H), 7.181-7.145 (m, 2H), 7.106-6.979 (m, 7H), 6.941-6.911 (m, 2H), 6.811-6.764 (m, 2H), 5.391-5.315 (m, 1H), 5.003-4.919 (m, 4H), 4.401-4.201 (m, 3H), 2.902 (t, 2H, J=7.6 Hz), 2.571 (t, 2H, J=7.6 Hz), 1.440-1.424 (m, 9H), 1.368-1.353 (m, 18H)

$^{13}$C NMR (CDCl$_3$): δ (ppm): δ=173.01, 168.18, 157.67, 156.89, 156.38, 155.19, 150.66, 150.60, 139.28, 132.71, 130.19, 129.92, 129.80, 129.65, 128.99, 127.63, 123.48, 121.54, 120.86, 120.05, 120.00, 119.16, 117.94, 117.08, 111.59, 85.104, 82.84, 79.99, 69.31, 68.11, 65.37, 54.40, 34.14, 29.82, 29.78, 28.32, 27.94, 27.92, 26.19.

$^{31}$P NMR (CDCl$_3$): δ (ppm): δ=−11.15, −11.46

HRMS (ESI-TOF [M+Na]$^+$): C$_{45}$H$_{56}$NNaO$_{12}$P$^+$ calc'd 856.3432; found 856.3409.

Synthesis of Compound 16

[Formula 65]

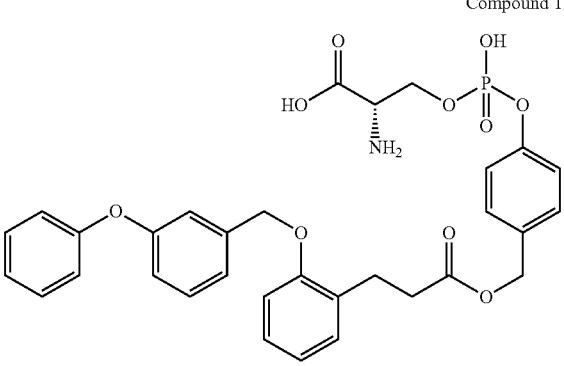

Compound 16

Intermediate 16-4 (48.6 mg, 0.0583 mmol) was dissolved in TFA (1 mL) at 0° C. and after stirring at 0° C. for 40 minutes, then at room temperature for 50 minutes, the solvent was distilled off. The residue was purified by column chromatography (chloroform:methanol:water=65:25:4) to give the titled compound (22.6 mg, 0.0364 mmol, 62.4%, white powder).

$^1$H NMR (CDCl$_3$): δ (ppm): δ=7.345-7.305 (m, 3H), 7.254-7.185 (m, 2H), 7.167-7.100 (m, 3H), 7.066-6.951 (m, 7H), 6.899-6.855 (m, 2H), 5.063 (m, 4H), 4.713 (m, 2H), 3.503 (m, 1H), 2.966 (t, 2H, J=7.6 Hz), 2.729 (t, 2H, J=7.6 Hz)

$^{31}$P NMR (CDCl$_3$): δ (ppm): δ=−6.43

HRMS (ESI-TOF [M-H]$^-$): $C_{32}H_{31}NO_{10}P^-$ calc'd 620.1691; found 620.1719.

Elemental analysis: calc'd C, 55.52%; H, 4.52%; N, 1.90% ($C_{32}H_{32}NO_{10}P+CF_3CO_2H$*1); found C, 55.74%; H, 4.76%; N, 1.94%.

Example 17

Synthesis of O-(hydroxy((3-(((3-(2-(undecyloxy) phenyl)propanoyl)oxy)methyl)benzyl)oxy)phosphoryl)-L-serine

[Formula 66]

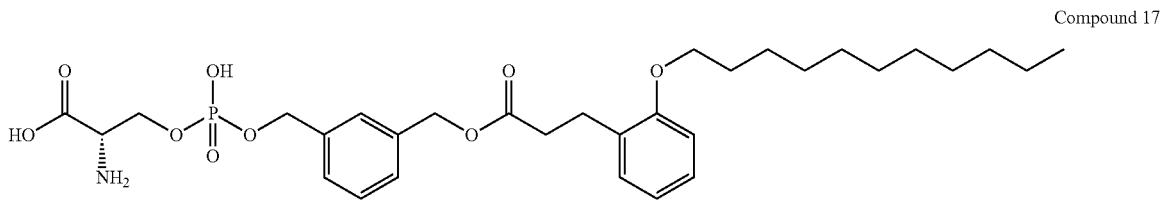

Compound 17

Synthesis of Intermediate 17-1

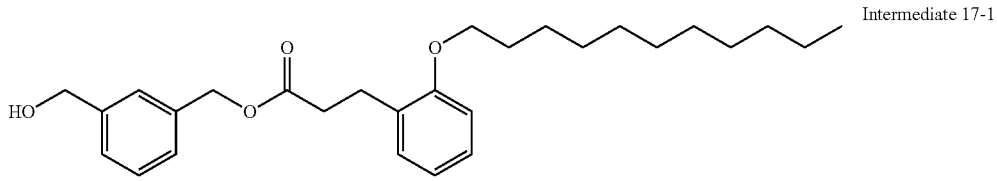

Intermediate 17-1

To a solution of 1,3-benzenedimethanol (82.5 mg, 0.5971 mmol) and compound 14 (191.2 mg, 0.5971 mmol) in dichloromethane (5 mL), EDCl/HCl (228.9 mg, 1.1942 mmol) and DMAP (14.6 mg 0.1194 mmol)) were added, followed by stirring at room temperature for an hour in an argon atmosphere. The solvent was distilled off and the residue was purified by column chromatography (hexane: ethyl acetate=4:1-2:1) to give the titled compound 17-1 (112.7 mg, 0.2558 mmol, 42.84%, colorless oil).

$^1$H NMR (CDCl$_3$): δ (ppm): S=7.392-7.334 (m, 3H), 7.297-7.255 (m, 1H), 7.227-7.144 (m, 2H), 6.891-6.847 (m, 2H), 5.136 (m, 2H), 4.704 (d, 2H, J=4.4 Hz), 3.987 (t, 2H, J=6.8 Hz), 3.008 (t, 2H, J=7.6 Hz), 2.719 (t, 2H, J=7.6 Hz), 2.157 (m, 1H), 1.831 (m, 2H), 1.538-1.466 (m, 2H), 1.404-1.278 (m, 13H), 0.949-0.915 (t, 3H, J=6.8 Hz).

$^{13}$C NMR (CDCl$_3$): δ (ppm): δ=173.31, 157.00, 141.34, 136.45, 129.97, 128.82, 128.74, 127.55, 127.28, 126.67, 126.61, 120.20, 111.05, 67.80, 66.00, 65.01, 34.21, 31.95, 29.65, 29.62, 29.39, 29.38, 29.35, 26.22, 26.17, 22.71, 14.15

HRMS (ESI-TOF [M+Na]$^+$): $C_{28}H_{40}NaO_4^+$ calc'd 463.2819; found 463.2817.

Synthesis of Intermediate 17-2

[Formula 67]

Intermediate 17-2

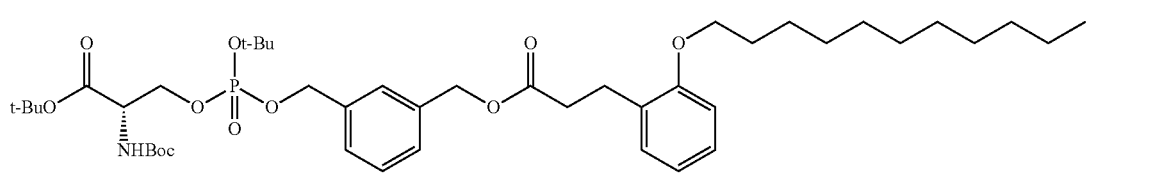

Phosphoramidite 13 (87.9 mg, 0.1947 mmol) and intermediate 17-1 (57.2 mg, 0.1298 mmol) were dissolved in dichloromethane (1.5 mL) and toluene (0.1 mL) and the solvents were distilled off. In an argon atmosphere, the residue was dissolved in dichloromethane (0.6 mL) and a solution of 1H-tetrazole (22.7 mg, 0.3245 mmol) in tetra- HRMS (ESI-TOF [M+Na]$^+$): $C_{44}H_{70}NNaO_{11}P^+$ calc'd 842.4579; found 842.4560.

Elemental analysis: calc'd C, 64.45%, H, 8.60%, N, 1.71% ($C_{44}H_{70}NO_{11}P$); found C, 64.30%, H, 8.31%, N, 1.73%.

Synthesis of Compound 17

[Formula 68]

Compound 17

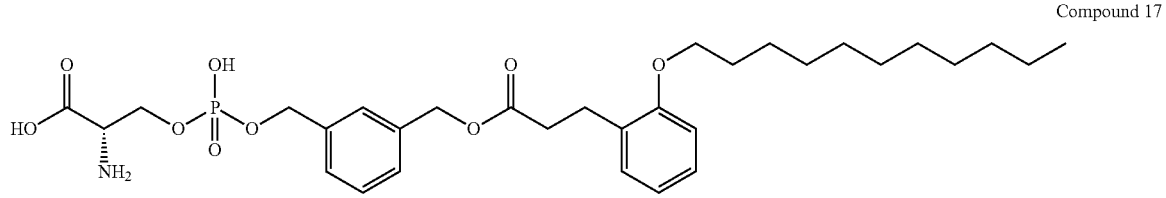

hydrofuran (THF) (0.7 mL) was added at room temperature. The liquid reaction mixture was stirred at room temperature for 19 hours and a saturated aqueous NaHCO$_3$ solution (15 ml) was added to quench the reaction, followed by three extractions with dichloromethane (10 ml×3). The organic layers were combined, dried with magnesium sulfate, and the solvent was distilled off. The residue was purified by column chromatography (hexane:ethyl acetate=2:1-1:1) and the solvents were distilled off to give a trivalent phosphodiester compound (9.0 mg, 0.1107 mmol, 85.28%, colorless oil). The resulting compound was dissolved in dichloromethane (1 ml) in an argon atmosphere. Then, tert-butylhydroperoxide (TBHP's decane solution (5.0-6.0 M, 0.0443 mL)) was added at room temperature and after stirring at room temperature for an hour, the solvent was distilled off. The residue was purified by column chromatography (hexane:ethyl acetate=2:1-1:1) to give the titled compound 17-2 (81.3 mg, 0.0991 mmol, 89.56% (2 steps: 76.35%), white solids).

$^1$H NMR (CDCl$_3$): δ (ppm): δ=7.368-7.323 (m, 2H), 7.300 (m, 1H), 7.247-7.260 (m, 1H), 7.178-7.101 (m, 2H), 6.842-6.801 (m, 5.477-5.423 (m, 1H), 5.101 (s, 2H), 5.069-4.955 (m, 2H), 4.363-4.291 (m, 2H), 4.249-4.182 (m, 1H), 3.942 (t, 2H, J=6.4 Hz), 2.959 (t, 2H, J=7.6 Hz), 2.672 (t, 2H, J=7.6 Hz), 1.814-1.744 (m, 2H), 1.630-1.426 (m, 29H), 1.350-1.231 (m, 14H), 0.873 (t, 3H, J=6.8 Hz)

$^{13}$C NMR (CDCl$_3$): δ (ppm): δ=173.12, 168.34, 156.97, 155.24, 136.54, 136.44, 136.40, 136.37, 136.33, 129.94, 128.94, 128.78, 128.05, 127.54, 127.47, 127.38, 120.17, 111.03, 83.93, 83.86, 82.66, 82.64, 79.91, 68.70, 68.64, 67.76, 67.45, 67.40, 65.75, 65.74, 54.48, 54.43, 34.15, 31.89, 29.81, 29.80, 29.77, 29.76, 29.60, 29.57, 29.35, 29.32, 28.31, 28.09, 27.95, 27.93, 26.18, 26.13, 22.66, 14.10

$^{31}$P NMR (CDCl$_3$): δ (ppm): δ=−5.61, −5.75

A solution of protected intermediate 17-2 (74.8 mg, 0.0912 mmol) in TFA (2 mL) was stirred at 0° C. for 10 minutes and after further stirring at room temperature for 1.5 hours, the solvent was distilled off. The residue was purified by column chromatography (chloroform:methanol:water=65:25:4) to give the titled compound (51.1 mg, 0.0841 mmol, 91.21%, white powder). The resulting acetic acid salt was dissolved in TFA and the solvent was distilled off to give the titled compound as a TFA salt (white powder).

$^1$H NMR (CDCl$_3$): δ (ppm): δ=7.390-7.372 (m, 1H), 7.325-7.280 (m, 3H), 7.252-7.135 (m, 1H), 7.035-7.018 (m, 1H), 6.904-6.833 (m, 2H), 5.170 (s, 2H), 5.070 (s, 2H), 4.427 (m, 3H), 4.007 (t, 2H, J=6.6 Hz), 2.970 (t, 2H, J=7.4 Hz), 2.785 (t, 2H, J=7.4 Hz), 1.828 (m, 2H), 1.446-1.411 (m, 2H), 1.338-1.257 (m, 14H), 0.876 (t, 3H, J=6.8 Hz)

$^{13}$P NMR (CDCl$_3$): δ (ppm): δ=−1.45

HRMS (ESI-TOF [M-H]$^−$): $C_{31}H_{45}NO_9P^−$ calc'd 606.2837; found 606.2831.

The synthesis methods for the amino acid site linked phosphate site (phosphoramidite) and side chain site which are used in the present invention are illustrated by the following schemes.

[Formula 69]

SCHEME 7: Preparation of Amino Acid Site

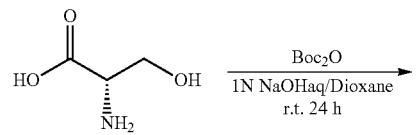

-continued

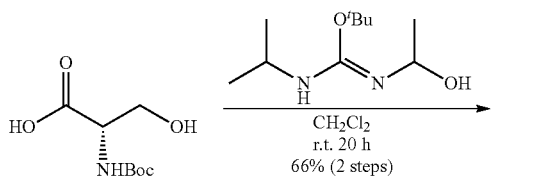

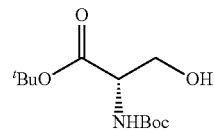

[Formula 70]

SCHEME 8: Preparation of Phosphoramidite 13

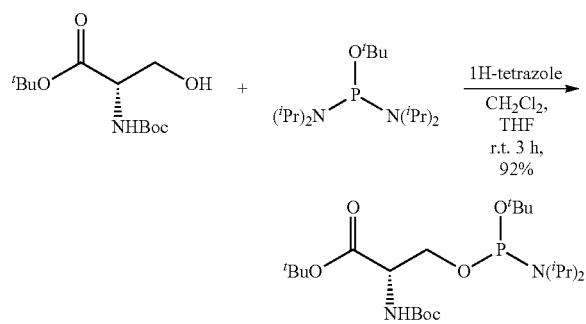

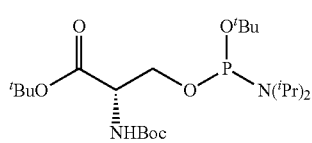

[Formula 71]

SCHEME 9: Preparation of Side Chain Sites Having Benzene Ring(s) (14, 15)

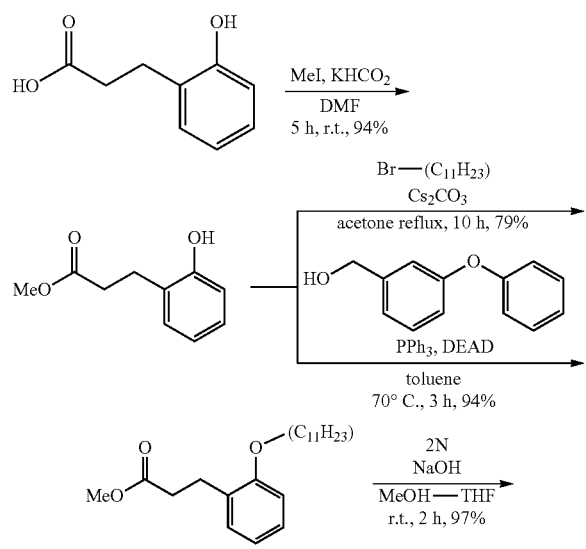

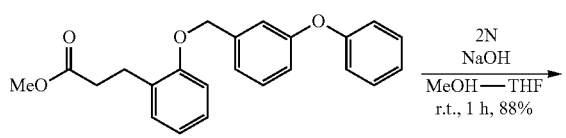

-continued

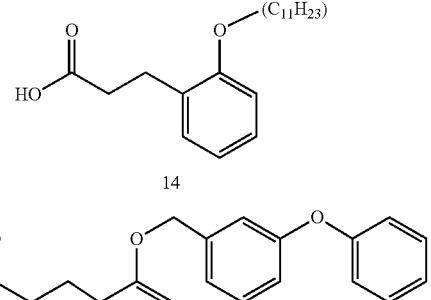

14

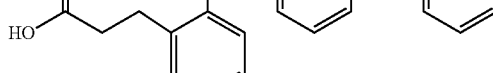

15

Synthesis methods for the side chain sites to be used in the present invention are described below. Such side chain sites can also be used independently as fatty acid surrogates.

Example 30

Synthesis of 3-(2-((3-phenoxybenzyl)oxy)phenyl)propanoic acid

[Formula 72]

Compound 30

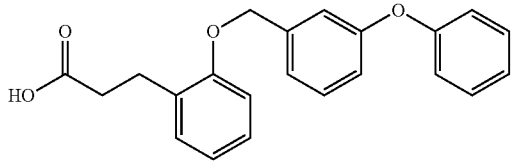 [SMILES: O=C(O)CCc1ccccc1OCc1cccc(Oc2ccccc2)c1]

Synthesis of Intermediate 30-1

[Formula 73]

Intermediate 30-1

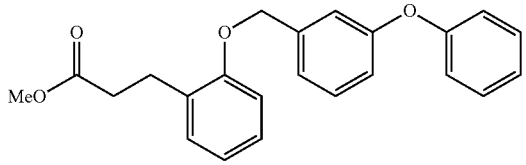

To a solution of methyl 3-(2-hydroxyphenyl)propionate (149.8 mg, 0.831 mmol), 3-phenoxybenzyl alcohol (118.2 mg, 0.590 mmol) and triphenylphosphine (198.1 mg, 0.755 mmol) in toluene (5 mL), DEAD (2 M toluene solution, 374.6 µL, 0.749 mmol) was added dropwise at room temperature, followed by stirring at 70° C. for 3 hours. The solvent in the liquid reaction mixture was distilled off and the residue was purified by column chromatography (hexane:ethyl acetate=15:1) to give the titled compound (200.2 mg, 0.552 mmol, 94%, yellow oil).
$^1$H NMR (CDCl$_3$): δ (ppm): δ=7.340 (3H, m), 7.158 (3H, m), 7.144 (1H, m), 7.075 (1H, m), 7.025 (2H, m), 6.893 (1H, m), 6.864 (1H, m), 5.064 (2H, s), 2.636 (3H, s), 2.972 (2H, t, J=7.74 Hz), 2.609 (2H, t, J=7.74 Hz).

Synthesis of Compound 30

[Formula 74]

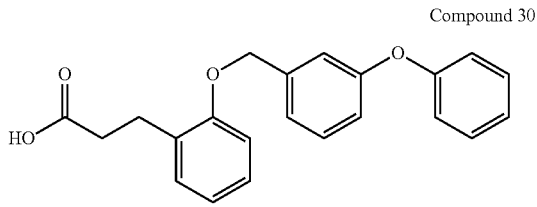

Compound 30

Intermediate 30-1 (176.0 mg, 0.486 mmol) was dissolved in methanol (2 mL) and THF (2 mL), followed by addition of sodium hydroxide (2 N aqueous solution, 2 mL) and stirring at room temperature for an hour. The liquid reaction mixture was rendered acidic by adding 2 N HCl until the pH of the aqueous layer became 2. The solution was subjected to three extractions with ethyl acetate (20 mL×3). The organic layers were combined, dried with sodium sulfate, and the solvent was distilled off. The residue was purified by column chromatography (hexane:ethyl acetate=1:1) to give the titled compound (149.6 mg, 0.429 mmol, 88%, colorless oil).

$^1$H NMR (CDCl$_3$): δ (ppm): δ=10.932 (1H, brs), 7.341 (3H, m), 7.713 (3H, m), 7.112 (1H, m), 7.067 (1H, m), 7.029 (2H, m), 6.966 (1H, m), 6.911 (1H, m), 6.882 (1H, m), 5.065 (2H, s), 2.975 (2H, t, J=7.68 Hz), 2.651 (2H, t, J=7.68 Hz).

$^{13}$C NMR (CDCl$_3$): δ (ppm): S=178.82, 157.70, 156.88, 156.37, 139.20, 130.14, 129.93, 129.78, 128.84, 127.68, 123.47, 121.54, 120.88, 119.19, 118.00, 117.04, 111.58, 69.34, 33.81, 25.86

HRMS (ESI, [M-H]$^-$: C$_{22}$H$_{19}$O$_4^-$ calc'd 347.1289; found 347.1318.

Example 31

Synthesis of 3-(2-((3-(o-tolyloxy)benzyl)oxy)phenyl)propanoic acid

[Formula 75]

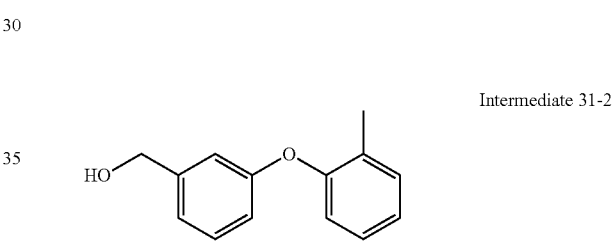

Compound 31

Synthesis of Intermediate 31-1

[Formula 76]

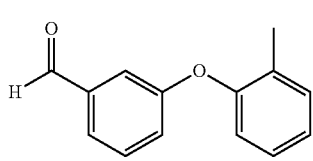

Intermediate 31-1

A 100 ml round-bottom flask containing a solution of copper acetate (452.6 mg, 2.492 mmol) in anhydrous dichloromethane (20 mL) was charged with anhydrous pyridine (0.200 mL, 2.483 mmol), a 4 A molecular sieve, o-cresol (289.1 mg, 2.673 mmol) and 3-formylphenylboronic acid (566.6 mg, 3.779 mmol) and the liquid reaction mixture was stirred at room temperature for 17.5 hours. The liquid mixture was filtered over Celite (registered trademark) and the solvent was distilled off to yield green solids. The residue was purified by column chromatography (n-hexane:diethyl ether=20:1) and dried overnight under vacuum to give the titled compound (298.7 mg, 1.407 mmol, 53%).

$^1$H NMR (400 MHz, CDCl$_3$): S=9.938 (1H, s), 7.548 (1H, dt, J=7.52 Hz, 1.14 Hz), 7.465 (1H, t, J=7.80 Hz), 7.335 (1H, dd, J=2.40 Hz, 0.72 Hz), 7.279 (1H, d, J=7.44 Hz), 7.226-7.183 (2H, m), 7.124 (1H, td, J=7.42 Hz, 1.16 Hz), 6.942 (1H, d, J=8.00 Hz), 2.214 (3H, s).

$^{13}$C NMR (100 MHz, CDCl$_3$): δ=191.71, 158.79, 153.45, 137.98, 131.72, 130.32, 130.21, 127.41, 124.86, 124.02, 123.11, 120.27, 116.46, 16.08.

HRMS (ESI-TOF, [M+Na]$^+$): C$_{14}$H$_{12}$NaO$_2^+$: calc'd 235.0730; found 235.0703.

Synthesis of Intermediate 31-2

[Formula 77]

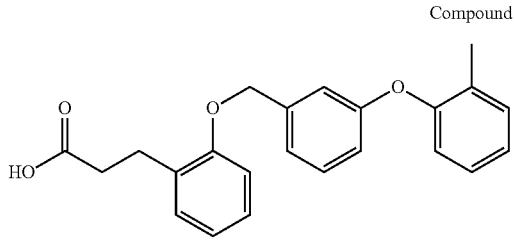

Intermediate 31-2

To a solution of intermediate 31-1 (294.8 mg, 1.389 mmol) in methanol (10 mL), sodium borohydride (111.6 mg, 1.389 mmol) was added in small amounts at 0° C., followed by stirring at 0° C. for 30 minutes. The liquid reaction mixture was diluted with dichloromethane (10 mL), a saturated aqueous sodium hydrogencarbonate solution (5 mL) and water (10 mL). The solution was subjected to three extractions with dichloromethane (20 mL×3); the organic layers were combined, dried with sodium sulfate, and the solvent was distilled off. The residue was purified by column chromatography (n-hexane: ethyl acetate=3:1) to give the titled compound (257.0 mg, 1.199 mmol, 88%, colorless oil).

$^1$H NMR (400 MHz, CDCl$_3$): δ=7.290-7.237 (2H, m), 7.183-7.139 (1H, m), 7.060 (1H, td, J=10.5 Hz, 1.24 Hz), 7.025 (1H, dd, J=7.56 Hz, 0.28 Hz), 6.915-6.893 (2H, m), 6.822-6.796 (1H, m), 4.628 (2H, s), 2.228 (3H, s), 1.780 (1H, s).

$^{13}$C NMR (100 MHz, CDCl$_3$): δ=158.21, 154.21, 142.82, 131.46, 130.05, 129.78, 127.15, 124.12, 120.67, 119.90, 116.30, 115.54, 64.98, 16.15.

HRMS (ESI-TOF, [M+Na]$^+$): C$_{14}$H$_{14}$NaO$_2^+$: calc'd 237.0886; found 237.0914.

Synthesis of Intermediate 31-3

[Formula 78]

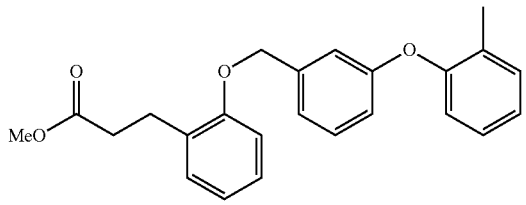

Intermediate 31-3

To a solution of methyl 3-(2-hydroxyphenyl)propionate (342.6 mg, 1.901 mmol), intermediate 31-2 (238.9 mg, 238.9 mmol) and triphenylphosphine (594.5 mg, 2.267 mmol) in toluene (15 mL), DEAD (2 M toluene solution, 1.0 mL) was added dropwise at room temperature and the liquid reaction mixture was stirred at 70° C. for 3.8 hours in an argon atmosphere. The solvent in the liquid reaction mixture was distilled off and the residue was purified by column chromatography (n-hexane:ethyl acetate=15:1) to give the titled compound (375.6 mg, 0.9977 mmol, 89%, pink oil).

$^1$H NMR (400 MHz, CDCl$_3$): δ=7.297 (1H, t, J=7.8 Hz), 7.252-7.237 (1H, m), 7.185-7.133 (3H, m), 7.102-7.052 (2H, m), 6.946-6.836 (5H, m), 5.033 (2H, s), 3.633 (3H, s), 2.952 (2H, t, J=7.6 Hz), 2.595 (2H, t, J=7.6 Hz), 2.215 (3H, s).

$^{13}$C NMR (100 MHz, CDCl$_3$): δ=173.69, 158.22, 156.34, 154.10, 139.15, 131.46, 130.11, 130.09, 129.79, 129.10, 127.53, 127.17, 124.21, 120.77, 120.67, 120.04, 116.39, 115.45, 111.50, 69.29, 51.43, 33.95, 26.13, 16.12.

HRMS (ESI-TOF, [M+Na]$^+$): C$_{24}$H$_{24}$NaO$_4^+$: calc'd 399.1567; found 399.1566.

Synthesis of Compound 31

[Formula 79]

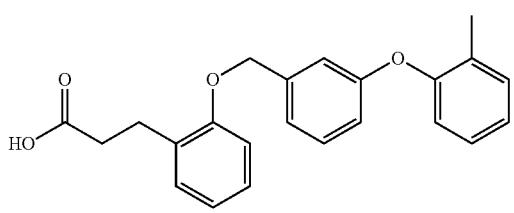

Compound 31

Intermediate 31-3 (360.9 mg, 0.9587 mmol) was dissolved in methanol (2 mL) and THF (2 mL) and sodium hydroxide (2 N aqueous solution, 2 mL) was added, followed by stirring at room temperature for 3.5 hours. The liquid reaction mixture was rendered acidic by adding 2 N HCl until the pH of the aqueous layer became 2. The solution was subjected to three extractions with ethyl acetate (20 mL×3). The organic layers were combined, dried with sodium sulfate, and the solvent was distilled off. The residue was purified by column chromatography (n-hexane:ethyl acetate=2:1) to give the titled compound (335.0 mg, 0.9243 mmol, 96%, colorless oil).

$^1$H NMR (400 MHz, CDCl$_3$): δ=7.298 (1H, t, J=7.90 Hz), 7.247-7.227 (1H, m), 7.180-7.140 (1H; m), 7.100-7.047 (2H, m), 6.936-6.837 (5H, m), 5.032 (2H, s), 2.943 (2H, t, J=7.66 Hz), 2.628 (2H, t, J=7.66 Hz), 2.208 (3H, s).

$^{13}$C NMR (100 MHz, CDCl$_3$): δ=179.31, 158.26, 156.33, 154.06, 139.07, 131.47, 130.16, 130.10, 129.83, 128.77, 127.64, 127.18, 124.24, 120.80, 120.65, 120.11, 116.46, 115.33, 111.51, 69.31, 33.82, 25.81, 16.12.

HRMS (ESI-TOF, [M-H]$^-$): C$_{23}$H$_{21}$O$_4^-$: calc'd 361.1445; found 361.1469.

Elemental analysis: C$_{23}$H$_{22}$O$_4$.0.1AcOEt: calc'd C, 75.71; H, 6.19; found: C, 75.42; H, 6.41.

Example 32

Synthesis of 3-(2-((3-(m-tolyloxy)benzyl)oxy)phenyl)propanoic acid

[Formula 80]

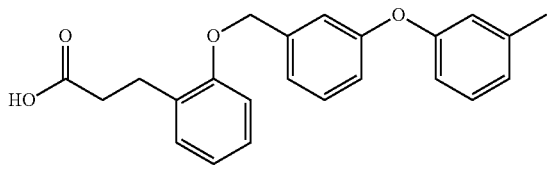

Compound 32

Synthesis was performed by the same method as in Example 31 except that o-cresol was replaced by m-cresol; in the final step, purification was conducted by column chromatography (n-hexane:ethyl acetate=1:1, dichloromethane:methanol=30:1) to give the titled compound (219.8 mg, 0.6065 mmol, 33%, colorless oil).

$^1$H NMR (400 MHz, CDCl$_3$): δ=7.326 (1H, t, J=8.0 Hz), 7.224-7.134 (4H, m), 7.042 (1H, s), 6.955-6.800 (6H, m), 5.055 (2H, s), 2.969 (2H, t, J=7.6 Hz), 2.642 (2H, t, J=7.6 Hz), 2.317 (3H, s).

$^{13}$C NMR (100 MHz, CDCl$_3$): δ=178.72, 157.79, 156.82, 156.37, 139.96, 139.15, 130.11, 129.87, 129.46, 128.84, 127.65, 124.28, 121.39, 120.85, 119.86, 117.92, 117.00, 116.18, 111.58, 69.35, 33.79, 25.84, 21.33.

HRMS (ESI-TOF, [M-H]$^-$): C$_{23}$H$_{27}$O$_4^-$: calc'd 361.1445; found 361.1447.

Example 33

Synthesis of 3-(2-((3-(p-tolyloxy)benzyl)oxy)phenyl)propanoic acid

[Formula 81]

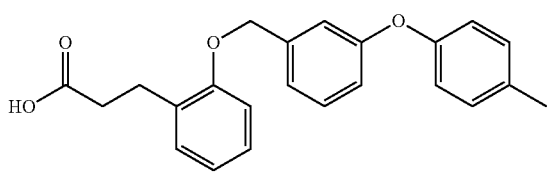

Compound 33

Synthesis was performed by the same method as in Example 31 except that o-cresol was replaced by p-cresol; in the final step, purification was conducted by column chromatography (n-hexane:ethyl acetate=2:1) and subsequent recrystallization with n-hexane and dichloromethane to give the titled compound (595.5 mg, 1.643 mmol, 73%, white powder).

$^1$H NMR (CDCl$_3$): δ=7.311 (1H, t, J=4.0 Hz), 7.186-7.108 (5H, m), 7.016 (1H, s), 6.935-6.846 (5H, m), 5.042 (2H, s), 2.962 (2H, t, J=3.8 Hz), 2.641 (2H, t, J=3.8 Hz), 2.328 (3H, s).
$^{13}$C NMR (CDCl$_3$): δ=179.06, 158.25, 156.36, 154.30, 139.07, 133.19, 130.28, 130.12, 129.83, 128.80, 127.66, 121.12, 120.82, 119.41, 117.45, 116.47, 111.53, 69.33, 33.82, 25.85, 20.69.
HRMS (ESI-TOF, [M-H]$^-$): C$_{23}$H$_{21}$O$_4^-$: calc'd 361.1445; found 361.1433.
Elemental analysis: C$_{23}$H$_{22}$O$_4$: calc'd C, 76.22; H, 6.12; found C, 76.00; H, 6.29.
Mp: 104.5-106.0° C. (recrystallized from n-hexane/CH$_2$Cl$_2$, colorless powder).

Example 34

Synthesis of 3-(2-((3-(3-chlorophenoxy)benzyl)oxy)phenyl)propanoic acid

[Formula 82]

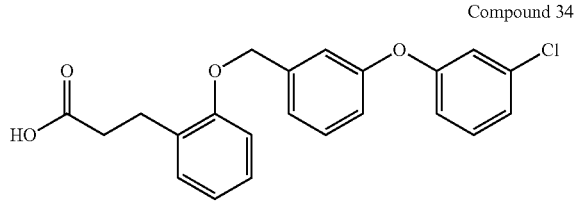

Compound 34

Synthesis was performed by the same method as in Example 31 except that o-cresol was replaced by m-chlorophenol; in the final step, purification was conducted by column chromatography (n-hexane:ethyl acetate=2:1) to give the titled compound (466.4 mg, 1.218 mmol, 99%, white powder).
$^1$H NMR (400 MHz, CDCl$_3$): δ=7.357 (1H, t, J=7.86 Hz), 7.245-7.152 (4H, m), 7.081-7.046 (2H, m), 6.999 (1H, t, J=2.12 Hz), 6.969 (1H, dd, J=2.42 Hz, 0.40 Hz), 6.915-6.848 (3H, m), 5.065 (2H, s), 2.977 (2H, t, J=7.66 Hz), 2.657 (2H, t, J=7.68 Hz).
$^{13}$C NMR (100 MHz, CDCl$_3$): δ=179.49, 157.96, 156.73, 156.28, 139.46, 135.03, 130.50, 130.13, 130.12, 128.78, 127.69, 123.41, 122.29, 120.93, 119.09, 118.47, 117.59, 116.92, 111.53, 69.19, 33.91, 25.83.
HRMS (ESI-TOF, [M-H]$^-$): C$_{22}$H$_{18}$ClO$_4^-$: calc'd 381.0899; found 381.0913.
Elemental analysis: C$_{22}$H$_{19}$ClO$_4$: calc'd C, 69.02; H, 5.00; found C, 68.72; H, 5.14.

Example 35

Synthesis of 3-(2-((3-(4-chlorophenoxy)benzynoxy)phenyl)propanoic acid

[Formula 83]

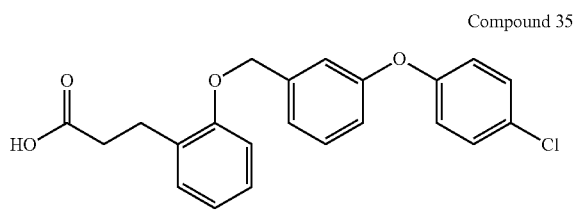

Compound 35

Synthesis was performed by the same method as in Example 31 except that o-cresol was replaced by p-chlorophenol; in the final step, purification was conducted by column chromatography (n-hexane:ethyl acetate=1:1) to give the titled compound (349.5 mg, 0.9129 mmol, 94%, white powder).
$^1$H NMR (400 MHz, CDCl$_3$): δ=7.356 (1H, t, J=7.8 Hz), 7.289 (2H, dt, J=8.8 Hz, 2.8 Hz), 7.205-7.165 (3H, m), 7.060 (1H, s), 6.974-6.862 (5H, m), 5.071 (2H, s), 2.984 (2H, t, J=7.6 Hz), 2.662 (2H, t, J=7.6 Hz).
$^{13}$C NMR (100 MHz, CDCl$_3$): δ=179.22, 157.29, 156.28, 155.58, 139.37, 130.12, 130.04, 129.74, 128.80, 128.44, 127.67, 121.94, 120.92, 120.31, 118.01, 117.12, 111.55, 69.22, 33.87, 25.83.
HRMS (ESI-TOF, [M-H]$^-$): C$_{22}$H$_{18}$ClO$_4^-$: calc'd 381.0899; found 381.0892.
Elemental analysis: C$_{22}$H$_{19}$ClO$_4$: calc'd C, 69.02; H, 5.00; found C, 68.79; H, 5.13.

Example 36

Synthesis of 3-(2-((2',6'-dimethyl[1,1'-biphenyl]-3-yl)methoxy)phenyl)propanoic acid

[Formula 84]

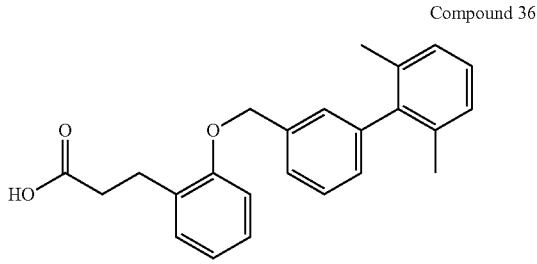

Compound 36

Synthesis of Intermediate 36-1

[Formula 85]

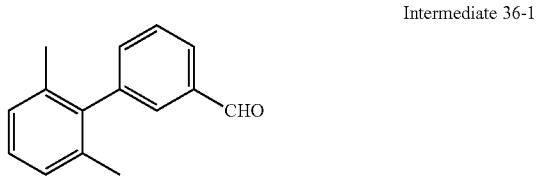

Intermediate 36-1

To a solution of 3-bromobenzaldehyde (370.4 mg, 2.002 mmol), 2,6-dimethylphenylboronic acid (420.5 mg, 2.804 mmol) and a saturated aqueous sodium hydrogencarbonate solution (1 M solution, 4 mL, 4.001 mmol) in a mixture of ethanol (2.2 mL) and toluene (4 mL), tetrakis(triphenylphosphine)palladium(0) (114.9 mg, 0.099 mmol) was added, followed by stirring at 80° C. for 22 hours in an argon atmosphere. After cooling the liquid reaction mixture, water (5 mL) and ethyl acetate (10 mL) were added, followed by filtering over Celite (registered trademark). After separation into the aqueous and organic layers, the aqueous layer was subjected to two extractions with ethyl acetate (20 mL); the organic layers were combined and subjected to extraction with saline (30 mL) whereas all aqueous layers were subjected to extraction with ethyl acetate (20 mL). The organic layers were combined, dried with sodium sulfate, the solvent was distilled off, and the residue was purified by column chromatography (hexane:diethyl ether=60:1-50:1) to give the titled compound (347.8 mg, 1.655 mmol, 83%, colorless oil).

¹H-NMR (CDCl₃): δ=10.067 (1H, s), 7.889 (1H, dt, J=1.4, 7.7 Hz), 7.698 (1H, dt, J=0.4, 1.8 Hz), 7.618 (1H, t, J=7.6 Hz), 7.450 (1H, dt, J=1.6, 7.6 Hz), 7.209 (1H, m), 7.136 (2H, m), 2.029 (6H, s). ¹³C-NMR (CDCl₃): δ=192.31, 142.11, 140.22, 136.73, 135.80, 135.30, 130.50, 129.23, 128.01, 127.51, 127.48, 20.79.

Synthesis of Intermediate 36-2

[Formula 86]

Intermediate 36-2

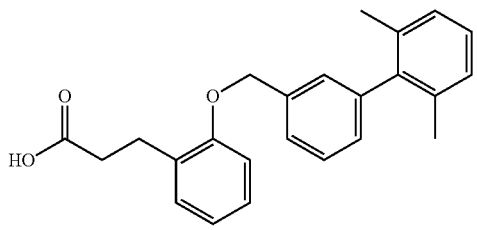

Synthesis was performed by the same method as in Example 31 except that intermediate 31-1 was replaced by intermediate 36-1; in the final step, purification was conducted by column chromatography (n-hexane:ethyl acetate=1:0-4:1-2:1) to give the titled compound (229.1 mg, 0.636 mmol, 83%, white solids).

¹H-NMR (CDCl₃): δ=7.431 (2H, m), 7.210-7.097 (7H, m), 6.908 (2H, m), 5.148 (2H, s), 3.008 (2H, t, J=7.8 Hz), 2.695 (2H, m), 2.025 (6H, s).

¹³C-NMR (CDCl₃): δ=178.93, 156.52, 141.47, 141.34, 137.34, 136.00, 130.08, 128.85, 128.72, 128.57, 127.85, 127.64, 127.29, 127.08, 125.42, 120.79, 111.73, 69.89, 33.82, 25.97, 20.80.

HRMS (ESI-TOF, [M-H]⁻): C₂₄H₂₃O₃⁻: calc'd 359.1653; found 359.1673.

Elemental analysis: C₁₇H₂₆O₃: calc'd C, 79.97; H, 6.71; N, 0.00; found C, 79.59; H, 6.84; N, 0.00. Mp: 117.5-120.0° C., colorless solids.

Example 37

Synthesis of 3-(3-((2',6'-dimethyl[1,1'-biphenyl]-3-yl)methoxy)phenyl)propanoic acid

[Formula 87]

Compound 37

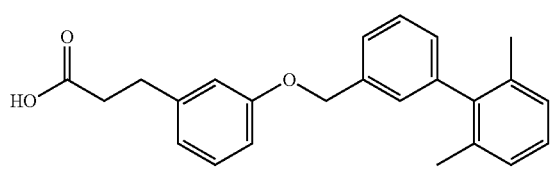

Synthesis was performed by the same method as in Example 36 except that methyl 3-(2-hydroxyphenyl)propionate was replaced by methyl 3-(3-hydroxyphenyl)propionate; in the final step, purification was conducted by column chromatography (hexane: ethyl acetate=1:0-4:1-2:1) to give the titled compound (366.2 mg, 1.016 mmol, 98%, colorless oil).

¹H-NMR (CDCl₃): δ=7.423 (2H, m), 7.228-7.099 (6H, m), 6.825 (3H, m), 5.109 (2H, s), 2.928 (1H, t, J=7.8 Hz), 2.670 (1H, m), 2.022 (6H, s).

¹³C-NMR (CDCl₃): δ=178.33, 158.89, 141.73, 141.49, 141.31, 137.25, 136.00, 129.53, 128.67, 128.56, 127.98, 127.28, 127.07, 125.57, 120.85, 115.15, 112.74, 69.90, 35.31, 30.57, 20.82.

HRMS (ESI-TOF, [M-H]⁻): C₂₄H₂₃O₃: calc'd 359.1653; found 359.1685.

Elemental analysis: C₂₄H₂₄O₃.0.1H₂O: calc'd C, 79.57; H, 6.73; N, 0.00; found C, 79.49; H, 6.81; N, 0.00.

Example 38

Synthesis of 3-(2-((3-(3,4-dichlorophenoxy)benzyl)oxy)phenyl)propanoic acid

[Formula 88]

Compound 38

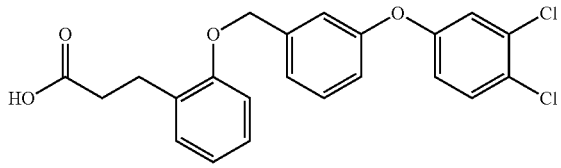 [SMILES: O=C(O)CCc1ccccc1OCc1cccc(Oc2ccc(Cl)cc2)c1]

Synthesis was performed by the same method as in Example 31 except that o-cresol was replaced by 3,4-dichlorophenol; in the final step, purification was conducted by column chromatography (n-hexane:ethyl acetate=1:1) to give the titled compound (486.3 mg, 1.165 mmol, 92%, white solids).

¹H NMR (400 MHz, CDCl₃): δ=7.369 (1H, t, J=8.0 Hz), 7.356 (1H, d, J=8.8 Hz), 7.244-7.156 (3H, m), 7.095 (1H, d, J=2.4 Hz), 7.076 (1H, s), 6.950 (1H, dd, J=2.7 Hz, 0.8 Hz), 6.903 (1H, td, J=7.2 Hz, 0.8 Hz), 6.862 (1H, d, J=8.4 Hz), 6.848 (1H, dd, J=2.9 Hz, 1.4 Hz), 5.073 (2H, s), 2.980 (2H, t, J=7.6 Hz), 2.658 (2H, t, J=7.6 Hz).

¹³C NMR (100 MHz, CDCl₃): δ=179.33, 156.48, 156.32, 156.24, 139.63, 133.20, 131.02, 130.23, 130.15, 128.78, 127.71, 126.64, 122.61, 120.99, 120.55, 118.46, 118.15, 117.65, 111.54, 69.15, 33.90, 25.85.

HRMS (ESI-TOF, [M-H]⁻): C₂₂H₁₇Cl₂O₄⁻: calc'd 415.0509; found 415.0525.

Elemental analysis: C₂₂H₁₈Cl₂O₄: calc'd C, 63.32; H, 4.35; found C, 63.05; H, 4.57.

Example 39

Synthesis of 3-(2-((3-(2-fluorophenoxy)benzyl)oxy)phenyl)propanoic acid

[Formula 89]

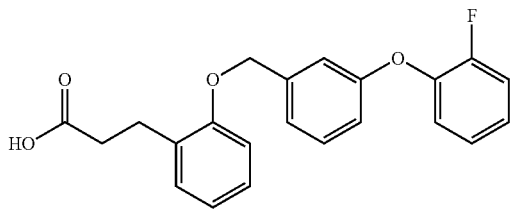 [SMILES: O=C(O)CCc1ccccc1OCc1cccc(Oc2ccccc2F)c1]

Compound 39

Synthesis was performed by the same method as in Example 31 except that o-cresol was replaced by 2-fluorophenol; in the final step, purification was conducted by column chromatography (hexane:ethyl acetate=2:1-1:2) to give the titled compound (278.2 mg, 0.7602 mmol, 93.55%, colorless oil).

$^1$H NMR (CDCl$_3$): δ (ppm): δ=10.718 (brs, 1H), 7.431-7.392 (m, 1H), 7.283-7.132 (m, 8H), 7.043-6.936 (m, 3H), 5.126 (s, 2H), 3.064 (t, 2H, J=7.6 Hz), 2.741 (t, 2H, J=7.6 Hz).

$^{13}$C NMR (CDCl$_3$): δ (ppm): δ=179.87, 157.89, 156.44, 155.80, 153.32, 143.55, 143.43, 139.34, 130.22, 120.02, 128.90, 127.80, 125.22, 125.15, 124.88, 124.84, 122.34, 122.33, 121.57, 121.00, 117.31, 117.13, 116.59, 115.52, 111.68, 69.34, 34.05, 25.91.

HRMS (ESI-TOF [M-H]$^-$): C$_{22}$H$_{18}$FNaO$_4^-$ calc'd 365.1195; found 365.1223.

Elemental analysis: calc'd C, 71.72%; H, 5.28%; N, 0.00% (C$_{22}$H$_{19}$FNaO$_4$+ethyl acetate×0.1); found C, 71.42%; H, 5.27%; N, 0.00%.

Example 40

Synthesis of 3-(2-((3-(4-bromorophenoxy)benzyl)oxy)phenyl)propanoic acid

[Formula 90]

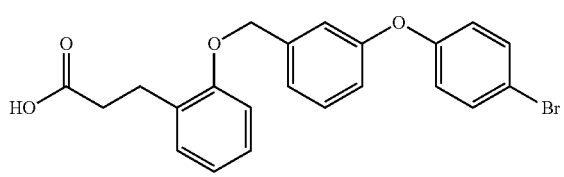 [SMILES: O=C(O)CCc1ccccc1OCc1cccc(Oc2ccc(Br)cc2)c1]

Compound 40

Synthesis was performed by the same method as in Example 31 except that o-cresol was replaced by 4-bromophenol; in the final step, purification was conducted by column chromatography (n-hexane:ethyl acetate=6:1-2:1) to give the titled compound (130.0 mg, 0.3042 mmol, 92%, white powder).

$^1$H NMR (400 MHz, CDCl$_3$): δ=7.420 (2H, dt, J=8.88 Hz, 2.70 Hz), 7.346 (1H, t, J=7.88 Hz), 7.193-7.153 (3H, m), 7.047 (1H, s), 6.952-6.848 (5H, m), 5.060 (2H, s), 2.970 (2H, t, J=7.70 Hz), 2.649 (2H, t, J=7.72 Hz).

$^{13}$C NMR (100 MHz, CDCl$_3$): δ=178.98, 157.15, 156.28, 156.19, 139.39, 132.72, 130.14, 130.07, 128.80, 127.69, 122.03, 120.93, 120.72, 118.11, 117.22, 115.89, 111.54, 69.21, 33.83, 25.85.

HRMS (ESI-TOF, [M-H]$^-$): C$_{22}$H$_{18}$BrO$_4^-$: calc'd 425.0394, 427.0373; found 425.0420, 427.0401.

Elemental analysis: C$_{22}$H$_{19}$BrO$_4$: calc'd C, 61.84; H, 4.48; found C, 61.54; H, 4.59.

Example 41

Synthesis of 3-(2-((3-(4-iodophenoxy)benzyl)oxy)phenyl)propanoic acid

[Formula 91]

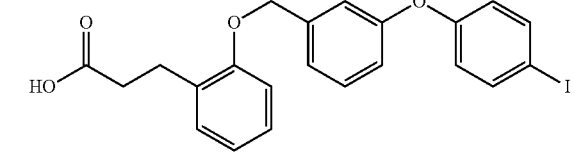

Compound 41

Synthesis was performed by the same method as in Example 31 except that o-cresol was replaced by 4-iodophenol; in the final step, purification was conducted by column chromatography (n-hexane:ethyl acetate=6:1-4:1-2:1) to give the titled compound (216.7 mg, 0.4569 mmol, 90%, pale greenish white powder).

HRMS (ESI-TOF, [M-H]$^-$): C$_{22}$H$_{18}$IO$_4^-$: calc'd 473.0255; found 473.0283.

Example 42

Synthesis of 3-(2-((3-(4-(tert-butyl)phenoxy)benzyl)oxy)phenyl)propanoic acid

[Formula 92]

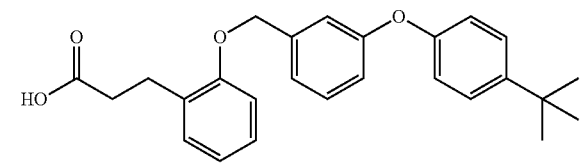 [SMILES: CC(C)(C)c1ccc(Oc2cccc(COc3ccccc3CCC(=O)O)c2)cc1]

Compound 42

Synthesis was performed by the same method as in Example 31 except that intermediate 31-1 was replaced by 3-(4-tert-butylphenoxy)benzaldehyde; in the final step, purification was conducted by column chromatography (n-hexane:ethyl acetate=2:1) to give the titled compound (632.9 mg, 1.565 mmol, 85%, white powder).

$^1$H NMR (400 MHz, CDCl$_3$): δ=7.341 (2H, dt, J=8.8 Hz, 2.6 Hz), 7.320 (1H, t, J=7.8 Hz), 7.186-7.119 (3H, m), 7.041 (1H, s), 6.965-6.850 (5H, m), 5.052 (2H, s), 2.963 (2H, t, J=7.6 Hz), 2.643 (2H, t, J=7.6 Hz), 1.317 (9H, s).

$^{13}$C NMR (100 MHz, CDCl$_3$): δ=178.12, 158.02, 156.38, 154.31, 146.39, 139.09, 130.15, 129.85, 128.82, 127.68, 126.58, 121.24, 120.83, 118.75, 117.72, 116.76, 111.57, 69.37, 34.31, 33.68, 31.47, 25.90.

HRMS (ESI-TOF, [M-H]$^-$): $C_{26}H_{27}O_4^-$: calc'd 403.1915; found 403.1900.

Elemental analysis: $C_{26}H_{28}O_4$: calc'd C, 77.20; H, 6.98; found C, 77.05; H, 7.01.

Mp: 111.1-112.5° C. (colorless solid cube, recrystallized from n-hexane/$CH_2Cl_2$).

Example 43

Synthesis of 3-(2-((3-[1,1'-biphenyl]-4-yloxy)benzyl)oxy)phenyl)propanoic acid

[Formula 93]

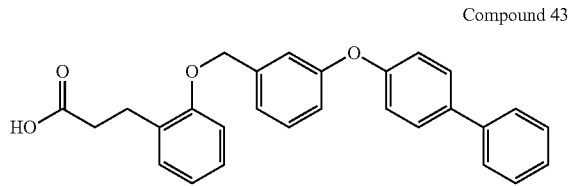

Compound 43

Synthesis was performed by the same method as in Example 31 except that o-cresol was replaced by 4-phenylphenol; in the final step, purification was conducted by column chromatography (n-hexane:ethyl acetate=6:1-2:1) to give the titled compound (189.5 mg, 0.4464 mmol, 84%, white solids).

$^1$H NMR (400 MHz, $CDCl_3$): δ=7.429-7.391 (2H, m), 7.365-7.287 (2H, m), 7.186-7.147 (3H, m), 7.104-7.057 (3H, m), 6.994 (1H, dd, J=8.08 Hz, 0.92 Hz), 6.903-6.849 (2H, m), 5.056 (2H, s), 2.965 (2H, t, J=7.68 Hz), 2.638 (2H, t, J=7.68 Hz).

$^{13}$C NMR (100 MHz, $CDCl_3$): δ=179.28, 157.56, 156.44, 156.33, 140.46, 139.25, 136.49, 130.12, 129.98, 128.80, 128.74, 128.44, 127.66, 127.02, 126.87, 121.69, 120.86, 119.32, 118.07, 117.19, 111.55, 69.29, 33.86, 25.84.

HRMS (ESI-TOF, [M-H]$^-$): $C_{28}H_{23}O_4^-$: calc'd 423.1602; found 423.1631.

Example 44

Synthesis of 3-(2-((3-(4-methoxyphenoxy)benzyl)oxy)phenyl)propanoic acid

[Formula 94]

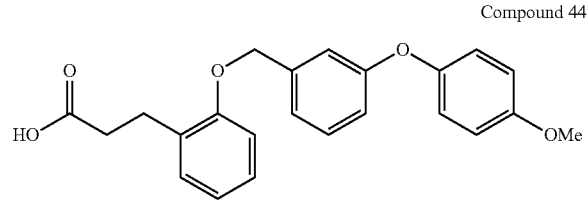

Compound 44

Synthesis was performed by the same method as in Example 31 except that o-cresol was replaced by 4-methoxyphenol; in the final step, purification was conducted by recrystallization using n-hexane and dichloromethane to give the titled compound (217.5 mg, 0.5748 mmol, 56%, pale pink solids).

$^1$H NMR (400 MHz, $CDCl_3$): δ=7.294 (1H, t, J=7.88 Hz), 7.181-7.146 (2H, m), 7.086 (1H, d, J=7.48 Hz), 6.993-6.971 (3H, m), 6.903-6.842 (5H, m), 5.032 (2H, s), 3.788 (3H, s), 2.955 (2H, t, J=7.64 Hz), 2.635 (2H, t, J=7.66 Hz).

$^{13}$C NMR (100 MHz, $CDCl_3$): δ=178.95, 158.93, 156.37, 156.04, 149.77, 139.04, 130.11, 129.80, 128.81, 127.66, 121.06, 120.83, 120.79, 116.80, 115.76, 114.91, 111.55, 69.37, 55.61, 33.80, 25.84.

HRMS (ESI-TOF, [M-H]$^-$): $C_{23}H_{21}O_5^-$: calc'd 377.1394; found 377.1400.

Example 45

Synthesis of 3-(2-((3-benzylbenzyl)oxy)phenyl)propanoic acid

[Formula 95]

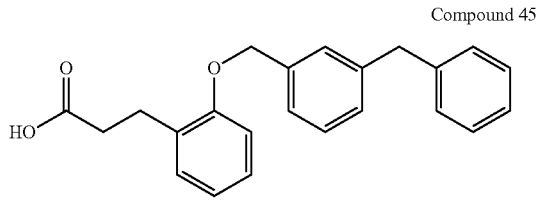

Compound 45

Synthesis was performed by basically the same method as in Example 31 except that intermediate 31-2 was replaced by m-benzylbenzyl alcohol; in the final step, purification was conducted by column chromatography (n-hexane:ethyl acetate=2:1, n-hexane: ethyl acetate=3:1-2:1) and subsequent recrystallization using n-hexane/dichloromethane to give the titled compound (413.6 mg, 1.194 mmol, 55%, white solids).

$^1$H NMR (400 MHz, $CDCl_3$): δ=7.309-7.127 (11H, m), 6.896-6.857 (2H, m), 5.031 (2H, s), 3.987 (2H, s), 2.967 (2H, t, J=7.70 Hz), 2.653 (2H, t, J=7.70 Hz).

$^{13}$C NMR (100 MHz, $CDCl_3$): δ=179.45, 156.51, 141.49, 140.84, 137.34, 130.08, 128.93, 128.79, 128.67, 128.47, 128.38, 127.65, 127.55, 126.10, 124.78, 120.72, 69.70, 41.83, 33.89, 25.91.

HRMS (ESI-TOF, [M-H]$^-$): $C_{23}H_{21}O_3^-$: calc'd 345.1496; found 345.1504.

Example 46

Synthesis of 3-(2-((3-(benzyloxy)benzyl)oxy)phenyl)propanoic acid

[Formula 96]

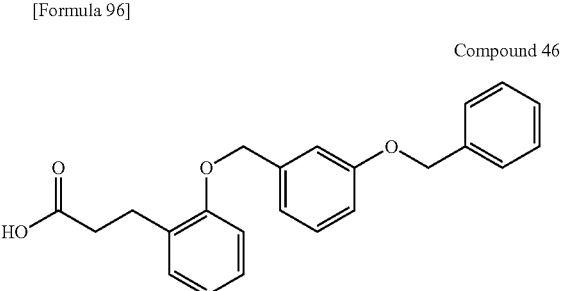

Compound 46

Synthesis was performed by basically the same method as in Example 31 except that o-cresol was replaced by benzyl bromide, and 3-formylphenylboronic acid by m-hydroxybenzaldehyde; in the final step, purification was conducted by column chromatography (n-hexane:ethyl acetate=2:1-0:1) to give the titled compound (701.3 mg, 1.935 mmol, 87%, white solids).

$^1$H NMR (400 MHz, CDCl$_3$): δ=7.435-7.232 (6H, m), 7.184-7.144 (2H, m), 7.058 (1H, s), 7.006 (1H, d, J=7.56 Hz), 6.934-6.861 (3H, m), 5.062 (2H, s), 5.058 (2H, s), 2.993 (2H, t, J=7.72 Hz), 2.681 (2H, t, J=7.74 Hz).

$^{13}$C NMR (100 MHz, CDCl$_3$): δ=179.31, 159.02, 156.46, 138.83, 136.89, 130.07, 129.63, 128.76, 128.54, 127.91, 127.67, 127.46, 120.78, 119.42, 114.37, 113.20, 119.59, 69.93, 69.60, 33.91, 25.91.

HRMS (ESI-TOF, [M-H]$^-$): C$_{23}$H$_{21}$O$_4^-$: calc'd 361.1445; found 361.1445.

Example 47

Synthesis of 3-(2-([1,1'-biphenyl]-3-ylmethoxy)phenyl)propanoic acid

[Formula 97]

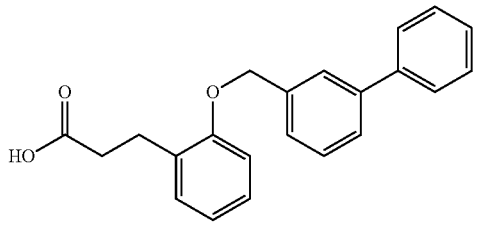 [SMILES: O=C(O)CCc1ccccc1OCc1cccc(-c2ccccc2)c1]

Compound 47

Synthesis was performed by the same method as in Example 31 except that intermediate 31-2 was replaced by 3-hydroxymethylbiphenyl; in the final step, purification was conducted by column chromatography (n-hexane:ethyl acetate=3:1) to give the titled compound (211.7 mg, 0.637 mmol, 95%, white solids).

$^1$H-NMR (CDCl$_3$): δ=11.572 (1H, brs), 7.686 (1H, m), 7.636 (1H, t, J=1.6 Hz), 7.617 (1H, m), 7.574 (1H, dt, 1.6, 7.6 Hz), 7.453 (4H, m), 7.362 (1H, m), 7.221 (2H, m), 6.944 (2H, m), 5.180 (2H, s), 3.064 (2H, m), 2.748 (2H, m).

$^{13}$C-NMR (CDCl$_3$): δ=179.45, 156.54, 141.56, 140.87, 137.73, 130.12, 129.03, 128.84, 128.78, 127.73, 127.40, 127.16, 126.64, 125.88, 125.77, 120.86, 111.64, 69.79, 33.99, 25.95.

HRMS (ESI-TOF, [M-H]$^-$): C$_{22}$H$_{19}$O$_3^-$: calc'd 331.1340; found 331.1389.

Elemental analysis: C$_{22}$H$_{20}$O$_3$: calc'd C, 79.50; H, 6.06; N, 0.00; found C, 79.26; H, 6.23; N, 0.00. Mp: 87.8° C.-88.8° C., colorless solid plate, (recrystallized from hexane-CH$_2$Cl$_2$).

Example 48

Synthesis of 3-(3-([1,1'-biphenyl]-3-ylmethoxy)phenyl)propanoic acid

[Formula 98]

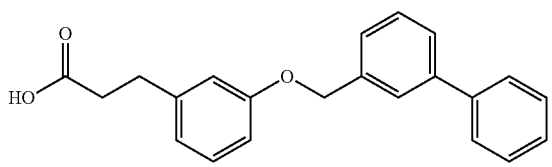 [SMILES: O=C(O)CCc1cccc(OCc2cccc(-c3ccccc3)c2)c1]

Compound 48

Synthesis was performed by the same method as in Example 47 except that methyl 3-(2-hydroxyphenyl)propionate was replaced by methyl 3-(3-hydroxyphenyl)propionate; in the final step, purification was conducted by column chromatography (n-hexane: ethyl acetate=3:1) to give the titled compound (185.0 mg, 0.557 mmol, 91%, white solids).

$^1$H-NMR (CDCl$_3$): δ=11.302 (1H, brs), 7.677 (1H, m), 7.614 (2H, m), 7.569 (1H, dt, J=1.6, 7.6 Hz), 7.451 (4H, m), 7.365 (1H, m), 7.231 (1H, m), 6.855 (3H, m), 5.120 (2H, s), 2.952 (2H, m), 2.694 (2H, m).

$^{13}$C-NMR (CDCl$_3$): δ=178.74, 158.97, 141.81, 141.60, 140.91, 137.51, 129.60, 129.02, 128.76, 127.40, 127.20, 126.80, 126.40, 126.33, 120.93, 115.07, 112.59, 69.97, 35.39, 30.58.

HRMS (ESI-TOF, [M-H]$^-$): C$_{22}$H$_{19}$O$_3^-$; calc'd 331.1340; found 331.1369.

Elemental analysis: C$_{22}$H$_{20}$O$_3$: calc'd C, 79.50; H, 6.06; N, 0.00; found C, 79.44; H, 6.10; N, 0.00. Mp: 90.0° C.-91.0° C., colorless solid plate, (recrystallized from hexane-CH$_2$Cl$_2$).

Example 49

Synthesis of 3-(2-((3-(phenylamino)benzyl)oxy)phenyl)propanoic acid

[Formula 99]

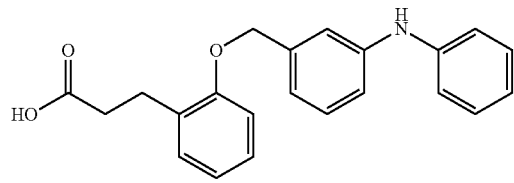

Compound 49

Synthesis was performed by the same method as in Example 31 except that the combination of o-cresol and 3-formylphenylboronic acid was replaced by the combination of ethyl 3-aminobenzoate and phenylboronic acid; in the final step, purification was conducted by column chromatography (n-hexane:ethyl acetate=2:1-0:1) to give the titled compound (227.0 mg, 0.653 mmol, 75% (2 steps), colorless oil).

¹H-NMR (CDCl₃): δ=7.298 (3H, m), 7.231 (2H, m), 7.182 (1H, t, J=1.8 Hz), 7.111 (2H, m), 7.056 (1H, ddd, J=8.0 Hz, 2.4 Hz, 0.8 Hz), 7.002-6.920 (4H, m), 5.085 (2H, s), 3.061 (2H, t, J=7.8z), 2.736 (2H, m).

¹³C-NMR (CDCl₃): δ=179.67, 156.41, 143.55, 142.70, 138.50, 130.06, 129.46, 129.29, 128.73, 127.67, 121.20, 120.73, 119.09, 118.15, 116.52, 115.74, 111.61, 69.50, 34.02, 25.95, 20.99.

HRMS (ESI-TOF, [M-H]⁻): $C_{22}H_{20}NO_3^-$: calc'd 346.1449; found 346.1458.

Elemental analysis: $C_{22}H_{21}NO_3$: found C, 76.23 H, 6.21; N, 4.09; calc'd C, 76.06; H, 6.09; N, 4.03.

Example 50

Synthesis of 3-(3-((3-phenoxyphenoxy)methyl)phenyl)propanoic acid

[Formula 100]

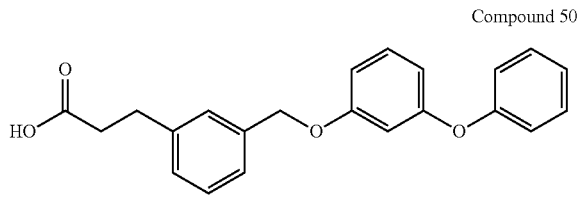

Compound 50

Synthesis of Intermediate 50-1

[Formula 101]

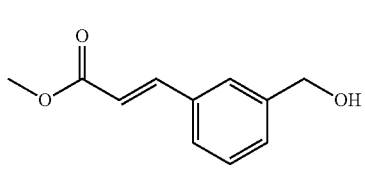

Intermediate 50-1

A solution of lithium chloride (1.1906 g, 1.56 eq.) in acetonitrile (20 mL), a solution of 3-hydroxymethylbenzaldehyde (2.4528 g) in acetonitrile (10 mL) and a solution of trimethyl phosphonoacetate (5.1150 g, 1.56 eq.) in acetonitrile (10 mL) were mixed at room temperature; to the resulting mixed solution, a solution of DBU (1,8-diazabicyclo[5.4.0]-7-undecene) (4.2682 g, 1.56 eq.) in acetonitrile (10 mL) was added over 2 minutes at 0° C., followed by stirring at 0° C. for 20 minutes, then at room temperature for 17 hours. After addition of water (50 mL), extraction with ethyl acetate (250 mL) followed; the organic layer was washed with saline (100 mL) and then dried over magnesium sulfate. The residue obtained by distilling off the solvent was purified by column chromatography (ethyl acetate:n-hexane=1:2) to give the titled compound (2.5720 g, 74%, colorless oil).

¹H-NMR (400 MHz, CDCl₃): 7.679 (1H, d, J=16.0 Hz), 7.523 (1H, s), 7.449-7.426 (1H, m), 7.383-7.370 (2H, d-like m), 6.444 (1H, d, J=16.0 Hz), 4.713 (2H, s), 3.800 (3H, s).

¹³C-NMR (100 MHz, CDCl₃): 167.42, 144.65, 141.62, 134.60, 129.06, 128.75, 127.30, 126.35, 118.00, 64.79, 51.71.

Elemental analysis: $C_{11}H_{12}O_3$: calc'd C, 68.74; H, 6.29; N, 0.00; found C, 68.52; H, 6.30; N, 0.00.

Synthesis of Intermediate 50-2

[Formula 102]

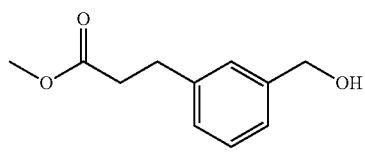

Intermediate 50-2

To a solution of intermediate 50-1 (2.2627 g) in methanol (100 mL), shavings of magnesium (magnesium turning) (2.8676 g, 10 eq. to intermediate 50-1) was added at 8° C., followed by stirring at 12° C. for 3.5 hours. After cooling to 0° C., a 10% HCl aqueous solution was added and extraction with ethyl acetate (600 mL) followed; the organic layer was washed with saline (250 mL) and then dried over magnesium sulfate. The residue obtained by distilling off the solvent was purified by column chromatography (ethyl acetate:n-hexane=3:4) to give the titled compound (2.3038 g, 80%, colorless oil).

¹H-NMR (400 MHz, CDCl₃): 7.291 (1H, t, J=8.0 Hz), 7.219-7.202 (2H, brd m), 7.137 (1H, d, J=7.6 Hz), 4.678 (2H, s), 3.674 (1H, s), 2.963 (2H, t, J=8.0 Hz), 2.641 (2H, t, J=7.6 Hz), 1.619 (1H, OH).

¹³C-NMR (100 MHz, CDCl₃): 173.32, 141.14, 140.78, 128.67, 127.48, 126.86, 124.89, 65.16, 51.60, 35.57, 30.79.

Elemental analysis: $C_{11}H_{14}O_3+0.2H_2O$: calc'd C, 66.78; H, 7.34; N, 0.00; found C, 66.95; H, 7.16; N, 0.00.

HRMS (ESI-TOF, [M+Na]⁺): $C_{11}H_{14}NaO_3^+$: calc'd 217.08352; found 217.08637.

Synthesis of Intermediate 50-3

[Formula 103]

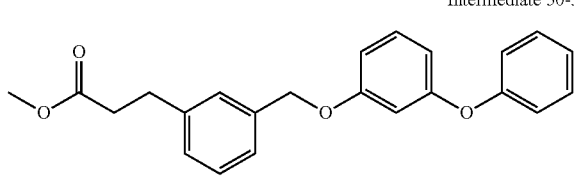

Intermediate 50-3

To a solution of intermediate 50-2 (189.3 mg), 3-phenoxyphenol (202.9 mg, 1.2 eq.) and triphenylphosphine (303.4 mg, 1.3 eq.) in toluene (5 mL), DEAD (40% (w/w) in toluene, 0.7 mL, 1.3 eq.) was added at room temperature over 5 minutes. The liquid reaction mixture, after being stirred at 69-75° C. for 21 hours, was purified by column chromatography (ethyl acetate:n-hexane=1:4, ethyl acetate: n-hexane=3:80) to give the titled compound (286.2 mg, 81%, colorless sticky oil).

¹H-NMR (400 MHz, CDCl₃): 7.325 (1H, t, d, J=7.2 Hz, 1.2 Hz), 7.291 (1H, t, J=7.2 Hz), 7.246 (1H, m), 7.216 (1H, t, J=8.4 Hz), 7.154 (1H, br d, J=7.6 Hz), 7.100 (1H, t, t J=7.6 Hz, 1.2 Hz), 7.013 (1H, d, d, J=8.6 Hz, 1.2 Hz), 6.713 (1H, d, d, d, J=8.4 Hz, 2.4 Hz, 0.8 Hz), 6.630 (1H, t, J=2.4 Hz), 6.603 (1H, d, d, d, J=8.0 Hz, 2.2 Hz, 1.2 Hz), 4.981 (2H, s), 3.657 (3H, s), 2.958 (2H, t, J=7.6 Hz), 2.627 (2H, t, J=8.0 Hz).

¹³C-NMR (100 MHz, CDCl₃): 173.20, 160.08, 158.53, 156.85, 140.91, 136.93, 130.12, 129.70, 128.75, 127.96, 127.45, 125.52, 123.39, 119.15, 111.20, 109.59, 105.65, 70.07, 51.58, 35.57, 30.83.

Elemental analysis: $C_{23}H_{22}O_4$: calc'd C, 76.22; H, 6.12; N, 0.00; found C, 76.02; H, 6.18; N, 0.00.

HRMS (ESI-TOF, [M+Na]$^+$): $C_{23}H_{22}NaO_4^+$: calc'd 385.14103; found 385.14221.

Synthesis of Compound 50

[Formula 104]

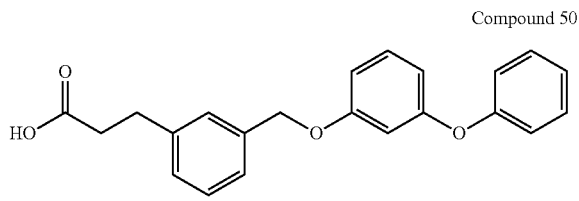

Compound 50

Intermediate 50-3 (272.8 mg) was dissolved in methanol (3 mL) and THF (4 mL) and sodium hydroxide (2 N aqueous solution, 3 mL) was added, followed by stirring at room temperature for 2 hours. Following dilution with water (100 mL), 2 N HCl (5 mL) was added to render the liquid reaction mixture acidic. The solution was subjected to extraction with ethyl acetate (125 mL) and the organic layers were combined and dried with magnesium sulfate; the solvent was distilled off to give the titled compound (257.0 mg, 98%, white solids).

$^1$H-NMR (400 MHz, CDCl$_3$): 7.323 (1H, d, d, J=8.2 Hz, 1.2 Hz), 7.289 (1H, d, J=7.6 Hz), 7.252 (1H, m), 7.215 (1H, t, J=8.4 Hz), 7.163 (1H, brd d, J=7.6 Hz), 7.098 (1H, t, t, J=7.6 Hz, 1.2 Hz), 7.011 (2H, d, d, J=8.2 Hz, 1.2 Hz), 6.713 (1H, d, d, d, J=8.4 Hz, 2.4 Hz, 0.8 Hz), 6.633 (1H, t, J=2.4 Hz), 6.601 (1H, d, d, d, J=7.4 Hz, 2.0 Hz, 0.8 Hz), 4.984 (2H, s), 2.963 (2H, t, J=8.0 Hz), 2.676 (2H, t, J=7.6 Hz).

$^{13}$C-NMR (100 MHz, CDCl$_3$): 178.23, 160.07, 158.53, 156.86, 140.55, 137.01, 130.14, 129, 72, 128.83, 127.96, 127.46, 125.64, 123.41, 119.16, 111.23, 109.64, 105.69, 70.06, 35.35, 30.49.

HRMS (ESI-TOF, [M-H]$^-$): $C_{22}H_{19}O_4^-$: calc'd 347.12888; found 347.13222.

HRMS (ESI-TOF, [M+Na]$^+$): $C_{22}H_{19}O_4$+Na$^+$: calc'd 371.12538; found 371.12633.

Elemental analysis: $C_{22}H_{20}O_4$: calc'd C, 75.84; H, 5.79; N, 0.00; found C, 75.52; H, 6.05; N, 0.00.

M.p. 68-69° C. (colorless solid cube, recrystallized from CH$_2$Cl$_2$/n-hexane).

Evaluation of Agonistic Activity Against GPR34, P2Y10 and GPR174

[Test Example 1] Agonistic Activity Evaluation by TGFα Cleavage Assay

In a Dulbecco's modified Eagle's medium (DMEM) containing 10% bovine fetal calf serum (FCS), HEK293 cells were suspended to give a density of 2.0×10$^5$ cells/mL and seeded in 4 mL portions in 60 mm dishes. After 24-hr culture in the presence of 5% CO$_2$, transfection with various expression vectors was performed using LipofectAMINE 2000 (Invitrogen). For each 60 mm dish, a plasmid vector for AP labeled TGFα was used in an amount of 1 μg and a pCAGGS plasmid vector for mouse GPR34, P2Y10 or GPR174 was also used in an amount of 1 μg. The plasmid vectors were provided by the methods disclosed in Patent Documents 2 and 5. It should be noted that the AP labeled TGFα is a protein having a human placental alkaline phosphatase fused to the N terminal of membrane-bound pro-TGFα, and a plasmid vector for the AP labeled TGFα can be prepared based on the disclosure of Tokumaru et al., J Cell Biol 151, 209-220 (2000). Twenty-four hours after transfection, cells were dissociated using trypsin/EDTA, resuspended in the culture broth to give a density of 2.0×10$^4$ cells/well, and seeded in a 96-well plate. In the case of stimulation with compounds, a Hank's balanced salt solution (HBSS, containing 5 mM HEPES) was used. After standing for 30 minutes, test compounds were added at varying concentrations, followed by standing for an additional one hour in the presence of 5% CO$_2$. The 96-well plate was centrifuged (190×g, 3 min) and 80 μL of the supernatant was transferred to another 96-well plate. A reaction buffer (40 mM Tris-HCl (pH 9.5)) containing 10 mM p-nitrophenyl phosphate (p-NPP) was added in an amount of 80 μL to both the supernatant and the cells. After OD$_{405}$ measurement with a microplate reader (background), heating was done at 37° C. for an hour and then another OD$_{405}$ measurement was performed. For each well, the background was subtracted from the absorbance measured the second time and the result was fitted to the following formula to calculate AP activity.

[Formula 105]
$$AP \text{ activity } (\%) = \frac{OD_{405} \text{ of supernatant}}{OD_{405} \text{ of supernatant} + OD_{405} \text{ of cells}}$$

Further, the values obtained by subtracting the AP activity (%) for the unstimulated group were plotted on the vertical axis to draw a graph. The EC$_{50}$ values calculated for the respective test compounds of Examples 2-4, 6, 7, 9, 10 and 12 were compared with the EC$_{50}$ value of Reference Compound 1 represented below to calculate the agonistic activity of each compound; the results are shown in Table 3 below. For activity calculation, the compound concentration and AP activity (%) were plotted and the following criteria were adopted: +++ (the activity of Reference Compound 1 (LPS18:1)); ++++ (10 times more active than Reference Compound 1); +++++ (100 times more active); ++ (10 times less active); + (100 times less active); − (even less active). The EC$_{50}$ values of the respective compounds are also cited in parentheses.

[Formula 106]

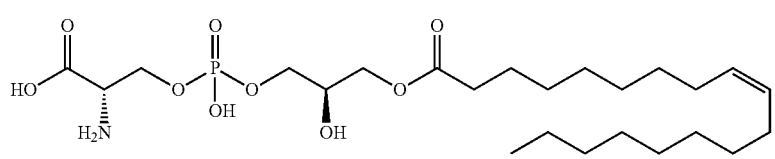

Reference Compound 1

TABLE 3

Test Results of TGFα Cleavage Assay

| Example | GPR34/LPS1 | P2Y10/LPS2 | GPR174/LPS3 |
|---|---|---|---|
| Reference Example 1 | +++ (230 nM) | +++ (8.3 nM) | +++ (81 nM) |
| 2 | − | +++~++++ (14 nM) | − |
| 3 | − | +++~++++ (7 nM) | +~++ (340 nM) |
| 4 | +++ | ++ | + |
| 6 | −~++ | ++++ (3.3 nM) | +~++ |
| 7 | − | ++~+++ (31 nM) | −~+ |
| 9 | − | +++ (30 nM) | − |
| 10 | −~+ | ++ | +~++ |
| 12 | − | ++++~+++++ (1.5 nM) | + |

As shown in Table 3, the compounds of Examples 2, 3, 6, 7, 9 and 12 were verified to be agonists having selectivity for P2Y10.

The invention claimed is:

1. A compound represented by formula (I):

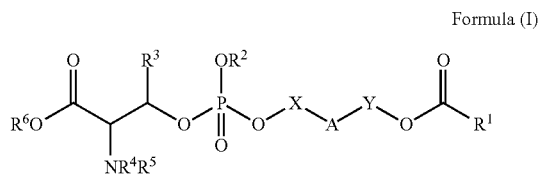

Formula (I)

wherein:
$R^1$ is represented by the following group:
$C_{1-30}$ alkyl optionally substituted by one or more $R^8$, $C_{2-30}$ alkenyl optionally substituted by one or more $R^8$, or $C_{2-30}$ alkynyl optionally substituted by one or more $R^8$, where $R^8$ is independently selected from among $C_{1-6}$ alkyl, $C_{1-6}$ alkoxy, and a halogen atom, or is a group represented by the formula:

—($C_{0-15}$ alkylene)-$Q^1$-$Z^1$—($C_{0-15}$ alkylene)-$Z^2$-$Q^2$, where $Q^1$ is a $C_{3-10}$ cycloalkylene optionally substituted by one or more $R^9$, a 5- to 10-membered heterocyclylene optionally substituted by one or more $R^9$, a $C_{6-10}$ arylene optionally substituted by one or more $R^9$, or a 5- to 10-membered heteroarylene optionally substituted by one or more $R^9$, where $R^9$ is independently selected from among $C_{1-6}$ alkyl, $C_{1-6}$ alkoxy, and a halogen atom;

$Q^2$ is a hydrogen atom, a $C_{3-10}$ cycloalkyl optionally substituted by one or more $R^{10}$, a 5- to 10-membered heterocyclyl optionally substituted by one or more $R^{10}$, a $C_{6-10}$ aryl optionally substituted by one or more $R^{10}$, or a 5- to 10-membered heteroaryl optionally substituted by one or more $R^{10}$, where $R^{10}$ is independently selected from among $C_{1-6}$ alkyl, $C_{1-6}$ alkoxy, a halogen atom, and —$Z^3$—($C_{0-15}$ alkylene)-$Q^3$, $Q^3$ is a $C_{3-10}$ cycloalkyl optionally substituted by one or more $R^{11}$, a 5- to 10-membered heterocyclyl optionally substituted by one or more $R^{11}$, a $C_{6-10}$ aryl optionally substituted by one or more $R^{11}$, or a 5- to 10-membered heteroaryl optionally substituted by one or more $R^{11}$, where $R^{11}$ is independently selected from among $C_{1-6}$ alkyl, $C_{2-6}$ alkenyl, $C_{2-6}$ alkynyl, $C_{1-6}$ alkoxy, $C_{1-6}$ alkylsulfonyl, hydroxyl $C_{1-6}$ alkyl, $C_{7-14}$ aralkyl, $C_{1-6}$ alkoxy $C_{1-6}$ alkyl, $C_{3-10}$ cycloalkyl, 5- to 10-membered heterocyclyl, $C_{6-10}$ aryl, 5- to 10-membered heteroaryl, cyano, amino, nitro, trifluoromethyl, halogen atom, and hydroxy;

$Z^1$, $Z^2$ and $Z^3$ are independently selected from the group consisting of an oxygen atom, a sulfur atom, —$NR^7$—, —CO—, —$SO_2$—, difluoromethylene, and a direct bond, where $R^7$ is a hydrogen atom or $C_{1-6}$ alkyl, provided that in the case of —$Z^1$—($C_{0-1}$ alkylene)-$Z^2$—, either one of $Z^1$ and $Z^2$ is an oxygen atom and the other is a direct bond or both of them are direct bonds;

$R^2$ is a hydrogen atom, $C_{1-6}$ alkyl, $C_{7-14}$ aralkyl, or $C_{1-6}$ alkoxy $C_{1-6}$ alkyl;

$R^3$ is a hydrogen atom or $C_{1-6}$ alkyl;

$R^4$ and $R^5$ are independently selected from the group consisting of a hydrogen atom, $C_{1-6}$ alkyl, $C_{7-14}$ aralkyl, formyl, $C_{1-6}$ alkylcarbonyl, $C_{6-10}$ arylcarbonyl, $C_{1-6}$ alkoxycarbonyl, $C_{1-6}$ alkoxy $C_{1-6}$ alkyl, and $C_{7-14}$ aralkyloxycarbonyl;

$R^6$ is a hydrogen atom, $C_{1-6}$ alkyl, $C_{1-6}$ alkoxy $C_{1-6}$ alkyl, or $C_{7-14}$ aralkyl;

A is phenylene or ethynylene;

X and Y are independently $CH_2$ or a direct bond, or a salt thereof.

2. The compound according to claim 1, which is represented by formula (IA):

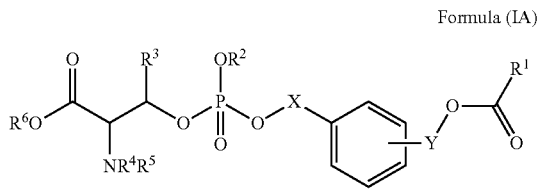

Formula (IA)

wherein $R^1$, $R^2$, $R^3$, $R^4$, $R^5$, $R^6$, X, and Y are as defined above,
or a salt thereof.

3. The compound according to claim 1, which is represented by formula (IB):

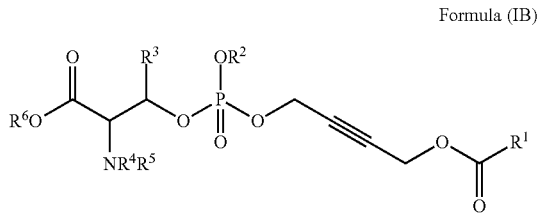

Formula (IB)

wherein $R^1$, $R^2$, $R^3$, $R^4$, $R^5$, and $R^6$ are as defined above,
or a salt thereof.

4. The compound according to claim 1, wherein $R^3$ is a hydrogen atom or methyl, or a salt thereof.

5. The compound according to claim 1, wherein:
$R^2$ is a hydrogen atom;
$R^4$ and $R^5$ are each a hydrogen atom; and
$R^6$ is a hydrogen atom,
or a salt thereof.

6. The compound according to claim 1, wherein $R^1$ is selected from among the following formulas:

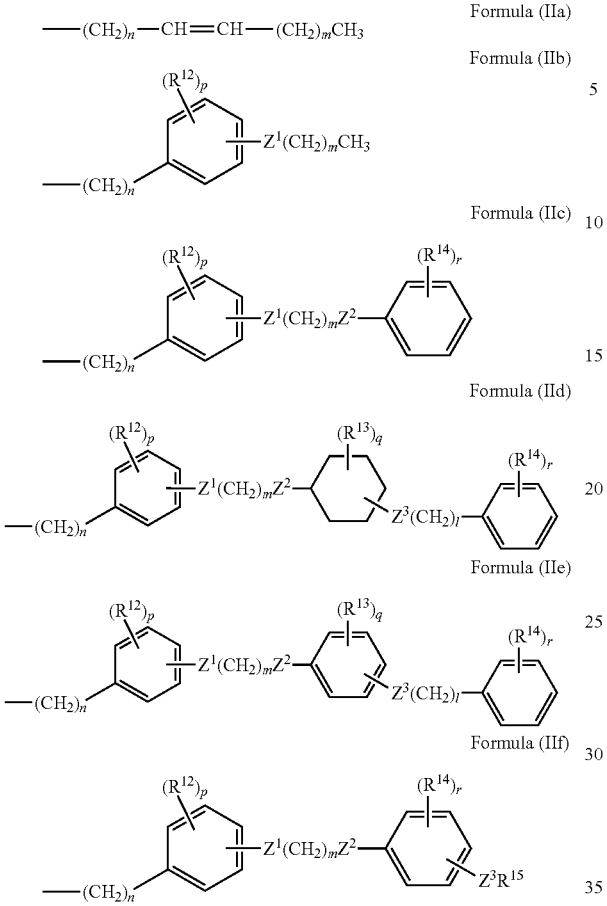

wherein:
R¹² and R¹³ are independently selected from among $C_{1-6}$ alkyl, $C_{1-6}$ alkoxy, and a halogen atom,
R¹⁴ is independently selected from among $C_{1-6}$ alkyl, $C_{2-6}$ alkenyl, $C_{2-6}$ alkynyl, $C_{1-6}$ alkoxy, $C_{1-6}$ alkylsulfonyl, hydroxyl $C_{1-6}$ alkyl, $C_{7-14}$ aralkyl, $C_{1-6}$ alkoxy $C_{1-6}$ alkyl, $C_{3-10}$ cycloalkyl, 5- to 10-membered heterocyclyl, $C_{6-10}$ aryl, 5- to 10-membered heteroaryl, cyano, amino, nitro, trifluoromethyl, a halogen atom, and hydroxy,
R¹⁵ is selected from among $C_{3-15}$ alkyl, $C_{3-10}$ cycloalkyl, and 5- to 10-membered heterocyclyl,
l and m are independently 0 to 15,
n is 0 to 15,
Z¹ and Z² are such that in the case where m is 0 or 1, either one of them is an oxygen atom while the other is a direct bond or both of them are direct bonds, and in the case where m is 2 to 15, Z¹ and Z² are independently selected from the group consisting of an oxygen atom and a direct bond,
Z³ is independently selected from the group consisting of an oxygen atom, a sulfur atom, —NR⁷—, —CO—, —SO₂—, difluoromethylene, and a direct bond, where R⁷ is a hydrogen atom or $C_{1-6}$ alkyl, p and q are independently 0 to 4,
r is 0 to 5 in the case of formulas (IIc) to (IIe), and 0 to 4 in the case of formula (IIf), or a salt thereof.

7. The compound according to claim 6, wherein R¹⁴ is independently selected from among $C_{1-6}$ alkyl, $C_{1-6}$ alkoxy, $C_{6-10}$ aryl, $C_{6-10}$ aryloxy, and a halogen atom, or a salt thereof.

8. A compound selected from:
O-(hydroxy(2-((3-(2-(undecyloxy)phenyl)propanoyl)oxy)phenoxy)phosphoryl)-L-serine;
O-(hydroxy(3-((3-(2-(undecyloxy)phenyl)propanoyl)oxy)phenoxy)phosphoryl)-L-serine;
O-(hydroxy(4-((3-(2-(undecyloxy)phenyl)propanoyl)oxy)phenoxy)phosphoryl)-L-serine;
O-(hydroxy(2-(((3-(2-(undecyloxy)phenyl)propanoyl)oxy)methyl)phenoxy)phosphoryl)-L-serine;
O-(hydroxy(2-(((3-(2-((3-phenoxybenzyl)oxy)phenyl)propanoyl)oxy)methyl)phenoxy)phosphoryl)-L-serine;
O-(hydroxy(3-(((3-(2-(undecyloxy)phenyl)propanoyl)oxy)methyl)phenoxy)phosphoryl)-L-serine;
O-(hydroxy(3-(((3-(2-((3-phenoxybenzyl)oxy)phenyl)propanoyl)oxy)methyl)phenoxy)phosphoryl)-L-serine;
O-(hydroxy(4-(((3-(2-(undecyloxy)phenyl)propanoyl)oxy)methyl)phenoxy)phosphoryl)-L-serine;
O-(hydroxy((3-((3-(2-(undecyloxy)phenyl)propanoyl)oxy)benzyl)oxy)phosphoryl)-L-serine;
O-(hydroxy((3-((3-(2-((3-phenoxybenzyl)oxy)phenyl)propanoyl)oxy)benzyl)oxy)phosphoryl)-L-serine;
O-(hydroxy((4-((3-(2-(undecyloxy)phenyl)propanoyl)oxy)benzyl)oxy)phosphoryl)-L-serine;
O-(hydroxy((4-((3-(2-(undecyloxy)phenyl)propanoyl)oxy)but-2-yn-1-yl)oxy)phosphoryl)-L-serine;
O-(hydroxy(4-(((3-(2-((3-phenoxybenzyl)oxy)phenyl)propanoyl)oxy)methyl)phenoxy)phosphoryl)-L-serine; and
O-(hydroxy((3-(((3-(2-(undecyloxy)phenyl)propanoyl)oxy)methyl)benzyl)oxy)phosphoryl)-L-serine,
or a salt thereof.

9. A pharmaceutical composition, comprising the compound or salt thereof according to claim 1.

10. A method of modulating a lysophosphatidylserine receptor function, comprising administering an effective amount of a compound or salt thereof according to claim 1 which acts on any one or more lysophosphatidylserine receptors selected from among GPR34, P2Y10, and GPR174.

11. The method according to claim 10, wherein the compound or salt thereof acts on any two lysophosphatidylserine receptors selected from among GPR34, P2Y10, and GPR174.

12. The method according to claim 10, wherein the compound or salt thereof selectively acts on P2Y10.

13. The method according to claim 10, wherein the compound or salt thereof has a lysophosphatidylserine receptor agonistic activity.

14. A method of treating autoimmune disease, comprising administering an effective amount of a compound or salt thereof according to claim 1 to a patient.

* * * * *